United States Patent
Levin et al.

(10) Patent No.: US 10,504,386 B2
(45) Date of Patent: Dec. 10, 2019

(54) TRAINING METHOD AND SYSTEM FOR ORAL-CAVITY-IMAGING-AND-MODELING EQUIPMENT

(71) Applicant: Align Technology, Inc., San Jose, CA (US)

(72) Inventors: Adi Levin, Nes Ziona (IL); Gilad Furst, Petach Tikva (IL)

(73) Assignee: Align Technology, Inc., San Jose, CA (US)

( * ) Notice: Subject to any disclaimer, the term of this patent is extended or adjusted under 35 U.S.C. 154(b) by 340 days.

(21) Appl. No.: 14/993,798

(22) Filed: Jan. 12, 2016

(65) Prior Publication Data

US 2016/0217708 A1 Jul. 28, 2016

Related U.S. Application Data

(60) Provisional application No. 62/108,263, filed on Jan. 27, 2015.

(51) Int. Cl.
*G06F 3/0481* (2013.01)
*G09B 23/28* (2006.01)
(Continued)

(52) U.S. Cl.
CPC ......... *G09B 23/283* (2013.01); *G06F 3/0481* (2013.01); *G06T 1/0007* (2013.01); *A61C 9/0053* (2013.01); *G06T 2200/24* (2013.01)

(58) Field of Classification Search
CPC ... G09B 23/283; G06F 3/0481; G06T 1/0007; G06T 2207/30036; A61C 9/0046; A61C 9/0053
See application file for complete search history.

(56) References Cited

U.S. PATENT DOCUMENTS 2,171,695 A 9/1939 Harper
2,194,790 A 3/1940 Gluck
(Continued)

FOREIGN PATENT DOCUMENTS

AU 517102 B 11/1977
AU 3031677 A 11/1977
(Continued)

OTHER PUBLICATIONS

US 8,553,966 B1, 10/2013, Alpern et al. (withdrawn)
(Continued)

*Primary Examiner* — Bruk A Gebremichael
(74) *Attorney, Agent, or Firm* — Shay Glenn LLP

(57) ABSTRACT

The current document is directed to methods and systems that provide semi-automated and automated training to technicians who use oral-cavity-imaging-and-modeling systems to accurately and efficiently generate three-dimensional models of patients' teeth and underlying tissues. The training methods and systems are implemented either as subsystems within oral-cavity-imaging-and-modeling systems or as separate system in electronic communication oral-cavity-imaging-and-modeling systems. The training methods and systems use an already generated, digital, three-dimensional model of a portion of the oral cavity of a particular patient or of a physical model of a portion of an oral cavity to compute a temporal, translational, and rotational trajectory of an oral-cavity-imaging-and-modeling endoscope, or wand, during a training scan. The temporal, translational, and rotational trajectory is used for a variety of different types of instruction and instructional feedback to facilitate training of technicians.

15 Claims, 43 Drawing Sheets

(51) Int. Cl.
*G06T 1/00* (2006.01)
*A61C 9/00* (2006.01)

(56) References Cited

U.S. PATENT DOCUMENTS

| | | |
|---|---|---|
| 2,467,432 A | 4/1949 | Kesling |
| 2,531,222 A | 11/1950 | Kesling |
| 3,089,487 A | 5/1963 | Enicks et al. |
| 3,092,907 A | 6/1963 | Traiger |
| 3,178,820 A | 4/1965 | Kesling |
| 3,211,143 A | 10/1965 | Grossberg |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,724,075 A | 4/1973 | Kesling |
| 3,738,005 A | 6/1973 | Cohen et al. |
| 3,797,115 A | 3/1974 | Silverman et al. |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,949,477 A | 4/1976 | Cohen et al. |
| 3,950,851 A | 4/1976 | Bergersen |
| 3,955,282 A | 5/1976 | McNall |
| 3,983,628 A | 10/1976 | Acevedo |
| 4,014,096 A | 3/1977 | Dellinger |
| 4,055,895 A | 11/1977 | Huge |
| 4,094,068 A | 6/1978 | Schinhammer |
| 4,117,596 A | 10/1978 | Wallshein |
| 4,129,946 A | 12/1978 | Kennedy |
| 4,134,208 A | 1/1979 | Pearlman |
| 4,139,944 A | 2/1979 | Bergersen |
| 4,179,811 A | 12/1979 | Hinz |
| 4,179,812 A | 12/1979 | White |
| 4,183,141 A | 1/1980 | Dellinger |
| 4,195,046 A | 3/1980 | Kesling |
| 4,204,325 A | 5/1980 | Kaelble |
| 4,253,828 A | 3/1981 | Coles et al. |
| 4,255,138 A | 3/1981 | Frohn |
| 4,299,568 A | 11/1981 | Crowley |
| 4,324,546 A | 4/1982 | Heitlinger et al. |
| 4,324,547 A | 4/1982 | Arcan et al. |
| 4,348,178 A | 9/1982 | Kurz |
| 4,368,040 A | 1/1983 | Weissman |
| 4,419,992 A | 12/1983 | Chorbajian |
| 4,433,956 A | 2/1984 | Witzig |
| 4,433,960 A | 2/1984 | Garito et al. |
| 4,439,154 A | 3/1984 | Mayclin |
| 4,449,928 A | 5/1984 | von Weissenfluh |
| 4,478,580 A | 10/1984 | Barrut |
| 4,500,294 A | 2/1985 | Lewis |
| 4,505,672 A | 3/1985 | Kurz |
| 4,505,673 A | 3/1985 | Yoshii |
| 4,519,386 A | 5/1985 | Sullivan |
| 4,523,908 A | 6/1985 | Drisaldi et al. |
| 4,526,540 A | 7/1985 | Dellinger |
| 4,553,936 A | 11/1985 | Wang |
| 4,575,330 A | 3/1986 | Hull |
| 4,575,805 A | 3/1986 | Moermann et al. |
| 4,591,341 A | 5/1986 | Andrews |
| 4,608,021 A | 8/1986 | Barrett |
| 4,609,349 A | 9/1986 | Cain |
| 4,611,288 A | 9/1986 | Duret et al. |
| 4,629,424 A | 12/1986 | Lauks et al. |
| 4,638,145 A | 1/1987 | Sakuma et al. |
| 4,656,860 A | 4/1987 | Orthuber et al. |
| 4,663,720 A | 5/1987 | Duret et al. |
| 4,664,626 A | 5/1987 | Kesling |
| 4,665,621 A | 5/1987 | Ackerman et al. |
| 4,676,747 A | 6/1987 | Kesling |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,790,752 A | 12/1988 | Cheslak |
| 4,793,803 A | 12/1988 | Martz |
| 4,798,534 A | 1/1989 | Breads |
| 4,830,612 A | 5/1989 | Bergersen |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,932,866 A | 6/1990 | Guis |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,971,557 A | 11/1990 | Martin |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,015,183 A | 5/1991 | Fenick |
| 5,017,133 A | 5/1991 | Miura |
| 5,018,969 A | 5/1991 | Andreiko et al. |
| 5,027,281 A | 6/1991 | Rekow et al. |
| 5,035,613 A | 7/1991 | Breads et al. |
| 5,037,295 A | 8/1991 | Bergersen |
| 5,055,039 A | 10/1991 | Abbatte et al. |
| 5,061,839 A | 10/1991 | Matsuno et al. |
| 5,083,919 A | 1/1992 | Quach |
| 5,094,614 A | 3/1992 | Wildman |
| 5,100,316 A | 3/1992 | Wildman |
| 5,103,838 A | 4/1992 | Yousif |
| 5,114,339 A | 5/1992 | Guis |
| 5,121,333 A | 6/1992 | Riley et al. |
| 5,123,425 A | 6/1992 | Shannon et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,194,003 A | 3/1993 | Garay et al. |
| 5,204,670 A | 4/1993 | Stinton |
| 5,222,499 A | 6/1993 | Allen et al. |
| 5,224,049 A | 6/1993 | Mushabac |
| 5,238,404 A | 8/1993 | Andreiko |
| 5,242,304 A | 9/1993 | Truax et al. |
| 5,245,592 A | 9/1993 | Kuemmel et al. |
| 5,273,429 A | 12/1993 | Rekow et al. |
| 5,278,756 A | 1/1994 | Lemchen et al. |
| 5,306,144 A | 4/1994 | Hibst et al. |
| 5,314,335 A | 5/1994 | Fung |
| 5,324,186 A | 6/1994 | Bakanowski |
| 5,328,362 A | 7/1994 | Watson et al. |
| 5,335,657 A | 8/1994 | Terry et al. |
| 5,338,198 A | 8/1994 | Wu et al. |
| 5,340,309 A | 8/1994 | Robertson |
| 5,342,202 A | 8/1994 | Deshayes |
| 5,344,315 A | 9/1994 | Hanson |
| 5,368,478 A | 11/1994 | Andreiko et al. |
| 5,372,502 A | 12/1994 | Massen et al. |
| D354,355 S | 1/1995 | Hilgers |
| 5,382,164 A | 1/1995 | Stern |
| 5,395,238 A | 3/1995 | Andreiko et al. |
| 5,415,542 A | 5/1995 | Kesling |

(56) References Cited

U.S. PATENT DOCUMENTS

| | | |
|---|---|---|
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,449,703 A | 9/1995 | Mitra et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,487,662 A | 1/1996 | Kipke et al. |
| RE35,169 E | 3/1996 | Lemchen et al. |
| 5,499,633 A | 3/1996 | Fenton |
| 5,522,725 A | 6/1996 | Jordan et al. |
| 5,528,735 A | 6/1996 | Strasnick et al. |
| 5,533,895 A | 7/1996 | Andreiko et al. |
| 5,540,732 A | 7/1996 | Testerman |
| 5,542,842 A | 8/1996 | Andreiko et al. |
| 5,543,780 A | 8/1996 | McAuley et al. |
| 5,549,476 A | 8/1996 | Stern |
| 5,562,448 A | 10/1996 | Mushabac |
| 5,570,182 A | 10/1996 | Nathel et al. |
| 5,575,655 A | 11/1996 | Darnell |
| 5,583,977 A | 12/1996 | Seidl |
| 5,587,912 A | 12/1996 | Andersson et al. |
| 5,588,098 A | 12/1996 | Chen et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,626,537 A | 5/1997 | Danyo et al. |
| 5,636,736 A | 6/1997 | Jacobs et al. |
| 5,645,420 A | 7/1997 | Bergersen |
| 5,645,421 A | 7/1997 | Slootsky |
| 5,651,671 A | 7/1997 | Seay et al. |
| 5,655,653 A | 8/1997 | Chester |
| 5,659,420 A | 8/1997 | Wakai et al. |
| 5,683,243 A | 11/1997 | Andreiko et al. |
| 5,683,244 A | 11/1997 | Truax |
| 5,691,539 A | 11/1997 | Pfeiffer |
| 5,692,894 A | 12/1997 | Schwartz et al. |
| 5,711,665 A | 1/1998 | Adam et al. |
| 5,711,666 A | 1/1998 | Hanson |
| 5,725,376 A | 3/1998 | Poirier |
| 5,725,378 A | 3/1998 | Wang |
| 5,730,151 A | 3/1998 | Summer et al. |
| 5,737,084 A | 4/1998 | Ishihara |
| 5,740,267 A | 4/1998 | Echerer et al. |
| 5,742,700 A | 4/1998 | Yoon et al. |
| 5,769,631 A | 6/1998 | Williams |
| 5,774,425 A | 6/1998 | Ivanov et al. |
| 5,790,242 A | 8/1998 | Stern et al. |
| 5,799,100 A | 8/1998 | Clarke et al. |
| 5,800,162 A | 9/1998 | Shimodaira et al. |
| 5,800,174 A | 9/1998 | Andersson |
| 5,813,854 A | 9/1998 | Nikodem |
| 5,816,800 A | 10/1998 | Brehm et al. |
| 5,818,587 A | 10/1998 | Devaraj et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,876,199 A | 3/1999 | Bergersen |
| 5,879,158 A | 3/1999 | Doyle et al. |
| 5,880,961 A | 3/1999 | Crump |
| 5,880,962 A | 3/1999 | Andersson et al. |
| 5,882,192 A | 3/1999 | Bergersen |
| 5,886,702 A | 3/1999 | Migdal et al. |
| 5,890,896 A | 4/1999 | Padial |
| 5,904,479 A | 5/1999 | Staples |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 5,975,906 A | 11/1999 | Knutson |
| 5,980,246 A | 11/1999 | Ramsay et al. |
| 5,989,023 A | 11/1999 | Summer et al. |
| 6,002,706 A | 12/1999 | Stayer et al. |
| 6,018,713 A | 1/2000 | Coli et al. |
| 6,044,309 A | 3/2000 | Honda |
| 6,049,743 A | 4/2000 | Baba |
| 6,053,731 A | 4/2000 | Heckenberger |
| 6,068,482 A | 5/2000 | Snow |
| 6,070,140 A | 5/2000 | Tran |
| 6,099,303 A | 8/2000 | Gibbs et al. |
| 6,099,314 A | 8/2000 | Kopelman et al. |
| 6,102,701 A | 8/2000 | Engeron |
| 6,120,287 A | 9/2000 | Chen |
| 6,123,544 A | 9/2000 | Cleary |
| 6,152,731 A | 11/2000 | Jordan et al. |
| 6,154,676 A | 11/2000 | Levine |
| 6,183,248 B1 | 2/2001 | Chishti et al. |
| 6,183,249 B1 | 2/2001 | Brennan et al. |
| 6,186,780 B1 | 2/2001 | Hibst et al. |
| 6,190,165 B1 | 2/2001 | Andreiko et al. |
| 6,200,133 B1 | 3/2001 | Kittelsen |
| 6,201,880 B1 | 3/2001 | Elbaum et al. |
| 6,210,162 B1 | 4/2001 | Chishti et al. |
| 6,212,435 B1 | 4/2001 | Lattner et al. |
| 6,213,767 B1 | 4/2001 | Dixon et al. |
| 6,217,334 B1 | 4/2001 | Hultgren |
| 6,227,850 B1 | 5/2001 | Chishti et al. |
| 6,231,338 B1 | 5/2001 | de Josselin de Jong et al. |
| 6,239,705 B1 | 5/2001 | Glen |
| 6,243,601 B1 | 6/2001 | Wist |
| 6,263,234 B1 | 7/2001 | Engelhardt et al. |
| 6,283,761 B1 | 9/2001 | Joao |
| 6,288,138 B1 | 9/2001 | Yamamoto |
| 6,299,438 B1 | 10/2001 | Sahagian et al. |
| 6,309,215 B1 | 10/2001 | Phan et al. |
| 6,313,432 B1 | 11/2001 | Nagata et al. |
| 6,315,553 B1 | 11/2001 | Sachdeva et al. |
| 6,328,745 B1 | 12/2001 | Ascherman |
| 6,332,774 B1 | 12/2001 | Chikami |
| 6,334,073 B1 | 12/2001 | Levine |
| 6,350,120 B1 | 2/2002 | Sachdeva et al. |
| 6,364,660 B1 | 4/2002 | Durbin et al. |
| 6,382,975 B1 | 5/2002 | Poirier |
| 6,386,878 B1 | 5/2002 | Pavlovskaia et al. |
| 6,394,802 B1 | 5/2002 | Hahn |
| 6,402,510 B1 | 6/2002 | Williams |
| 6,402,707 B1 | 6/2002 | Ernst |
| 6,405,729 B1 | 6/2002 | Thornton |
| 6,406,292 B1 | 6/2002 | Chishti et al. |
| 6,409,504 B1 | 6/2002 | Jones et al. |
| 6,413,086 B1 | 7/2002 | Womack |
| 6,414,264 B1 | 7/2002 | von Falkenhausen |
| 6,414,708 B1 | 7/2002 | Carmeli et al. |
| 6,435,871 B1 | 8/2002 | Inman |
| 6,436,058 B1 | 8/2002 | Krahner et al. |
| 6,441,354 B1 | 8/2002 | Seghatol et al. |
| 6,450,167 B1 | 9/2002 | David et al. |
| 6,450,807 B1 | 9/2002 | Chishti et al. |
| 6,462,301 B1 | 10/2002 | Scott et al. |
| 6,470,338 B1 | 10/2002 | Rizzo et al. |
| 6,471,511 B1 | 10/2002 | Chishti et al. |
| 6,471,512 B1 | 10/2002 | Sachdeva et al. |
| 6,471,970 B1 | 10/2002 | Fanara et al. |
| 6,482,002 B2 | 11/2002 | Jordan et al. |
| 6,482,298 B1 | 11/2002 | Bhatnagar |
| 6,496,814 B1 | 12/2002 | Busche |
| 6,496,816 B1 | 12/2002 | Thiesson et al. |
| 6,499,026 B1 | 12/2002 | Rivette et al. |
| 6,499,995 B1 | 12/2002 | Schwartz |
| 6,507,832 B1 | 1/2003 | Evans et al. |
| 6,514,074 B1 | 2/2003 | Chishti et al. |
| 6,515,593 B1 | 2/2003 | Stark et al. |
| 6,516,288 B2 | 2/2003 | Bagne |
| 6,516,805 B1 | 2/2003 | Thornton |
| 6,520,772 B2 | 2/2003 | Williams |
| 6,523,009 B1 | 2/2003 | Wilkins |
| 6,523,019 B1 | 2/2003 | Borthwick |
| 6,524,101 B1 | 2/2003 | Phan et al. |
| 6,526,168 B1 | 2/2003 | Ornes et al. |

(56) References Cited

U.S. PATENT DOCUMENTS

| | | |
|---|---|---|
| 6,526,982 B1 | 3/2003 | Strong |
| 6,529,891 B1 | 3/2003 | Heckerman |
| 6,529,902 B1 | 3/2003 | Kanevsky et al. |
| 6,532,455 B1 | 3/2003 | Martin et al. |
| 6,535,865 B1 | 3/2003 | Skaaning et al. |
| 6,540,512 B1 | 4/2003 | Sachdeva et al. |
| 6,540,707 B1 | 4/2003 | Stark et al. |
| 6,542,593 B1 | 4/2003 | Bowman Amuah |
| 6,542,881 B1 | 4/2003 | Meidan et al. |
| 6,542,894 B1 | 4/2003 | Lee et al. |
| 6,542,903 B2 | 4/2003 | Hull et al. |
| 6,551,243 B2 | 4/2003 | Bocionek et al. |
| 6,554,837 B1 | 4/2003 | Hauri et al. |
| 6,556,659 B1 | 4/2003 | Bowman Amuah |
| 6,556,977 B1 | 4/2003 | Lapointe et al. |
| 6,560,592 B1 | 5/2003 | Reid et al. |
| 6,564,209 B1 | 5/2003 | Dempski et al. |
| 6,567,814 B1 | 5/2003 | Bankier et al. |
| 6,571,227 B1 | 5/2003 | Agrafiotis et al. |
| 6,572,372 B1 | 6/2003 | Phan et al. |
| 6,573,998 B2 | 6/2003 | Cohen Sabban |
| 6,574,561 B2 | 6/2003 | Alexander et al. |
| 6,578,003 B1 | 6/2003 | Camarda et al. |
| 6,580,948 B2 | 6/2003 | Haupert et al. |
| 6,587,529 B1 | 7/2003 | Staszewski et al. |
| 6,587,828 B1 | 7/2003 | Sachdeva |
| 6,592,368 B1 | 7/2003 | Weathers |
| 6,594,539 B1 | 7/2003 | Geng |
| 6,595,342 B1 | 7/2003 | Maritzen et al. |
| 6,597,934 B1 | 7/2003 | de Jong et al. |
| 6,598,043 B1 | 7/2003 | Baclawski |
| 6,599,250 B2 | 7/2003 | Webb et al. |
| 6,602,070 B2 | 8/2003 | Miller et al. |
| 6,604,527 B1 | 8/2003 | Palmisano |
| 6,606,744 B1 | 8/2003 | Mikurak |
| 6,607,382 B1 | 8/2003 | Kuo et al. |
| 6,611,783 B2 | 8/2003 | Kelly et al. |
| 6,611,867 B1 | 8/2003 | Bowman Amuah |
| 6,613,001 B1 | 9/2003 | Dworkin |
| 6,615,158 B2 | 9/2003 | Wenzel et al. |
| 6,616,447 B1 | 9/2003 | Rizoiu et al. |
| 6,616,579 B1 | 9/2003 | Reinbold et al. |
| 6,621,491 B1 | 9/2003 | Baumrind et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,626,569 B2 | 9/2003 | Reinstein et al. |
| 6,626,669 B2 | 9/2003 | Zegarelli |
| 6,633,772 B2 | 10/2003 | Ford et al. |
| 6,640,128 B2 | 10/2003 | Vilsmeier et al. |
| 6,643,646 B2 | 11/2003 | Su et al. |
| 6,647,383 B1 | 11/2003 | August et al. |
| 6,650,944 B2 | 11/2003 | Goedeke et al. |
| 6,671,818 B1 | 12/2003 | Mikurak |
| 6,675,104 B2 | 1/2004 | Paulse et al. |
| 6,678,669 B2 | 1/2004 | Lapointe et al. |
| 6,682,346 B2 | 1/2004 | Chishti et al. |
| 6,685,469 B2 | 2/2004 | Chishti et al. |
| 6,689,055 B1 | 2/2004 | Mullen et al. |
| 6,690,761 B2 | 2/2004 | Lang et al. |
| 6,691,110 B2 | 2/2004 | Wang et al. |
| 6,694,234 B2 | 2/2004 | Lockwood et al. |
| 6,697,164 B1 | 2/2004 | Babayoff et al. |
| 6,697,793 B2 | 2/2004 | McGreevy |
| 6,702,765 B2 | 3/2004 | Robbins |
| 6,702,804 B1 | 3/2004 | Ritter et al. |
| 6,705,863 B2 | 3/2004 | Phan et al. |
| 6,729,876 B2 | 5/2004 | Chishti et al. |
| 6,733,289 B2 | 5/2004 | Manemann et al. |
| 6,736,638 B1 | 5/2004 | Sachdeva et al. |
| 6,739,869 B1 | 5/2004 | Taub et al. |
| 6,744,932 B1 | 6/2004 | Rubbert et al. |
| 6,749,414 B1 | 6/2004 | Hanson et al. |
| 6,769,913 B2 | 8/2004 | Hurson |
| 6,772,026 B2 | 8/2004 | Bradbury et al. |
| 6,790,036 B2 | 9/2004 | Graham |
| 6,802,713 B1 | 10/2004 | Chishti et al. |
| 6,814,574 B2 | 11/2004 | Abolfathi et al. |
| 6,830,450 B2 | 12/2004 | Knopp et al. |
| 6,832,912 B2 | 12/2004 | Mao |
| 6,832,914 B1 | 12/2004 | Bonnet et al. |
| 6,843,370 B2 | 1/2005 | Tuneberg |
| 6,845,175 B2 | 1/2005 | Kopelman et al. |
| 6,885,464 B1 | 4/2005 | Pfeiffer et al. |
| 6,890,285 B2 | 5/2005 | Rahman et al. |
| 6,951,254 B2 | 10/2005 | Morrison |
| 6,976,841 B1 | 12/2005 | Osterwalder |
| 6,978,268 B2 | 12/2005 | Thomas et al. |
| 6,983,752 B2 | 1/2006 | Garabadian |
| 6,984,128 B2 | 1/2006 | Breining et al. |
| 6,988,893 B2 | 1/2006 | Haywood |
| 7,016,952 B2 | 3/2006 | Mullen et al. |
| 7,020,963 B2 | 4/2006 | Cleary et al. |
| 7,036,514 B2 | 5/2006 | Heck |
| 7,040,896 B2 | 5/2006 | Pavlovskaia et al. |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,134,874 B2 | 11/2006 | Chishti et al. |
| 7,137,812 B2 | 11/2006 | Cleary et al. |
| 7,138,640 B1 | 11/2006 | Delgado et al. |
| 7,140,877 B2 | 11/2006 | Kaza |
| 7,142,312 B2 | 11/2006 | Quadling et al. |
| 7,155,373 B2 | 12/2006 | Jordan et al. |
| 7,156,655 B2 | 1/2007 | Sachdeva et al. |
| 7,156,661 B2 | 1/2007 | Choi et al. |
| 7,166,063 B2 | 1/2007 | Rahman et al. |
| 7,184,150 B2 | 2/2007 | Quadling et al. |
| 7,191,451 B2 | 3/2007 | Nakagawa |
| 7,192,273 B2 | 3/2007 | McSurdy |
| 7,217,131 B2 | 5/2007 | Vuillemot |
| 7,220,122 B2 | 5/2007 | Chishti |
| 7,220,124 B2 | 5/2007 | Taub et al. |
| 7,229,282 B2 | 6/2007 | Andreiko et al. |
| 7,234,937 B2 | 6/2007 | Sachdeva et al. |
| 7,241,142 B2 | 7/2007 | Abolfathi et al. |
| 7,244,230 B2 | 7/2007 | Duggirala et al. |
| 7,245,753 B2 | 7/2007 | Squilla et al. |
| 7,257,136 B2 | 8/2007 | Mori et al. |
| 7,286,954 B2 | 10/2007 | Kopelman et al. |
| 7,292,759 B2 | 11/2007 | Boutoussov et al. |
| 7,294,141 B2 | 11/2007 | Bergersen |
| 7,302,842 B2 | 12/2007 | Biester et al. |
| 7,320,592 B2 | 1/2008 | Chishti et al. |
| 7,328,706 B2 | 2/2008 | Barach et al. |
| 7,329,122 B1 | 2/2008 | Scott |
| 7,338,327 B2 | 3/2008 | Sticker et al. |
| D565,509 S | 4/2008 | Fechner et al. |
| 7,351,116 B2 | 4/2008 | Dold |
| 7,354,270 B2 | 4/2008 | Abolfathi et al. |
| 7,357,637 B2 | 4/2008 | Liechtung |
| 7,435,083 B2 | 10/2008 | Chishti et al. |
| 7,450,231 B2 | 11/2008 | Johs et al. |
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,476,100 B2 | 1/2009 | Kuo |
| 7,500,851 B2 | 3/2009 | Williams |
| D594,413 S | 6/2009 | Palka et al. |
| 7,543,511 B2 | 6/2009 | Kimura et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |
| 7,637,262 B2 | 12/2009 | Bailey |

(56) References Cited

U.S. PATENT DOCUMENTS

| | | |
|---|---|---|
| 7,637,740 B2 | 12/2009 | Knopp |
| 7,641,473 B2 | 1/2010 | Sporbert et al. |
| 7,668,355 B2 | 2/2010 | Wong et al. |
| 7,670,179 B2 | 3/2010 | Müller |
| 7,695,327 B2 | 4/2010 | Bäuerle et al. |
| 7,698,068 B2 | 4/2010 | Babayoff |
| 7,711,447 B2 | 5/2010 | Lu et al. |
| 7,724,378 B2 | 5/2010 | Babayoff |
| D618,619 S | 6/2010 | Walter |
| 7,728,848 B2 | 6/2010 | Petrov et al. |
| 7,731,508 B2 | 6/2010 | Borst |
| 7,735,217 B2 | 6/2010 | Borst |
| 7,740,476 B2 | 6/2010 | Rubbert et al. |
| 7,744,369 B2 | 6/2010 | Imgrund et al. |
| 7,746,339 B2 | 6/2010 | Matov et al. |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,687 B2 | 10/2010 | Minagi et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,841,464 B2 | 11/2010 | Cinader et al. |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,869,983 B2 | 1/2011 | Raby et al. |
| 7,872,760 B2 | 1/2011 | Ertl |
| 7,874,836 B2 | 1/2011 | McSurdy |
| 7,874,837 B2 | 1/2011 | Chishti et al. |
| 7,874,849 B2 | 1/2011 | Sticker et al. |
| 7,878,801 B2 | 2/2011 | Aboifathi et al. |
| 7,878,805 B2 | 2/2011 | Moss et al. |
| 7,880,751 B2 | 2/2011 | Kuo et al. |
| 7,892,474 B2 | 2/2011 | Shkolnik et al. |
| 7,904,308 B2 | 3/2011 | Arnone et al. |
| 7,907,280 B2 | 3/2011 | Johs et al. |
| 7,929,151 B2 | 4/2011 | Liang et al. |
| 7,930,189 B2 | 4/2011 | Kuo |
| 7,947,508 B2 | 5/2011 | Tricca et al. |
| 7,959,308 B2 | 6/2011 | Freeman et al. |
| 7,963,766 B2 | 6/2011 | Cronauer |
| 7,970,627 B2 | 6/2011 | Kuo et al. |
| 7,985,414 B2 | 7/2011 | Knaack et al. |
| 7,986,415 B2 | 7/2011 | Thiel et al. |
| 7,987,099 B2 | 7/2011 | Kuo et al. |
| 7,991,485 B2 | 8/2011 | Zakim |
| 8,017,891 B2 | 9/2011 | Nevin |
| 8,026,916 B2 | 9/2011 | Wen |
| 8,027,709 B2 | 9/2011 | Arnone et al. |
| 8,029,277 B2 | 10/2011 | Imgrund et al. |
| 8,038,444 B2 | 10/2011 | Kitching et al. |
| 8,045,772 B2 | 10/2011 | Kosuge et al. |
| 8,054,556 B2 | 11/2011 | Chen et al. |
| 8,070,490 B1 | 12/2011 | Roetzer et al. |
| 8,075,306 B2 | 12/2011 | Kitching et al. |
| 8,077,949 B2 | 12/2011 | Liang et al. |
| 8,083,556 B2 | 12/2011 | Stadler et al. |
| D652,799 S | 1/2012 | Mueller |
| 8,092,215 B2 | 1/2012 | Stone-Collonge et al. |
| 8,095,383 B2 | 1/2012 | Arnone et al. |
| 8,099,268 B2 | 1/2012 | Kitching et al. |
| 8,099,305 B2 | 1/2012 | Kuo et al. |
| 8,118,592 B2 | 2/2012 | Tortorici |
| 8,126,025 B2 | 2/2012 | Takeda |
| 8,136,529 B2 | 3/2012 | Kelly |
| 8,144,954 B2 | 3/2012 | Quadling et al. |
| 8,160,334 B2 | 4/2012 | Thiel et al. |
| 8,172,569 B2 | 5/2012 | Matty et al. |
| 8,197,252 B1 | 6/2012 | Harrison |
| 8,201,560 B2 | 6/2012 | Dembro |
| 8,215,312 B2 | 7/2012 | Garabadian et al. |
| 8,240,018 B2 | 8/2012 | Walter et al. |
| 8,275,180 B2 | 9/2012 | Kuo |
| 8,279,450 B2 | 10/2012 | Oota et al. |
| 8,292,617 B2 | 10/2012 | Brandt et al. |
| 8,294,657 B2 | 10/2012 | Kim et al. |
| 8,296,952 B2 | 10/2012 | Greenberg |
| 8,297,286 B2 | 10/2012 | Smernoff |
| 8,306,608 B2 | 11/2012 | Mandelis et al. |
| 8,314,764 B2 | 11/2012 | Kim et al. |
| 8,332,015 B2 | 12/2012 | Ertl |
| 8,354,588 B2 | 1/2013 | Sticker et al. |
| 8,366,479 B2 | 2/2013 | Borst et al. |
| 8,401,826 B2 | 3/2013 | Cheng et al. |
| 8,419,428 B2 | 4/2013 | Lawrence |
| 8,433,083 B2 | 4/2013 | Abolfathi et al. |
| 8,439,672 B2 | 5/2013 | Matov et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,517,726 B2 | 8/2013 | Kakavand et al. |
| 8,520,922 B2 | 8/2013 | Wang et al. |
| 8,520,925 B2 | 8/2013 | Duret et al. |
| 8,523,565 B2 | 9/2013 | Matty et al. |
| 8,545,221 B2 | 10/2013 | Stone-Collonge et al. |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,601,925 B1 | 12/2013 | Coto |
| 8,639,477 B2 | 1/2014 | Chelnokov et al. |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,738,394 B2 | 5/2014 | Kuo |
| 8,743,923 B2 | 6/2014 | Geske et al. |
| 8,753,114 B2 | 6/2014 | Vuillemot |
| 8,767,270 B2 | 7/2014 | Curry et al. |
| 8,768,016 B2 | 7/2014 | Pan et al. |
| 8,771,149 B2 | 7/2014 | Rahman et al. |
| 8,839,476 B2 | 9/2014 | Adachi |
| 8,843,381 B2 | 9/2014 | Kuo et al. |
| 8,856,053 B2 | 10/2014 | Mah |
| 8,870,566 B2 | 10/2014 | Bergersen |
| 8,874,452 B2 | 10/2014 | Kuo |
| 8,878,905 B2 | 11/2014 | Fisker et al. |
| 8,899,976 B2 | 12/2014 | Chen et al. |
| 8,936,463 B2 | 1/2015 | Mason et al. |
| 8,944,812 B2 | 2/2015 | Kou |
| 8,948,482 B2 | 2/2015 | Levin |
| 8,956,058 B2 | 2/2015 | Rösch |
| 8,992,216 B2 | 3/2015 | Karazivan |
| 9,004,915 B2 | 4/2015 | Moss et al. |
| 9,022,792 B2 | 5/2015 | Sticker et al. |
| 9,039,418 B1 | 5/2015 | Rubbert |
| 9,084,535 B2 | 7/2015 | Girkin et al. |
| 9,084,657 B2 | 7/2015 | Matty et al. |
| 9,108,338 B2 | 8/2015 | Sirovskiy et al. |
| 9,144,512 B2 | 9/2015 | Wagner |
| 9,192,305 B2 | 11/2015 | Levin |
| 9,204,952 B2 | 12/2015 | Lampalzer |
| 9,211,166 B2 | 12/2015 | Kuo et al. |
| 9,214,014 B2 | 12/2015 | Levin |
| 9,220,580 B2 | 12/2015 | Borovinskih et al. |
| 9,241,774 B2 | 1/2016 | Li et al. |
| 9,242,118 B2 | 1/2016 | Brawn |
| 9,261,358 B2 | 2/2016 | Atiya et al. |
| 9,277,972 B2 | 3/2016 | Brandt et al. |
| 9,336,336 B2 | 5/2016 | Deichmann et al. |
| 9,351,810 B2 | 5/2016 | Moon |
| 9,375,300 B2 | 6/2016 | Matov et al. |
| 9,403,238 B2 | 8/2016 | Culp |
| 9,408,743 B1 | 8/2016 | Wagner |
| 9,414,897 B2 | 8/2016 | Wu et al. |
| 9,433,476 B2 | 9/2016 | Khardekar et al. |
| 9,439,568 B2 | 9/2016 | Atiya et al. |
| 9,444,981 B2 | 9/2016 | Bellis et al. |
| 9,463,287 B1 | 10/2016 | Lorberbaum et al. |
| 9,492,243 B2 | 11/2016 | Kuo |
| 9,500,635 B2 | 11/2016 | Islam |
| 9,506,808 B2 | 11/2016 | Jeon et al. |

(56) References Cited

U.S. PATENT DOCUMENTS

| | | |
|---|---|---|
| 9,510,918 B2 | 12/2016 | Sanchez |
| 9,545,331 B2 | 1/2017 | Ingemarsson-Matzen |
| 9,566,132 B2 | 2/2017 | Stone-Collonge et al. |
| 9,584,771 B2 | 2/2017 | Mandelis et al. |
| 9,589,329 B2 | 3/2017 | Levin |
| 9,675,427 B2 | 6/2017 | Kopelman |
| 9,675,430 B2 | 6/2017 | Verker et al. |
| 9,693,839 B2 | 7/2017 | Atiya et al. |
| 9,730,769 B2 | 8/2017 | Chen et al. |
| 9,744,006 B2 | 8/2017 | Ross |
| 9,820,829 B2 | 11/2017 | Kuo |
| 9,830,688 B2 | 11/2017 | Levin |
| 9,844,421 B2 | 12/2017 | Moss et al. |
| 9,848,985 B2 | 12/2017 | Yang et al. |
| 9,861,451 B1 | 1/2018 | Davis |
| 9,936,186 B2 | 4/2018 | Jesenko et al. |
| 10,123,853 B2 | 11/2018 | Moss et al. |
| 10,154,889 B2 | 12/2018 | Chen et al. |
| 10,159,541 B2 | 12/2018 | Bindayel |
| 10,172,693 B2 | 1/2019 | Brandt et al. |
| 10,195,690 B2 | 2/2019 | Culp |
| 10,231,801 B2 | 3/2019 | Korytov et al. |
| 10,238,472 B2 | 3/2019 | Levin |
| 10,258,432 B2 | 4/2019 | Webber |
| 2001/0002310 A1 | 5/2001 | Chishti et al. |
| 2001/0032100 A1 | 10/2001 | Mahmud et al. |
| 2001/0038705 A1 | 11/2001 | Rubbert et al. |
| 2001/0041320 A1 | 11/2001 | Phan et al. |
| 2002/0004727 A1 | 1/2002 | Knaus et al. |
| 2002/0007284 A1 | 1/2002 | Schurenberg et al. |
| 2002/0010568 A1 | 1/2002 | Rubbert et al. |
| 2002/0015934 A1 | 2/2002 | Rubbert et al. |
| 2002/0025503 A1 | 2/2002 | Chapoulaud et al. |
| 2002/0026105 A1 | 2/2002 | Drazen |
| 2002/0028417 A1 | 3/2002 | Chapoulaud et al. |
| 2002/0035572 A1 | 3/2002 | Takatori et al. |
| 2002/0064752 A1 | 5/2002 | Durbin et al. |
| 2002/0064759 A1 | 5/2002 | Durbin et al. |
| 2002/0087551 A1 | 7/2002 | Hickey et al. |
| 2002/0107853 A1 | 8/2002 | Hofmann et al. |
| 2002/0188478 A1 | 12/2002 | Breeland et al. |
| 2002/0192617 A1 | 12/2002 | Phan et al. |
| 2003/0000927 A1 | 1/2003 | Kanaya et al. |
| 2003/0009252 A1 | 1/2003 | Pavlovskaia et al. |
| 2003/0019848 A1 | 1/2003 | Nicholas et al. |
| 2003/0021453 A1 | 1/2003 | Weise et al. |
| 2003/0035061 A1 | 2/2003 | Iwaki et al. |
| 2003/0057192 A1 | 3/2003 | Patel |
| 2003/0059736 A1 | 3/2003 | Lai et al. |
| 2003/0060532 A1 | 3/2003 | Subelka et al. |
| 2003/0068598 A1 | 4/2003 | Vallittu et al. |
| 2003/0095697 A1 | 5/2003 | Wood et al. |
| 2003/0096210 A1* | 5/2003 | Rubbert .............. A61C 7/00 433/24 |
| 2003/0101079 A1 | 5/2003 | McLaughlin |
| 2003/0103060 A1 | 6/2003 | Anderson et al. |
| 2003/0120517 A1 | 6/2003 | Eida et al. |
| 2003/0139834 A1 | 7/2003 | Nikolskiy et al. |
| 2003/0144886 A1 | 7/2003 | Taira |
| 2003/0172043 A1 | 9/2003 | Guyon et al. |
| 2003/0190575 A1 | 10/2003 | Hilliard |
| 2003/0192867 A1 | 10/2003 | Yamazaki et al. |
| 2003/0207224 A1 | 11/2003 | Lotte |
| 2003/0215764 A1 | 11/2003 | Kopelman et al. |
| 2003/0224311 A1 | 12/2003 | Cronauer |
| 2003/0224313 A1 | 12/2003 | Bergersen |
| 2003/0224314 A1 | 12/2003 | Bergersen |
| 2004/0002873 A1 | 1/2004 | Sachdeva |
| 2004/0009449 A1 | 1/2004 | Mah et al. |
| 2004/0013994 A1 | 1/2004 | Goldberg et al. |
| 2004/0019262 A1 | 1/2004 | Perelgut |
| 2004/0029078 A1 | 2/2004 | Marshall |
| 2004/0038168 A1 | 2/2004 | Choi et al. |
| 2004/0054304 A1 | 3/2004 | Raby |
| 2004/0054358 A1 | 3/2004 | Cox et al. |
| 2004/0058295 A1 | 3/2004 | Bergersen |
| 2004/0068199 A1 | 4/2004 | Echauz et al. |
| 2004/0078222 A1 | 4/2004 | Khan et al. |
| 2004/0080621 A1 | 4/2004 | Fisher et al. |
| 2004/0094165 A1 | 5/2004 | Cook |
| 2004/0107118 A1 | 6/2004 | Harnsberger et al. |
| 2004/0133083 A1 | 7/2004 | Comaniciu et al. |
| 2004/0152036 A1 | 8/2004 | Abolfathi |
| 2004/0158194 A1 | 8/2004 | Wolff et al. |
| 2004/0166463 A1 | 8/2004 | Wen et al. |
| 2004/0167646 A1 | 8/2004 | Jelonek et al. |
| 2004/0170941 A1 | 9/2004 | Phan et al. |
| 2004/0193036 A1 | 9/2004 | Zhou et al. |
| 2004/0197728 A1 | 10/2004 | Abolfathi et al. |
| 2004/0214128 A1 | 10/2004 | Sachdeva et al. |
| 2004/0219479 A1 | 11/2004 | Malin et al. |
| 2004/0220691 A1 | 11/2004 | Hofmeister et al. |
| 2004/0229185 A1 | 11/2004 | Knopp |
| 2004/0259049 A1 | 12/2004 | Kopelman et al. |
| 2005/0003318 A1 | 1/2005 | Choi et al. |
| 2005/0023356 A1 | 2/2005 | Wiklof et al. |
| 2005/0031196 A1 | 2/2005 | Moghaddam et al. |
| 2005/0037312 A1 | 2/2005 | Uchida |
| 2005/0038669 A1 | 2/2005 | Sachdeva et al. |
| 2005/0040551 A1 | 2/2005 | Biegler et al. |
| 2005/0042569 A1 | 2/2005 | Plan et al. |
| 2005/0042577 A1 | 2/2005 | Kvitrud et al. |
| 2005/0048433 A1 | 3/2005 | Hilliard |
| 2005/0074717 A1 | 4/2005 | Cleary et al. |
| 2005/0089822 A1 | 4/2005 | Geng |
| 2005/0100333 A1 | 5/2005 | Kerschbaumer et al. |
| 2005/0108052 A1 | 5/2005 | Omaboe |
| 2005/0131738 A1 | 6/2005 | Morris |
| 2005/0144150 A1 | 6/2005 | Ramamurthy et al. |
| 2005/0171594 A1 | 8/2005 | Machan et al. |
| 2005/0171630 A1 | 8/2005 | Dinauer et al. |
| 2005/0181333 A1 | 8/2005 | Karazivan et al. |
| 2005/0186524 A1 | 8/2005 | Abolfathi et al. |
| 2005/0186526 A1 | 8/2005 | Stewart et al. |
| 2005/0216314 A1 | 9/2005 | Secor |
| 2005/0233276 A1 | 10/2005 | Kopelman et al. |
| 2005/0239013 A1 | 10/2005 | Sachdeva |
| 2005/0244781 A1 | 11/2005 | Abels et al. |
| 2005/0244791 A1 | 11/2005 | Davis et al. |
| 2005/0271996 A1 | 12/2005 | Sporbert et al. |
| 2006/0056670 A1 | 3/2006 | Hamadeh |
| 2006/0057533 A1 | 3/2006 | McGann |
| 2006/0063135 A1 | 3/2006 | Mehl |
| 2006/0078842 A1 | 4/2006 | Sachdeva et al. |
| 2006/0084024 A1 | 4/2006 | Farrell |
| 2006/0093982 A1 | 5/2006 | Wen |
| 2006/0098007 A1 | 5/2006 | Rouet et al. |
| 2006/0099545 A1 | 5/2006 | Lia et al. |
| 2006/0099546 A1 | 5/2006 | Bergersen |
| 2006/0110698 A1 | 5/2006 | Robson |
| 2006/0111631 A1 | 5/2006 | Kelliher et al. |
| 2006/0115785 A1 | 6/2006 | Li et al. |
| 2006/0137813 A1 | 6/2006 | Robrecht et al. |
| 2006/0147872 A1 | 7/2006 | Andreiko |
| 2006/0154198 A1 | 7/2006 | Durbin et al. |
| 2006/0154207 A1 | 7/2006 | Kuo |
| 2006/0173715 A1 | 8/2006 | Wang |
| 2006/0183082 A1 | 8/2006 | Quadling et al. |
| 2006/0188834 A1 | 8/2006 | Hilliard |
| 2006/0188848 A1 | 8/2006 | Tricca et al. |
| 2006/0194163 A1 | 8/2006 | Tricca et al. |
| 2006/0199153 A1 | 9/2006 | Liu et al. |
| 2006/0204078 A1 | 9/2006 | Orth et al. |
| 2006/0223022 A1 | 10/2006 | Solomon |
| 2006/0223023 A1 | 10/2006 | Lai et al. |
| 2006/0223032 A1 | 10/2006 | Fried et al. |
| 2006/0223342 A1 | 10/2006 | Borst et al. |
| 2006/0234179 A1 | 10/2006 | Wen et al. |
| 2006/0257815 A1 | 11/2006 | De Dominicis |
| 2006/0275729 A1 | 12/2006 | Fornoff |
| 2006/0275731 A1 | 12/2006 | Wen et al. |
| 2006/0275736 A1 | 12/2006 | Wen et al. |
| 2006/0277075 A1 | 12/2006 | Salwan |
| 2006/0290693 A1 | 12/2006 | Zhou et al. |

(56) References Cited

U.S. PATENT DOCUMENTS

| | | |
|---|---|---|
| 2006/0292520 A1 | 12/2006 | Dillon et al. |
| 2007/0031775 A1 | 2/2007 | Andreiko |
| 2007/0046865 A1 | 3/2007 | Umeda et al. |
| 2007/0053048 A1 | 3/2007 | Kumar et al. |
| 2007/0054237 A1 | 3/2007 | Neuschafer |
| 2007/0065768 A1 | 3/2007 | Nadav |
| 2007/0087300 A1 | 4/2007 | Willison et al. |
| 2007/0087302 A1 | 4/2007 | Reising et al. |
| 2007/0106138 A1 | 5/2007 | Beiski et al. |
| 2007/0122592 A1 | 5/2007 | Anderson et al. |
| 2007/0128574 A1 | 6/2007 | Kuo et al. |
| 2007/0141525 A1 | 6/2007 | Cinader, Jr. |
| 2007/0141526 A1 | 6/2007 | Eisenberg et al. |
| 2007/0143135 A1 | 6/2007 | Lindquist et al. |
| 2007/0168152 A1 | 7/2007 | Matov et al. |
| 2007/0172112 A1 | 7/2007 | Paley et al. |
| 2007/0172291 A1 | 7/2007 | Yokoyama |
| 2007/0178420 A1 | 8/2007 | Keski-Nisula et al. |
| 2007/0183633 A1 | 8/2007 | Hoffmann |
| 2007/0184402 A1 | 8/2007 | Boutoussov et al. |
| 2007/0185732 A1 | 8/2007 | Hicks et al. |
| 2007/0192137 A1 | 8/2007 | Ombrellaro |
| 2007/0199929 A1 | 8/2007 | Rippl et al. |
| 2007/0215582 A1 | 9/2007 | Roeper et al. |
| 2007/0218422 A1 | 9/2007 | Ehrenfeld |
| 2007/0231765 A1 | 10/2007 | Phan et al. |
| 2007/0238065 A1 | 10/2007 | Sherwood et al. |
| 2007/0239488 A1 | 10/2007 | DeRosso |
| 2007/0263226 A1 | 11/2007 | Kurtz et al. |
| 2008/0013727 A1 | 1/2008 | Uemura |
| 2008/0020350 A1 | 1/2008 | Matov et al. |
| 2008/0045053 A1 | 2/2008 | Stadler et al. |
| 2008/0057461 A1 | 3/2008 | Cheng et al. |
| 2008/0057467 A1 | 3/2008 | Gittelson |
| 2008/0057479 A1 | 3/2008 | Grenness |
| 2008/0059238 A1 | 3/2008 | Park et al. |
| 2008/0090208 A1 | 4/2008 | Rubbert |
| 2008/0094389 A1 | 4/2008 | Rouet et al. |
| 2008/0113317 A1 | 5/2008 | Kemp et al. |
| 2008/0115791 A1 | 5/2008 | Heine |
| 2008/0118882 A1 | 5/2008 | Su |
| 2008/0118886 A1 | 5/2008 | Liang et al. |
| 2008/0141534 A1 | 6/2008 | Hilliard |
| 2008/0169122 A1 | 7/2008 | Shiraishi et al. |
| 2008/0171934 A1 | 7/2008 | Greenan et al. |
| 2008/0176448 A1 | 7/2008 | Muller et al. |
| 2008/0233530 A1 | 9/2008 | Cinader |
| 2008/0242144 A1 | 10/2008 | Dietz |
| 2008/0248443 A1 | 10/2008 | Chishti et al. |
| 2008/0254403 A1 | 10/2008 | Hilliard |
| 2008/0268400 A1 | 10/2008 | Moss et al. |
| 2008/0306724 A1 | 12/2008 | Kitching et al. |
| 2009/0029310 A1 | 1/2009 | Pumphrey et al. |
| 2009/0030290 A1 | 1/2009 | Kozuch et al. |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin |
| 2009/0075228 A1 | 3/2009 | Kaneko et al. |
| 2009/0087050 A1 | 4/2009 | Gandyra |
| 2009/0098502 A1 | 4/2009 | Andreiko |
| 2009/0099445 A1 | 4/2009 | Burger |
| 2009/0103579 A1 | 4/2009 | Ushimaru et al. |
| 2009/0105523 A1 | 4/2009 | Kassayan et al. |
| 2009/0136890 A1 | 5/2009 | Kang et al. |
| 2009/0136893 A1 | 5/2009 | Zegarelli |
| 2009/0148809 A1 | 6/2009 | Kuo et al. |
| 2009/0170050 A1 | 7/2009 | Marcus |
| 2009/0181346 A1 | 7/2009 | Orth |
| 2009/0191502 A1 | 7/2009 | Cao et al. |
| 2009/0210032 A1 | 8/2009 | Beiski et al. |
| 2009/0218514 A1 | 9/2009 | Klunder et al. |
| 2009/0246726 A1 | 10/2009 | Chelnokov et al. |
| 2009/0281433 A1 | 11/2009 | Saadat et al. |
| 2009/0286195 A1 | 11/2009 | Sears et al. |
| 2009/0298017 A1 * | 12/2009 | Boerjes ............... A61B 5/4547 433/214 |
| 2009/0305540 A1 | 12/2009 | Stadler et al. |
| 2009/0316966 A1 | 12/2009 | Marshall et al. |
| 2009/0317757 A1 | 12/2009 | Lemchen |
| 2010/0015565 A1 | 1/2010 | Carrillo Gonzalez et al. |
| 2010/0019170 A1 | 1/2010 | Hart et al. |
| 2010/0028825 A1 | 2/2010 | Lemchen |
| 2010/0045902 A1 | 2/2010 | Ikeda et al. |
| 2010/0062394 A1 | 3/2010 | Jones et al. |
| 2010/0068676 A1 | 3/2010 | Mason et al. |
| 2010/0086890 A1 | 4/2010 | Kuo |
| 2010/0138025 A1 | 6/2010 | Morton et al. |
| 2010/0142789 A1 | 6/2010 | Chang et al. |
| 2010/0145664 A1 | 6/2010 | Hultgren et al. |
| 2010/0145898 A1 | 6/2010 | Malfliet et al. |
| 2010/0152599 A1 | 6/2010 | DuHamel et al. |
| 2010/0165275 A1 | 7/2010 | Tsukamoto et al. |
| 2010/0167225 A1 | 7/2010 | Kuo |
| 2010/0179789 A1 | 7/2010 | Sachdeva et al. |
| 2010/0193482 A1 | 8/2010 | Ow et al. |
| 2010/0196837 A1 | 8/2010 | Farrell |
| 2010/0216085 A1 | 8/2010 | Kopelman |
| 2010/0217130 A1 | 8/2010 | Weinlaender |
| 2010/0231577 A1 | 9/2010 | Kim et al. |
| 2010/0268363 A1 | 10/2010 | Karim et al. |
| 2010/0268515 A1 | 10/2010 | Vogt et al. |
| 2010/0279243 A1 | 11/2010 | Cinader et al. |
| 2010/0280798 A1 | 11/2010 | Pattijn |
| 2010/0281370 A1 | 11/2010 | Rohaly et al. |
| 2010/0303316 A1 | 12/2010 | Bullis et al. |
| 2010/0312484 A1 | 12/2010 | DuHamel et al. |
| 2010/0327461 A1 | 12/2010 | Co et al. |
| 2011/0007920 A1 | 1/2011 | Abolfathi et al. |
| 2011/0012901 A1 | 1/2011 | Kaplanyan |
| 2011/0045428 A1 | 2/2011 | Boltunov et al. |
| 2011/0056350 A1 | 3/2011 | Gale et al. |
| 2011/0065060 A1 | 3/2011 | Teixeira et al. |
| 2011/0081625 A1 | 4/2011 | Fuh |
| 2011/0091832 A1 | 4/2011 | Kim et al. |
| 2011/0102549 A1 | 5/2011 | Takahashi |
| 2011/0102566 A1 | 5/2011 | Zakian et al. |
| 2011/0104630 A1 | 5/2011 | Matov et al. |
| 2011/0136072 A1 | 6/2011 | Li et al. |
| 2011/0136090 A1 | 6/2011 | Kazemi |
| 2011/0143673 A1 | 6/2011 | Landesman et al. |
| 2011/0159452 A1 | 6/2011 | Huang |
| 2011/0164810 A1 | 7/2011 | Zang et al. |
| 2011/0207072 A1 | 8/2011 | Schiemann |
| 2011/0212420 A1 | 9/2011 | Vuillemot |
| 2011/0220623 A1 | 9/2011 | Beutler |
| 2011/0235045 A1 | 9/2011 | Koerner et al. |
| 2011/0269092 A1 | 11/2011 | Kuo et al. |
| 2011/0316994 A1 | 12/2011 | Lemchen |
| 2012/0028210 A1 | 2/2012 | Hegyi et al. |
| 2012/0029883 A1 | 2/2012 | Heinz et al. |
| 2012/0040311 A1 | 2/2012 | Nilsson |
| 2012/0064477 A1 | 3/2012 | Schmitt |
| 2012/0081786 A1 | 4/2012 | Mizuyama et al. |
| 2012/0086681 A1 | 4/2012 | Kim et al. |
| 2012/0115107 A1 | 5/2012 | Adams |
| 2012/0129117 A1 | 5/2012 | McCance |
| 2012/0147912 A1 | 6/2012 | Moench et al. |
| 2012/0150494 A1 | 6/2012 | Anderson et al. |
| 2012/0166213 A1 | 6/2012 | Arnone et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |
| 2013/0029284 A1 | 1/2013 | Teasdale |
| 2013/0081272 A1 | 4/2013 | Johnson et al. |
| 2013/0089828 A1 | 4/2013 | Borovinskih et al. |
| 2013/0095446 A1 | 4/2013 | Andreiko et al. |
| 2013/0103176 A1 | 4/2013 | Kopelman et al. |
| 2013/0110469 A1 | 5/2013 | Kopelman |
| 2013/0150689 A1 | 6/2013 | Shaw-Klein |
| 2013/0163627 A1 | 6/2013 | Seurin et al. |
| 2013/0201488 A1 | 8/2013 | Ishihara |
| 2013/0204599 A1 | 8/2013 | Matov et al. |

(56) References Cited

U.S. PATENT DOCUMENTS

| | | |
|---|---|---|
| 2013/0209952 A1 | 8/2013 | Kuo et al. |
| 2013/0235165 A1* | 9/2013 | Gharib .................. G06T 7/593 |
| | | 348/50 |
| 2013/0252195 A1 | 9/2013 | Popat |
| 2013/0266326 A1 | 10/2013 | Joseph et al. |
| 2013/0278396 A1 | 10/2013 | Kimmel |
| 2013/0280671 A1 | 10/2013 | Brawn et al. |
| 2013/0286174 A1 | 10/2013 | Urakabe |
| 2013/0293824 A1 | 11/2013 | Yoneyama et al. |
| 2013/0323664 A1 | 12/2013 | Parker |
| 2013/0323671 A1 | 12/2013 | Dillon et al. |
| 2013/0323674 A1 | 12/2013 | Hakomori et al. |
| 2013/0325431 A1 | 12/2013 | See et al. |
| 2013/0337412 A1 | 12/2013 | Kwon |
| 2014/0061974 A1 | 3/2014 | Tyler |
| 2014/0081091 A1 | 3/2014 | Abolfathi et al. |
| 2014/0093160 A1 | 4/2014 | Porikli et al. |
| 2014/0106289 A1 | 4/2014 | Kozlowski |
| 2014/0120493 A1 | 5/2014 | Levin |
| 2014/0122027 A1 | 5/2014 | Andreiko et al. |
| 2014/0136222 A1 | 5/2014 | Arnone et al. |
| 2014/0142902 A1 | 5/2014 | Chelnokov et al. |
| 2014/0178829 A1 | 6/2014 | Kim |
| 2014/0265034 A1 | 9/2014 | Dudley |
| 2014/0272774 A1 | 9/2014 | Dillon et al. |
| 2014/0280376 A1 | 9/2014 | Kuo |
| 2014/0294273 A1 | 10/2014 | Jaisson |
| 2014/0313299 A1 | 10/2014 | Gebhardt et al. |
| 2014/0329194 A1 | 11/2014 | Sachdeva et al. |
| 2014/0342301 A1 | 11/2014 | Fleer et al. |
| 2014/0350354 A1 | 11/2014 | Stenzler et al. |
| 2014/0363778 A1 | 12/2014 | Parker |
| 2015/0002649 A1 | 1/2015 | Nowak et al. |
| 2015/0004553 A1 | 1/2015 | Li et al. |
| 2015/0021210 A1 | 1/2015 | Kesling |
| 2015/0079531 A1 | 3/2015 | Heine |
| 2015/0094564 A1 | 4/2015 | Tashman et al. |
| 2015/0097315 A1 | 4/2015 | DeSimone et al. |
| 2015/0097316 A1 | 4/2015 | DeSimone et al. |
| 2015/0102532 A1 | 4/2015 | DeSimone et al. |
| 2015/0132708 A1 | 5/2015 | Kuo |
| 2015/0140502 A1 | 5/2015 | Brawn et al. |
| 2015/0150501 A1 | 6/2015 | George et al. |
| 2015/0164335 A1 | 6/2015 | Van Der Poel et al. |
| 2015/0173856 A1 | 6/2015 | Iowe et al. |
| 2015/0182303 A1 | 7/2015 | Abraham et al. |
| 2015/0216626 A1 | 8/2015 | Ranjbar |
| 2015/0216716 A1 | 8/2015 | Anitua Aldecoa |
| 2015/0230885 A1 | 8/2015 | Wucher |
| 2015/0238280 A1 | 8/2015 | Wu et al. |
| 2015/0238283 A1 | 8/2015 | Tanugula et al. |
| 2015/0306486 A1 | 10/2015 | Logan et al. |
| 2015/0320320 A1 | 11/2015 | Kopelman et al. |
| 2015/0320532 A1 | 11/2015 | Matty et al. |
| 2015/0325044 A1 | 11/2015 | Lebovitz |
| 2015/0338209 A1 | 11/2015 | Knüttel |
| 2015/0351638 A1 | 12/2015 | Amato |
| 2015/0374469 A1 | 12/2015 | Konno et al. |
| 2016/0000332 A1 | 1/2016 | Atiya |
| 2016/0003610 A1 | 1/2016 | Lampert et al. |
| 2016/0022185 A1 | 1/2016 | Agarwal et al. |
| 2016/0042509 A1 | 2/2016 | Andreiko et al. |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0095668 A1 | 4/2016 | Kuo et al. |
| 2016/0100924 A1 | 4/2016 | Wilson et al. |
| 2016/0106520 A1 | 4/2016 | Borovinskih et al. |
| 2016/0120621 A1 | 5/2016 | Li et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0220105 A1 | 8/2016 | Durent |
| 2016/0220200 A1 | 8/2016 | Sandholm et al. |
| 2016/0225151 A1 | 8/2016 | Cocco et al. |
| 2016/0228213 A1 | 8/2016 | Tod et al. |
| 2016/0246936 A1 | 8/2016 | Kahn |
| 2016/0287358 A1 | 10/2016 | Nowak et al. |
| 2016/0296303 A1 | 10/2016 | Parker |
| 2016/0302885 A1 | 10/2016 | Matov et al. |
| 2016/0328843 A1 | 11/2016 | Graham et al. |
| 2016/0338799 A1 | 11/2016 | Wu et al. |
| 2016/0346063 A1 | 12/2016 | Schulhof et al. |
| 2016/0367188 A1 | 12/2016 | Malik et al. |
| 2016/0367339 A1 | 12/2016 | Khardekar et al. |
| 2017/0007365 A1 | 1/2017 | Kopelman et al. |
| 2017/0007366 A1 | 1/2017 | Kopelman et al. |
| 2017/0007367 A1 | 1/2017 | Li et al. |
| 2017/0007368 A1 | 1/2017 | Boronkay |
| 2017/0020633 A1 | 1/2017 | Stone-Collonge et al. |
| 2017/0049311 A1 | 2/2017 | Borovinskih et al. |
| 2017/0049326 A1 | 2/2017 | Alfano et al. |
| 2017/0056131 A1 | 3/2017 | Alauddin et al. |
| 2017/0071705 A1 | 3/2017 | Kuo |
| 2017/0086943 A1 | 3/2017 | Mah |
| 2017/0100209 A1 | 4/2017 | Wen |
| 2017/0100212 A1 | 4/2017 | Sherwood et al. |
| 2017/0100213 A1 | 4/2017 | Kuo |
| 2017/0100214 A1 | 4/2017 | Wen |
| 2017/0105815 A1 | 4/2017 | Matov et al. |
| 2017/0135792 A1 | 5/2017 | Webber |
| 2017/0135793 A1 | 5/2017 | Webber et al. |
| 2017/0156821 A1 | 6/2017 | Kopelman et al. |
| 2017/0165032 A1 | 6/2017 | Webber et al. |
| 2017/0215739 A1 | 8/2017 | Miyasato |
| 2017/0258555 A1 | 9/2017 | Kopelman |
| 2017/0265970 A1 | 9/2017 | Verker |
| 2017/0319054 A1 | 11/2017 | Miller et al. |
| 2017/0319296 A1 | 11/2017 | Webber et al. |
| 2017/0325690 A1 | 11/2017 | Salah et al. |
| 2017/0340411 A1 | 11/2017 | Akselrod |
| 2017/0340415 A1 | 11/2017 | Choi et al. |
| 2018/0000563 A1 | 1/2018 | Shanjani et al. |
| 2018/0000565 A1 | 1/2018 | Shanjani et al. |
| 2018/0028063 A1 | 2/2018 | Elbaz et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2018/0071055 A1 | 3/2018 | Kuo |
| 2018/0096465 A1 | 4/2018 | Levin |
| 2018/0168788 A1 | 6/2018 | Fernie |
| 2018/0228359 A1 | 8/2018 | Meyer et al. |
| 2018/0318043 A1 | 11/2018 | Li et al. |
| 2018/0368944 A1 | 12/2018 | Sato et al. |
| 2019/0046296 A1 | 2/2019 | Kopelman et al. |
| 2019/0046297 A1 | 2/2019 | Kopelman et al. |
| 2019/0069975 A1 | 3/2019 | Cam et al. |
| 2019/0076216 A1 | 3/2019 | Moss et al. |
| 2019/0090983 A1 | 3/2019 | Webber et al. |

FOREIGN PATENT DOCUMENTS

| | | |
|---|---|---|
| AU | 5598894 A | 6/1994 |
| CA | 1121955 A1 | 4/1982 |
| CN | 1655732 A | 8/2005 |
| CN | 1655733 A | 8/2005 |
| CN | 102017658 A | 4/2011 |
| CN | 103889364 A | 6/2014 |
| CN | 204092220 U | 1/2015 |
| CN | 105496575 A | 4/2016 |
| CN | 105997274 A | 10/2016 |
| DE | 2749802 A1 | 5/1978 |
| DE | 3526198 A1 | 2/1986 |
| DE | 4207169 A1 | 9/1993 |
| DE | 69327661 T2 | 7/2000 |
| DE | 102005043627 A1 | 3/2007 |
| DE | 202010017014 U1 | 3/2011 |
| DE | 102011051443 A1 | 1/2013 |
| DE | 202012011899 U1 | 1/2013 |
| DE | 102014225457 A1 | 6/2016 |
| EP | 0428152 A1 | 5/1991 |
| EP | 490848 A2 | 6/1992 |

(56) References Cited

FOREIGN PATENT DOCUMENTS

| | | |
|---|---|---|
| EP | 541500 A1 | 5/1993 |
| EP | 714632 B1 | 5/1997 |
| EP | 774933 B1 | 12/2000 |
| EP | 731673 B1 | 5/2001 |
| EP | 1941843 A2 | 7/2008 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| EP | 2848229 A1 | 3/2015 |
| ES | 463897 A1 | 1/1980 |
| ES | 2455066 A1 | 4/2014 |
| FR | 2369828 A1 | 6/1978 |
| FR | 2867377 A1 | 9/2005 |
| FR | 2930334 A1 | 10/2009 |
| GB | 1550777 A | 8/1979 |
| JP | 53058191 A | 5/1978 |
| JP | 4028359 A | 1/1992 |
| JP | 8508174 A | 9/1996 |
| JP | 09-19443 A | 1/1997 |
| JP | 2003245289 A | 9/2003 |
| JP | 2000339468 A | 9/2004 |
| JP | 2005527320 A | 9/2005 |
| JP | 2005527321 A | 9/2005 |
| JP | 2006043121 A | 2/2006 |
| JP | 2007151614 A | 6/2007 |
| JP | 2007260158 A | 10/2007 |
| JP | 2007537824 A | 12/2007 |
| JP | 2008067732 A | 3/2008 |
| JP | 2008523370 A | 7/2008 |
| JP | 04184427 B1 | 11/2008 |
| JP | 2009000412 A | 1/2009 |
| JP | 2009018173 A | 1/2009 |
| JP | 2009078133 A | 4/2009 |
| JP | 2009101386 A | 5/2009 |
| JP | 2009205330 A | 9/2009 |
| JP | 2010017726 A | 1/2010 |
| JP | 2011087733 A | 5/2011 |
| JP | 2012045143 A | 3/2012 |
| JP | 2013007645 A | 1/2013 |
| JP | 2013192865 A | 9/2013 |
| JP | 201735173 A | 2/2017 |
| KR | 10-20020062793 A | 7/2002 |
| KR | 10-20070108019 A | 11/2007 |
| KR | 10-20090065778 A | 6/2009 |
| KR | 10-1266966 B1 | 5/2013 |
| KR | 10-2016-041632 A | 4/2016 |
| KR | 10-2016-0071127 A | 6/2016 |
| TW | 480166 B | 3/2002 |
| WO | WO91/004713 A1 | 4/1991 |
| WO | WO92/03102 A1 | 3/1992 |
| WO | WO94/010935 A1 | 5/1994 |
| WO | WO96/23452 A1 | 8/1996 |
| WO | WO98/032394 A1 | 7/1998 |
| WO | WO98/044865 A1 | 10/1998 |
| WO | WO01/08592 A1 | 2/2001 |
| WO | WO01/85047 A2 | 11/2001 |
| WO | WO2002/017776 A2 | 3/2002 |
| WO | WO2002/062252 A1 | 8/2002 |
| WO | WO02/095475 A1 | 11/2002 |
| WO | WO03/003932 A2 | 1/2003 |
| WO | WO2006/096558 A2 | 9/2006 |
| WO | WO2006/100700 A1 | 9/2006 |
| WO | WO2006/133548 A1 | 12/2006 |
| WO | WO2007/019709 A2 | 2/2007 |
| WO | WO2007/071341 A1 | 6/2007 |
| WO | WO2007/103377 A2 | 9/2007 |
| WO | WO2008/115654 A1 | 9/2008 |
| WO | WO2009/016645 A2 | 2/2009 |
| WO | 2009089129 A1 | 7/2009 |
| WO | WO2009/085752 A2 | 7/2009 |
| WO | WO2009/146788 A1 | 12/2009 |
| WO | WO2009/146789 A1 | 12/2009 |
| WO | WO2010/059988 A1 | 5/2010 |
| WO | WO2010/123892 A2 | 10/2010 |
| WO | 2012007003 A1 | 1/2012 |
| WO | WO2012/064684 A2 | 5/2012 |
| WO | WO2012/074304 A2 | 6/2012 |
| WO | WO2012/078980 A2 | 6/2012 |
| WO | WO2012/083968 A1 | 6/2012 |
| WO | WO2012/140021 A2 | 10/2012 |
| WO | WO2013/058879 A2 | 4/2013 |
| WO | WO2014/068107 A1 | 5/2014 |
| WO | WO2014/091865 A1 | 6/2014 |
| WO | WO2014/143911 A1 | 9/2014 |
| WO | WO2015/015289 A2 | 2/2015 |
| WO | WO2015/063032 A1 | 5/2015 |
| WO | WO2015/112638 A1 | 7/2015 |
| WO | WO2015/176004 A1 | 11/2015 |
| WO | WO2016/004415 A1 | 1/2016 |
| WO | WO2016/042393 A1 | 3/2016 |
| WO | WO2016/061279 A1 | 4/2016 |
| WO | WO2016/084066 A1 | 6/2016 |
| WO | WO2016/099471 A1 | 6/2016 |
| WO | WO2016/113745 A1 | 7/2016 |
| WO | WO2016/116874 A1 | 7/2016 |
| WO | WO2016/200177 A1 | 12/2016 |
| WO | WO2017/006176 A1 | 1/2017 |
| WO | WO2017/182654 A1 | 10/2017 |

OTHER PUBLICATIONS

Doruk et al.; The role of the headgear timer in extraoral co-operation; European Journal of Orthodontics; 26; pp. 289-291; Jun. 1, 2004.

Friedrich et al; Measuring system for in vivo recording of force systems in orthodontic treatment-concept and analysis of accuracy; J. Biomech.; 32(1); pp. 81-85; (Abstract Only) Jan. 1999.

Grest, Daniel; Marker-Free Human Motion Capture in Dynamic Cluttered Environments from a Single View-Point, PhD Thesis; 171 pages; Dec. 2007.

Invisalign; You were made to move. There's never been a better time to straighten your teeth with the most advanced clear aligner in the world'; Product webpage; 2 pages; retrieved from the internet (www.invisalign.com/) on Dec. 28, 2017.

Kumar et al.; Rapid maxillary expansion: A unique treatment modality in dentistry; J. Clin. Diagn. Res.; 5(4); pp. 906-911; Aug. 2011.

Sahm et al.; "Micro-Electronic Monitoring of Functional Appliance Wear"; Eur J Orthod.; 12(3); pp. 297-301; Aug. 1990.

Sahm; Presentation of a wear timer for the clarification of scientific questions in orthodontic orthopedics; Fortschritte der Kieferorthopadie; 51 (4); pp. 243-247; (Translation Included) Jul. 19990.

Schafer et al.; "Quantifying patient adherence during active orthodontic treatment with removable appliances using microelectronic wear-time documentation"; Eur J Orthod.; 37(1)pp. 1-8; doi:10.1093/ejo/cju012; Jul. 3, 2014.

Thera Mon; "Microsensor"; "2 pages"; retrieved from the interent (www.english.thera-mon.com/the-product/transponder/index.html); on Sep. 19, 2016.

Wikipedia; Palatal expansion; 3 pages; retrieved from the internet (https://en.wikipedia.org/wiki/Palatal_expansion) on Mar. 5, 2018.

Wireless Sensor Networks Magazine; Embedded Teeth for Oral Activity Recognition; 2 pages; retrievedon Sep. 19, 2016 from the internet (www.wsnmagazine.com/embedded-teeth/); Jul. 29, 2013.

Witt et al.; The wear-timing measuring device in orthodontics-cui bono? Reflections on the state-of-the-art in wear-timing measurement and compliance research in orthodontics; Fortschr Kieferorthop.; 52(3); pp. 117-125; (Translation Included) Jun. 1991.

Yamada et al.; Simulation of fan-beam type optical computed-tomography imaging of strongly scattering and weakly absorbing media; Applied Optics; 32(25); pp. 4808-4814; Sep. 1, 1993.

Carrier et al.; U.S. Appl. No. 15/803,718 entitled "Methods and apparatuses for dental images," filed Nov. 3, 2017.

Kuo; U.S. Appl. No. 15/829,504 entitled "Dental appliance features for speech enhancement," filed Dec. 1, 2017.

(56) References Cited

OTHER PUBLICATIONS

Atiya et al.; U.S. Appl. No. 15/859,010 entitled "Compact confocal dental scanning apparatus," filed Dec. 29, 2017.
Shanjani et al.; U.S. Appl. No. 15/831,159 entitled "Palatal expanders and methods of expanding a palate," filed Dec. 4, 2017.
Wu et al.; U.S. Appl. No. 15/831,262 entitled "Methods and apparatuses for customizing a rapid palatal expander," filed Dec. 4, 2017.
Grove et al.; U.S. Appl. No. 15/726,243 entitled "Interproximal reduction templates," filed Oct. 5, 2017.
Nedelcu, Robert G., et al., "Scanning Accuracy and Precision in 4 Intraoral Scanners: An In Vitro Comparison Based on 3-Dimensional Analysis," The Journal of Prosthetic Dentistry, vol. 112, Issue 6, Dec. 1, 2014, pp. 1461-1471.
Align Technology; Align technology announces new teen solution with introduction of invisalign teen with mandibular advancement; 2 pages; retrieved from the internet (http://investor.aligntech.com/static-files/eb4fa6bb-3e62-404f-b74d-32059366a01b); Mar. 6, 2017.
CSI Computerized Scanning and Imaging Facility; What is a maximum/minimum intensity projection (MIP/MinIP); 1 page; retrived from the Internet (http://csi.whoi.edu/content/what-maximumminimum-intensity-projection-mipminip); Jan. 4, 2010.
Di Muzio et al.; Minimum intensity projection (MinIP); 6 pages; retrieved from the internet (https://radiopaedia.org/articles/minimum-intensity-projection-minip) on Sep. 6, 2018.
Ellias et al.; Proteomic analysis of saliva identifies potential biorrarkers for orthodontic tooth movement; The Scientific World Journal; vol. 2012; Article ID 647240; dio:10.1100/2012/647240; 7 pages; (year of pub. sufficiently earlier than effective US filing date and any foreign priority date) 2012.
Florez-Moreno; Time-related changes in salivary levels of the osteotropic factors sRANKL and OPG through orthodontic tooth movement; American Journal of Orthodontics and Dentofacial Orthopedics; 143(1); pp. 92-100; Jan. 2013.
Vadapalli; Minimum intensity projection (MinIP) is a data visualization; 7 pages; retrieved from the internet (https://prezi.com/tdmttnmv2knw/minimum-intensity-projection-minip-is-a-data-visualization/) on Sep. 6; 2018.
Watson et al.; Pressures recorded at te denture base-mucosal surface interface in complete denture wearers; Journal of Oral Rehabilitation 14(6); pp. 575-589; Nov. 1987.
Wolf; Three-dimensional structure determination of semi-transparent objects from holographic data; Optics Communications; 1(4); pp. 153-156; Sep. 1969.
Riley et al.; U.S. Appl. No. 16/003,841 entitled Palatal expander with skeletal anchorage devices, filed Jun. 8, 2018.
Shanjani et al.; U.S. Appl. No. 16/019,037 entitled "Biosensor performance indicator for intraoral appliances," filed Jun. 26, 2018.
Sato et al.; U.S. Appl. No. 16/041,606 entitled "Palatal contour anchorage," filed Jul. 20, 2018.
Xue et al.; U.S. Appl. No. 16/010,087 entitled "Automatic detection of tooth type and eruption status," filed Jun. 15, 2018.
Sato et al.; U.S. Appl. No. 16/048,054 entitled "Optical coherence tomography for orthodontic aligners," filed Jul. 27, 2018.
Miller et al.; U.S. Appl. No. 16/038,088 entitled "Method and apparatuses for interactive ordering of dental aligners," filed Jul. 17, 2018.
Moalem et al.; U.S. Appl. No. 16/046,897 entitled Tooth shading, transparency and glazing, filed Jul. 26, 2018.
Nyukhtikov et al.; U.S. Appl. No. 15/998,883 entitled "Buccal corridor assessment and computation," filed Aug. 15, 2018.
Sirona Dental Systems GmbH, CEREC 3D, Manuel utiiisateur, Version 2.0X (in French); 114 pages; (English translation of table of contents included); (year of pub. sufficiently earlier than effective US filing date and any foreign priority date); 2003.
AADR. American Association for Dental Research; Summary of Activities; Los Angeles, CA; p. 195; Mar. 20-23,(year of pub. sufficiently earlier than effective US filING DATE and any foreign priority date) 1980.
Alcaniz et aL; An Advanced System for the Simulation and Planning of Orthodontic Treatments; Karl Heinz Hohne and Ron Kikinis (eds.); Visualization in Biomedical Computing, 4th Intl. Conf, VBC '96, Hamburg, Germany; Springer-Verlag; pp. 511-520; Sep. 22-25, 1996.
Alexander et al.; The DigiGraph Work Station Part 2 Clinical Management; J. Clin. Orthod.; pp. 402-407; (Author Manuscript); Jul. 1990.
Allesee Orthodontic Appliance: Important Tip About Wearing the Red White & Blue Active Clear Retainer System; Allesee Orthodontic Appliances—Pro Lab; 1 page; (year of pub. sufficiently earlier than effective US filing date and any foreign priority date); 1998.
Allesee Orthodontic Appliances: DuraClearTM; Porduct information; 1 page; (year of pub. sufficiently earlier than effective US filing date and any foreign priority date) 1997.
Allesee Orthodontic Appliances; The Choice Is Clear: Red, White & Blue . . . The Simple, Affordable, No-Braces Treatment; ( product information for doctors); retrieved from the internet (http://ormco.com/aoa/appliancesservices/RWB/doctorhtml); 5 pages on May 19, 2003.
Allesee Orthodontic Appliances; The Choice Is Clear: Red, White & Blue . . . The Simple, Affordable, No-Braces Treatment; p(roduct information), 6 pages; (year of pub. sufficiently earlier than effective US filing date and any foreign priority date) 2003.
Allesee Orthodontic Appliances; The Choice is Clear: Red, White & Blue . . . The Simple, Affordable, No-Braces Treatment;(Patient Information); retrieved from the internet (http://ormco.com/aoa/appliancesservices/RWB/patients.html); 2 pages on May 19, 2003.
Allesee Orthodontic Appliances; The Red, White & Blue Way to Improve Your Smile; (information for patients), 2 pages; (year of pub. sufficiently earlier than effective US filing date and any foreign priority date) 1992.
Allesee Orthodontic Appliances; You may be a candidate for this invisible no-braces treatment; product information for patients; 2 pages; (year of pub. sufficiently earlier than effective US filing date and any foreign priority date) 2002.
Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.
Altschuler et al.; Laser Electro-Optic System for Rapid Three-Dimensional (3D) Topographic Mapping of Surfaces; Optical Engineering; 20(6); pp. 953-961; Dec. 1981.
Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.
Altschuler; 3D Mapping of Maxillo-Facial Prosthesis; AADR Abstract #607; 2 pages total, (year of pub. sufficiently earlier than effective US filing date and any foreign priority date) 1980.
Andersson et al.; Clinical Results with Titanium Crowns Fabricated with Machine Duplication and Spark Erosion; Acta Odontologica Scandinavica; 47(5); pp. 279-286; Oct. 1989.
Andrews, The Six Keys to Optimal Occlusion Straight Wire, Chapter 3, L.A. Wells; pp. 13-24; (year of pub. sufficiently earlier than effective US filing date and any foreign priority date) 1989.
Barone et al.; Creation of 3D multi-body orthodontic models by using independent imaging sensors; Sensors; 13(2); pp. 2033-2050; Feb. 5, 2013.
Bartels et al.; An Introduction to Splines for Use in Computer Graphics and Geometric Modeling; Morgan Kaufmann Publishers; pp. 422-425 Jan. 1, 1987.
Baumrind et al, "Mapping the Skull in 3-D," reprinted from J. Calif. Dent. Assoc, 48(2), 11 pages; (year of pub. sufficiently earlier than effective US filing date and any foreign priority date) Fall Issue 1972.
Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.

(56) References Cited

OTHER PUBLICATIONS

Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.
Baumrind; Integrated Three-Dimensional Craniofacial Mapping: Background, Principles, and Perspectives; Seminars in Orthodontics; 7(4); pp. 223-232; Dec. 2001.
Begole et al.; A Computer System for the Analysis of Dental Casts; The Angle Orthodontist; 51(3); pp. 252-258; Jul. 1981.
Bernard et al; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988.
Bhatia et al.; A Computer-Aided Design for Orthognathic Surgery; British Journal of Oral and Maxillofacial Surgery; 22(4); pp. 237-253; Aug. 1, 1984.
Biggerstaff et al.; Computerized Analysis of Occlusion in the Postcanine Dentition; American Journal of Orthodontics; 61(3); pp. 245-254; Mar. 1972.
Biggerstaff; Computerized Diagnostic Setups and Simulations; Angle Orthodontist; 40(I); pp. 28-36; Jan. 1970.
Biostar Operation & Training Manual. Great Lakes Orthodontics, Ltd. 199 Fire Tower Drive,Tonawanda, New York. 14150-5890, 20 pages; (year of pub. sufficiently earlier than effective US filing date and any foreign priority date) 1990.
Blu et al.; Linear interpolation revitalized; IEEE Transactions on Image Processing; 13(5); pp. 710-719; May 2004.
Bourke, Coordinate System Transformation; 1 page; retrived from the internet (http://astronomy.swin.edu.au/˜ pbourke/prolection/coords) on Nov. 5, 2004; Jun. 1996.
Boyd et al.; Three Dimensional Diagnosis and Orthodontic Treatment of Complex Malocclusions With the Invisalipn Appliance; Seminars in Orthodontics; 7(4); pp. 274-293; Dec. 2001.
Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.
Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.
Burstone et al.; Precision Adjustment of the Transpalatal Lingual Arch: Computer Arch Form Predetermination; American Journal of Orthodontics; 79(2);pp. 115-133; Feb. 1981.
Burstone; Dr. Charles J. Burstone on The Uses of the Computer in Orthodontic Practice (Part 1); Journal of Clinical Orthodontics; 13(7); pp. 442-453; (interview); Jul. 1979.
Burstone; Dr. Charles J. Burstone on The Uses of the Computer in Orthodontic Practice (Part 2); journal of Clinical Orthodontics; 13(8); pp. 539-551 (interview); Aug. 1979.
Cardinal Industrial Finishes; Powder Coatings; 6 pages; retrieved from the internet (http://www.cardinalpaint.com) on Aug. 25, 2000.
Carnaghan, An Alternative to Holograms for the Portrayal of Human Teeth; 4th Int'l. Conf. on Holographic Systems, Components and Applications; pp. 228-231; Sep. 15, 1993.
Chaconas et al,; The DigiGraph Work Station, Part 1, Basic Concepts; Journal of Clinical Orthodontics; 24(6); pp. 360-367; (Author Manuscript); Jun. 1990.
Chafetz et al.; Subsidence of the Femoral Prosthesis, A Stereophotogrammetric Evaluation; Clinical Orthopaedics and Related Research; No. 201; pp. 60-67; Dec. 1985.
Chiappone; Constructing the Gnathologic Setup and Positioner; Journal of Clinical Orthodontics; 14(2); pp. 121-133; Feb. 1980.
Chishti et al.; U.S. Appl. No. 60/050,342 entitled "Procedure for moving teeth using a seires of retainers," filed Jun. 20, 1997.
Cottingham; Gnathologic Clear Plastic Positioner; American Journal of Orthodontics; 55(1); pp. 23-31; Jan. 1969.

Crawford; CAD/CAM in the Dental Office: Does It Work?; Canadian Dental Journal; 57(2); pp. 121-123 Feb. 1991.
Crawford; Computers in Dentistry: Part 1: CAD/CAM: The Computer Moves Chairside, Part 2: F. Duret' A Man With a Vision, Part 3: The Computer Gives New Vision—Literally, Part 4: Bytes 'N Bites The Computer Moves From the Front Desk to the Operatory; Canadian Dental Journal; 54(9); pp. 661-666 Sep. 1988.
Crooks; CAD/CAM Comes to USC; USC Dentistry; pp. 14-17; (year of pub. sufficiently earlier than effective US filing date and any foreign priority date) Spring 1990.
Cureton; Correcting Malaligned Mandibular Incisors with Removable Retainers; Journal of Clinical Orthodontics; 30(7); pp. 390-395; Jul. 1996.
Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.
Cutting et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.
DCS Dental AG; The CAD/CAM 'DCS Titan System' for Production of Crowns/Bridges; DSC Production; pp. 1-7; Jan. 1992.
Defranco et al.; Three-Dimensional Large Displacement Analysis of Orthodontic Appliances; Journal of Biomechanics; 9(12); pp. 793-801; Jan. 1976.
Dental Institute University of Zurich Switzerland; Program for International Symposium on Computer Restorations: State of the Art of the CEREC-Method; 2 pages; May 1991.
Dentrac Corporation; Dentrac document; pp. 4-13; (year of pub. sufficiently earlier than effective US filing date and any foreign priority date) 1992.
Dent-X; Dentsim . . . Dent-x's virtual reality 3-D training simulator . . . A revolution in dental education; 6 pages; retrieved from the internet (http://www.dent-x.com/DentSim.htm); on Sep. 24, 1998.
Doyle; Digital Dentistry; Computer Graphics World; pp. 50-52 andp. 54; Oct. 2000.
Dummer et al.; Computed Radiography Imaging Based on High-Density 670 nm VCSEL Arrays; International Society for Optics and Photonics; vol. 7557; p. 75570H; 7 pages; (Author Manuscript); Feb. 24, 2010.
Duret et al.; CAD/CAM Imaging in Dentistry; Current Opinion in Dentistry; 1(2); pp. 150-154; Apr. 1991.
Duret et al; CAD-CAM in Dentistry; Journal of the American Dental Association; 117(6); pp. 715-720; Nov. 1988.
Duret; The Dental CAD/CAM, General Description of the Project; Hennson International Product Brochure, 18 pages; Jan. 1986.
Duret; Vers Une Prosthese Informatisee; Tonus; 75(15); pp. 55-57; (English translation attached); 23 pages; Nov. 15, 1985.
Economides; The Microcomputer in the Orthodontic Office; Journal of Clinical Orthodontics; 13(11); pp. 767-772; Nov. 1979.
Elsasser; Some Observations on the History and Uses of the Kesling Positioner; American Journal of Orthodontics; 36(5); pp. 368-374; May 1, 1950.
English translation of Japanese Laid-Open Publication No. 63-11148 to inventor T. Ozukuri (Laid-Open on Jan. 18, 1998) pp. 1-7.
Faber et al.; Computerized Interactive Orthodontic Treatment Planning; American Journal of Orthodontics; 73(1); pp. 36-46; Jan. 1978.
Felton et al.; A Computerized Analysis of the Shape and Stability of Mandibular Arch Form; American Journal of Orthodontics and Dentofacial Orthopedics; 92(6); pp. 478-483; Dec. 1987.
Friede et al.; Accuracy of Cephalometric Prediction in Orthognathic Surgery; Journal of Oral and Maxillofacial Surgery; 45(9); pp. 754-760; Sep. 1987.
Futterling et al.; Automated Finite Element Modeling of a Human Mandible with Dental Implants; JS WSCG '98—Conference Program; 8 pages; retrieved from the Internet (https://dspace5.zcu.cz/bitstream/11025/15851/1/Strasser_98.pdf); on Aug. 21, 2018.
Gao et al.; 3-D element Generation for Multi-Connected Complex Dental and Mandibular Structure; IEEE Proceedings International Workshop in Medical Imaging and Augmented Reality; pp. 267-271; Jun. 12, 2001.

(56) References Cited

OTHER PUBLICATIONS

Gim-Alldent Deutschland, "Das DUX System: Die Technik," 3 pages; (English Translation Included); (year of pub. sufficiently earlier than effective US filing date and any foreign priority date); 2002.
Gottleib et al.; JCO Interviews Dr. James A. McNamura, Jr., on the Frankel Appliance: Part 2: Clinical 1-1 Management; Journal of Clinical Orthodontics; 16(6); pp. 390-407; retrieved from the internet (http://www.jco-online.com/archive/print_article.asp?Year=1982&Month=06&ArticleNum+); 21 pages; Jun. 1982.
Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.
Guess et al.; Computer Treatment Estimates in Orthodontics and Orthognathic Surgery; Journal of Clinical Orthodontics; 23(4); pp. 262-268; 11 pages; (Author Manuscript); Apr. 1989.
Heaven et al.; Computer-Based Image Analysis of Artificial Root Surface Caries; Abstracts of Papers #2094; Journal of Dental Research; 70:528; (Abstract Only); Apr. 17-21, 1991.
Highbeam Research; Simulating stress put on jaw. (ANSYS Inc.'s finite element analysis software); 2 pages; retrieved from the Internet (http://static.highbeam.eom/t/toolingampproduction/november011996/simulatingstressputonfa . . .); on Nov. 5, 2004.
Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Inclused); Feb. 1987.
Hoffmann et al.; Role of Cephalometry for Planning of Jaw Orthopedics and Jaw Surgery Procedures; Informatbnen, pp. 375-396; (English Abstract Included); Mar. 1991.
Hojjatie et al.; Three-Dimensional Finite Element Analysis of Glass-Ceramic Dental Crowns; Journal of Biomechanics; 23(11); pp. 1157-1166; Jan. 1990.
Huckins; CAD-CAM Generated Mandibular Model Prototype from MRI Data; AAOMS, p. 96; (Abstract Only); (year of pub. sufficiently earlier than effective US filing date and any foreign priority date) 1999.
JCO Interviews; Craig Andreiko , DDS, MS on the Elan and Orthos Systems; Interview by Dr. Larry W. White; Journal of Clinical Orthodontics; 28(8); pp. 459-468; 14 pages; (Author Manuscript); Aug. 1994.
JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.
Jerrold; The Problem, Electronic Data Transmission and the Law; American Journal of Orthodontics and Dentofacial Orthopedics; 113(4); pp. 478-479; 5 pages; (Author Manuscript); Apr. 1998.
Jones et al.; An Assessment of the Fit of a Parabolic Curve to Pre- and Post-Treatment Dental Arches; British Journal of Orthodontics; 16(2); pp. 85-93; May 1989.
Kamada et.al.; Case Reports on Tooth Positioners Using LTV Vinyl Silicone Rubber; J. Nihon University School of Dentistry; 26(1); pp. 11-29; (year of pub. sufficiently earlier than effective US filing date and any foreign priority date) 1984.
Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.
Kanazawa et al.; Three-Dimensional Measurements of the Occlusal Surfaces of Upper Molars in a Dutch Population; Journal of Dental Research; 63(11); pp. 1298-1301; Nov. 1984.
Kesling et al.; The Philosophy of the Tooth Positioning Appliance; American Journal of Orthodontics and Oral surgery; 31(6); pp. 297-304; Jun. 1945.
Kesling; Coordinating the Predetermined Pattern and Tooth Positioner with Conventional Treatment; American Journal of Orthodontics and Oral Surgery; 32(5); pp. 285-293; May 1946.

Kleeman et al.; The Speed Positioner; J. Clin. Orthod.; 30(12); pp. 673-680; Dec. 1996.
Kochanek; Interpolating Splines with Local Tension, Continuity and Bias Control; Computer Graphics; 18(3); pp. 33-41; Jan. 1, 1984.
Kunii et al.; Articulation Simulation for an Intelligent Dental Care System; Displays; 15(3); pp. 181-188; Jul. 1994.
Kuroda et al.; Three-Dimensional Dental Cast Analyzing System Using Laser Scanning; American Journal of Orthodontics and Dentofacial Orthopedics; 110(4); pp. 365-369; Oct. 1996.
Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.
Leinfelder et al.; A New Method for Generating Ceramic Restorations: a CAD-CAM System; Journal of the American Dental Association; 118(6); pp. 703-707; Jun. 1989.
Manetti et al.; Computer-Aided Cefalometry and New Mechanics in Orthodontics; Fortschr Kieferorthop; 44; pp. 370-376; 8 pages; (English Article Summary Included); (year of pub. sufficiently earlier than effective US filing date and any foreign priority date) 1983.
McCann; Inside the ADA; J. Amer. Dent. Assoc, 118:286-294; Mar. 1989.
McNamara et al.; Invisible Retainers; J. Clin Orthod.; pp. 570-578; 11 pages; (Author Manuscript); Aug. 1985.
McNamara et al.; Orthodontic and Orthopedic Treatment in the Mixed Dentition; Needham Press; pp. 347-353; Jan. 1993.
Moermann et al, Computer Machined Adhesive Porcelain Inlays: Margin Adaptation after Fatigue Stress; IADR Abstract 339; J. Dent. Res.; 66(a):763; (Abstract Only); (year of pub. sufficiently earlier than effective US filing date and any foreign priority date) 1987.
Moles; Correcting Mild Malalignments—As Easy As One, Two, Three; AOA/Pro Corner; 11(2); 2 pages; (year of pub. sufficiently earlier than effective US filing date and any foreign priority date) 2002.
Mormann et al.; Marginale Adaptation von adhasuven Porzellaninlays in vitro; Separatdruck aus:Schweiz. Mschr. Zahnmed.; 95; pp. 1118-1129; 8 pages; (Macine Translated English Abstract); (year of pub. sufficiently earlier than effective US filing date and any foreign priority date); 1985.
Nahoum; The Vacuum Formed Dental Contour Appliance; N. Y. State Dent. J.; 30(9); pp. 385-390; Nov. 1964.
Nash; CEREC CAD/CAM Inlays: Aesthetics and Durability in a Single Appointment; Dentistry Today; 9(8); pp. 20, 22-23 and 54; Oct. 1990.
Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.
Ogawa et al.; Mapping, profiling and clustering of pressure pain threshold (PPT) in edentulous oral muscosa; Journal of Dentistry; 32(3); pp. 219-228; Mar. 2004.
Ogimoto et al.; Pressure-pain threshold determination in the oral mucosa; Journal of Oral Rehabilitation; 29(7); pp. 620-626; Jul. 2002.
Paul et al.; Digital Documentation of Individual Human Jaw and Tooth Forms for Applications in Orthodontics; Oral Surgery and Forensic Medicine Proc. of the 24th Annual Conf. of the IEEE Industrial Electronics Society (IECON '98); vol. 4; pp. 2415-2418; Sep. 4, 1998.
Pinkham; Foolish Concept Propels Technology; Dentist, 3 pages, Jan./Feb. 1989.
Pinkham; Inventor's CAD/CAM May Transform Dentistry; Dentist; pp. 1 and 35, Sep. 1990.
Ponitz; Invisible retainers; Am. J. Orthod.; 59(3); pp. 266-272; Mar. 1971.
Procera Research Projects; Procera Research Projects 1993 ' Abstract Collection; 23 pages; (year of pub. sufficiently earlier than effective US filing date and any foreign priority date) 1993.
Proffit et al.; The first stage of comprehensive treatment alignment and leveling; Contemporary Orthodontics, 3rd Ed.; Chapter 16;

(56) References Cited

OTHER PUBLICATIONS

Mosby Inc.; pp. 534-537; (year of pub. sufficiently earlier than effective US filing date and any foreign priority date) 2000.
Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.
Raintree Essix & ARS Materials, Inc., Raintree Essix, Technical Magazine Table of contents and Essix Appliances, 7 pages; retrieved from the internet (http://www.essix.com/magazine/defaulthtml) on Aug. 13, 1997.
Redmond et al.; Clinical Implications of Digital Orthodontics; American Journal of Orthodontics and Dentofacial Orthopedics; 117(2); pp. 240-242; Feb. 2000.
Rekow et al.; CAD/CAM for Dental Restorations—Some of the Curious Challenges; IEEE Transactions on Biomedical Engineering; 38(4); pp. 314-318; Apr. 1991.
Rekow et al.; Comparison of Three Data Acquisition Techniques for 3-D Tooth Surface Mapping; Annual International Conference of the IEEE Engineering in Medicine and Biology Society; 13(1); pp. 344-345 (year of pub. sufficiently earlier than effective US filing date and any foreign priority date) 1991.
Rekow; A Review of the Developments in Dental CAD/CAM Systems; Current Opinion in Dentistry; 2; pp. 25-33; Jun. 1992.
Rekow; CAD/CAM in Dentistry: A Historical Perspective and View of the Future; Journal Canadian Dental Association; 58(4); pp. 283, 287-288; Apr. 1992.
Rekow; Computer-Aided Design and Manufacturing in Dentistry: A Review of the State of the Art; Journal of Prosthetic Dentistry; 58(4); pp. 512-516; Dec. 1987.
Rekow; Dental CAD-CAM Systems: What is the State of the Art?; The Journal of the American Dental Association; 122(12); pp. 43-48; Dec. 1991.
Rekow; Feasibility of an Automated System for Production of Dental Restorations, Ph.D. Thesis; Univ. of Minnesota, 250 pages, Nov. 1988.
Richmond et al.; The Development of the PAR Index (Peer Assessment Rating): Reliability and Validity.; The European Journal of Orthodontics; 14(2); pp. 125-139; Apr. 1992.
Richmond et al.; The Development of a 3D Cast Analysis System; British Journal of Orthodontics; 13(1); pp. 53-54; Jan. 1986.
Richmond; Recording the Dental Cast in Three Dimensions; American Journal of Orthodontics and Dentofacial Orthopedics; 92(3); pp. 199-206; Sep. 1987.
Rudge; Dental Arch Analysis: Arch Form, A Review of the Literature; The European Journal of Orthodontics; 3(4); pp. 279-284; Jan. 1981.
Sakuda et al.; Integrated Information-Processing System in Clinical Orthodontics: An Approach with Use of a Computer Network System; American Journal of Orthodontics and Dentofacial Orthopedics; 101(3); pp. 210-220; 20 pages; (Author Manuscript) Mar. 1992.
Schellhas et al.; Three-Dimensional Computed Tomography in Maxillofacial Surgical Planning; Archives of Otolaryngology—Head and Neck Surgery; 114(4); pp. 438-442; Apr. 1988.
Schroeder et al; Eds. The Visual Toolkit, Prentice Hall PTR, New Jersey; Chapters 6, 8 & 9, (pp. 153-210,309-354, and 355-428; (year of pub. sufficiently earlier than effective US filing date and any foreign priority date) 1998.
Shilliday; Minimizing finishing problems with the mini-positioner; American Journal of Orthodontics; 59(6); pp. 596-599; Jun. 1971.
Shimada et al.; Application of optical coherence tomography (OCT) for diagnosis of caries, cracks, and defects of restorations; Current Oral Health Reports; 2(2); pp. 73-80; Jun. 2015.
Siemens; CEREC—Computer-Reconstruction, High Tech in der Zahnmedizin; 15 pagesl; (Includes Machine Translation); (year of pub. sufficiently earlier than effective US filing date and any foreign priority date); 2004.
Sinclair; The Readers' Corner; Journal of Clinical Orthodontics; 26(6); pp. 369-372; 5 pages; retrived from the internet (http://www.jco-online.com/archive/print_article.asp?Year=1992&Month=06&ArticleNum=); Jun. 1992.
Stoll et al.; Computer-aided Technologies in Dentistry; Dtsch Zahna'rztl Z 45, pp. 314-322; (English Abstract Included); (year of pub. sufficiently earlier than effective US filing date and any foreign priority date) 1990.
Sturman; Interactive Keyframe Animation of 3-D Articulated Models; Proceedings Graphics Interface '84; vol. 86; pp. 35-40; May-Jun. 1984.
The American Heritage, Stedman's Medical Dictionary; Gingiva; 3 pages; retrieved from the interent (http://reference.com/search/search?q=gingiva) on Nov. 5, 2004.
The Dental Company Sirona: Cerc omnicam and cerec bluecam brochure: The first choice in every case; 8 pages; (year of pub. sufficiently earlier than effective US filing date and any foreign priority date) 2014.
Thorlabs; Pellin broca prisms; 1 page; retrieved from the internet (www.thorlabs.com); Nov. 30, 2012.
Tiziani et al.; Confocal principle for macro and microscopic surface and defect analysis; Optical Engineering; 39(1); pp. 32-39; Jan. 1, 2000.
Truax; Truax Clasp-Less(TM) Appliance System; The Functional Orthodontist; 9(5); pp. 22-24, 26-8; Sep.-Oct. 1992.
Tru-Tatn Orthodontic & Dental Supplies, Product Brochure, Rochester, Minnesota 55902, 16 pages; (year of pub. sufficiently earlier than effective US filing date and any foreign priority date) 1996.
U.S. Department of Commerce, National Technical Information Service, Holodontography: An Introduction to Dental Laser Holography; School of Aerospace Medicine Brooks AFB Tex; Mar. 1973, 40 pages; Mar. 1973.
U.S. Department of Commerce, National Technical Information Service; Automated Crown Replication Using Solid Photography SM; Solid Photography Inc., Melville NY,; 20 pages; Oct. 1977.
Van Der Linden et al.; Three-Dimensional Analysis of Dental Casts by Means of the Optocom; Journal of Dental Research; 51(4); p. 1100; Jul.-Aug. 1972.
Van Der Linden; A New Method to Determine Tooth Positions and Dental Arch Dimensions; Journal of Dental Research; 51(4); p. 1104; Jul.-Aug. 1972.
Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.
Van Hilsen et al.; Comparing potential early caries assessment methods for teledentistry; BMC Oral Health; 13(16); doi: 10.1186/1472-6831-13-16; 9 pages; Mar. 2013.
Varady et al.; Reverse Engineering of Geometric Models' An Introduction; Computer-Aided Design; 29(4); pp. 255-268; 20 pages; (Author Manuscript); Apr. 1997.
Verstreken et al.; An Image-Guided Planning System for Endosseous Oral Implants; IEEE Transactions on Medical Imaging; 17(5); pp. 842-852; Oct. 1998.
Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.
Warunek et.al.; Clinical Use of Silicone Elastomer Applicances; JCO; 23(10); pp. 694-700; Oct. 1989.
Wells; Application of the Positioner Appliance in Orthodontic Treatment; American Journal of Orthodontics; 58(4); pp. 351-366; Oct. 1970.
Williams; Dentistry and CAD/CAM: Another French Revolution; J. Dent. Practice Admin.; 4(1); pp. 2-5 Jan./Mar. 1987.
Williams; The Switzerland and Minnesota Developments in CAD/CAM; Journal of Dental Practice Administration; 4(2); pp. 50-55; Apr./Jun. 1987.
Wishan; New Advances in Personal Computer Applications for Cephalometric Analysis, Growth Prediction, Surgical Treatment Planning and Imaging Processing; Symposium: Computerized Facial Imaging in Oral and Maxilofacial Surgery; p. 5; Presented on Sep. 13, 1990.

(56) References Cited

OTHER PUBLICATIONS

WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.
Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.
Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filing date and any foreign priority date); 1988.
Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.
Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998,.
Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.
Yoshii; Research on a New Orthodontic Appliance: The Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.
Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.
Yoshii; Research on a New Orthodontic Appliance: The Dynamic Positioner (D.P.); III—The General Concept of the D.P. Method and Its Therapeutic Effect, Part 2. Skeletal Reversed Occlusion Case Reports; Nippon Dental Review; 458; pp. 112-129; 40 pages; (Author Manuscript); Dec. 1980.
Cramer et al.; U.S. Appl. No. 15/942,341 entitled "Orthodontic appliances including at least partially un-erupted teeth and method of forming them," filed Mar. 30, 2018.
Cramer; U.S. Appl. No. 15/937,569 entitled "Apparatuses and methods assisting in dental therapies," filed Mar. 27, 2018.
Dental Monitoring; Basics: How to put the cheek retractor?; 1 page (Screenshot); retrieved from the interenet (https://www.youtube.com/watch?v=6K1HXw4Kq3c); May 27, 2016.
Dental Monitoring; Dental monitoring tutorial; 1 page (Screenshot); retrieved from the internet (https:www.youtube.com/watch?v=Dbe3udOf9_c); Mar. 18, 2015.
Ecligner Selfie; Change your smile; 1 page (screenshot); retrieved from the internet (https:play.google.com/store/apps/details?id=parklict.ecligner); on Feb. 13, 2018.
Sobral De Agular et al.; The gingival crevicular fluid as a source of biomarkers to enhance efficiency of orthodontic and functional treatment of growing patients; Bio. Med. Research International; vol. 2017; 7 pages; Article ID 3257235; (year of pub. sufficiently earlier than effective US filing date and any foreign priority date) 2017.
Levin; U.S. Appl. No. 16/282,431 entitled "Estimating a surface texture of a tooth," filed Feb. 2, 2019.
Chen et al.; U.S. Appl. No. 16/223,019 entitled "Release agent receptacle," filed Dec. 17, 2018.
Bandodkar et al.; Self-healing inks for autonomous repair of printable electrochemical devices; Advanced Electronic Materials; 1(12); 5 pages; 1500289; Dec. 2015.
Jia et al.; Epidermal biofuel cells: energy harvesting from human perspiration; Angewandle Chemie International Edition; 52(28); pp. 7233-7236; Jul. 8, 2013.
Jia et al.; Wearable textile biofuel cells for powering electronics; Journal of Materials Chemistry A; 2(43); pp. 18184-18189; Oct. 14, 2014.
Kim et al.; Noninvasive alcohol monitoring using a wearable tatto-based iontophoretic-biosensing system; Acs Sensors; 1(8); pp. 1011-1019; Jul. 22, 2016.
Kim et al.; Non-invasive mouthguard biosensor for continuous salivary monitoring of metabolites; Analyst; 139(7); pp. 1632-1636; Apr. 7, 2014.
Kim et al.; Wearable salivary uric acid mouthguard biosensor with integrated wireless electronics; Biosensors and Bioelectronics; 74; pp. 1061-1068; 19 pages; (Author Manuscript); Dec. 2015.
Kumar et al.; Biomarkers in orthodontic tooth movement; Journal of Pharmacy Bioallied Sciences; 7(Suppl 2); pp. S325-S330; 12 pages; (Author Manuscript); Aug. 2015.
Windmiller et al.; Wearable electrochemical sensors and biosensors: a review; Electroanalysis; 25(1); pp. 29-46; Jan. 2013.
Zhou et al.; Bio-logic analysis of injury biomarker patterns in human serum samples; Talanta; 83(3); pp. 955-959; Jan. 15, 2011.
Zhou et al.; Biofuel cells for self-powered electrochemical biosensing and logic biosensing: A review; Electroanalysis; 24(2); pp. 197-209; Feb. 2012.
Kopelman et al.; U.S. Appl. No. 16/152,281 entitled "Intraoral appliances for sampling soft-tissue," filed Oct. 4, 2018.
Morton et al.; U.S. Appl. No. 16/177,067 entitled "Dental appliance having selective occlusal loading and controlled intercuspation," filed Oct. 31, 2018.
Akopov et al.; U.S. Appl. No. 16/178,491 entitled "Automatic treatment planning," filed Nov. 1, 2018.
Elbaz et al.; U.S. Appl. No. 16/198,488 entitled "Intraoral scanner with dental diagnostics capabilities," filed Nov. 21, 2018.
Elbaz et al.; U.S. Appl. No. 16/188,262 entitled "Intraoral scanner with dental diagnostics capabilities," filed Nov. 12, 2018.
O'Leary et al.; U.S. Appl. No. 16/195,701 entitled "Orthodontic retainers," filed Nov. 19, 2018.
Shanjani et al., U.S. Appl. No. 16/206,894 entitled "Sensors for monitoring oral appliances," filed Nov. 28, 2019.
Shanjani et al., U.S. Appl. No. 16/231,906 entitled "Augmented reality enhancements for dental practitioners." filed Dec. 24, 2018.
Kopleman et al., U.S. Appl. No. 16/220,381 entitled "Closed loop adaptive orthodontic treatment methods and apparatuses," filed Dec. 14, 2018.
Sabina et al., U.S. Appl. No. 16/258,516 entitled "Diagnostic Introral Scanning" filed Jan. 25, 2019.
Bernabe et al.; Are the lower incisors the best predictors for the unerupted canine and premolars sums? An analysis of peruvian sample; The Angle Orthodontist; 75(2); pp. 202-207; Mar. 2005.
Collins English Dictionary; Teeth (definition); 9 pages; retrieved from the internet (https:www.collinsdictionary.com/us/dictionary/english/teeth) on May 13, 2019.
dictionary.com; Plural (definition); 6 pages; retrieved from the internet (https://www.dictionary.com/browse/plural#) on May 13, 2019.
dictionary.com; Quadrant (definition); 6 pages; retrieved from the internet ( https://www.dictionary.com/browse/quadrant?s=t) on May 13, 2019.
Martinelli et al.; Prediction of lower permanent canine and premolars width by correlation methods; The Angle Orthodontist; 75(5); pp. 805-808; Sep. 2005.
Nourallah et al.; New regression equations for prediciting the size of unerupted canines and premolars in a contemporary population; The Angle Orthodontist; 72(3); pp. 216-221; Jun. 2002.
Paredes et al.; A new, accurate and fast digital method to predict unerupted tooth size; The Angle Orthodontist; 76(1); pp. 14-19; Jan. 2006.
beautyworlds.com; Virtual plastic surgery—beautysurge.com announces launch of cosmetic surgery digital imaging services; 5 pages; retrieved from the internet (http://www.beautyworlds.com/cosmossurgdigitalimagning.htm); Mar. 2004.
Berland; The use of smile libraries for cosmetic dentistry; Dental Tribunne: Asia pacfic Edition; pp. 16-18; Mar. 29, 2006.

(56) References Cited

OTHER PUBLICATIONS

Bookstein; Principal warps: Thin-plate splines and decomposition of deformations; IEEE Transactions on pattern analysis and machine intelligence; 11(6); pp. 567-585; Jun. 1989.
Cadent Inc.; OrthoCAD ABO user guide; 38 pages; Dec. 21, 2005.
Cadent Inc.; Reviewing and modifying an orthoCAD case; 4 pages; Feb. 14, 2005.
Daniels et al.; The development of the index of complexity outcome and need (ICON); British Journal of Orthodontics; 27(2); pp. 149-162; Jun. 2000.
Dentrix; Dentrix G3, new features; 2 pages; retrieved from the internet (http://www.dentrix.com/g3/new_features/index.asp); on Jun. 6, 2008.
Di Giacomo et al.; Clinical application of sterolithographic surgical guides for implant placement: Preliminary results; Journal Periodontolgy; 76(4); pp. 503-507; Apr. 2005.
Gansky; Dental data mining: potential pitfalls and practical issues; Advances in Dental Research; 17(1); pp. 109-114; Dec. 2003.
Geomagic; Dental reconstruction; 1 page; retrieved from the internet (http://geomagic.com/en/solutions/industry/detal_desc.php) on Jun. 6, 2008.
Gottschalk et al.; OBBTree: A hierarchical structure for rapid interference detection; 12 pages; (http://www.cs.unc.edu/?geom/OBB/OBBT.html); relieved from te internet (https://www.cse.iitk.ac.in/users/amit/courses/RMP/presentations/dslamba/presentation/sig96.pdf) on Apr. 25, 2019.
gpsdentaire.com; Get a realistic smile simulation in 4 steps with GPS; a smile management software; 10 pages; retrieved from the internet (http://www.gpsdentaire.com/en/preview/) on Jun. 6, 2008.
Karaman et al.; A practical method of fabricating a lingual retainer; Am. Journal of Orthodontic and Dentofacial Orthopedics; 124(3); pp. 327-330; Sep. 2003.
Mantzikos et al.; Case report: Forced eruption and implant site development; The Angle Orthodontist; 68(2); pp. 179-186; Apr. 1998.
Methot; Get the picture with a gps for smile design in 3 steps; Spectrum; 5(4); pp. 100-105; (year of pub. sufficiently earlier than effective US filing date and any foreign priority date) 2006.
OrthoCAD downloads; retrieved Jun. 27, 2012 from the internet (www.orthocad.com/download/downloads.asp); 2 pages; Feb. 14, 2005.
Page et al.; Validity and accuracy of a risk calculator in predicting periodontal disease; Journal of the American Dental Association; 133(5); pp. 569-576; May 2002.
Patterson Dental; Cosmetic imaging; 2 pages retrieved from the internet (http://patterson.eaglesoft.net/cnt_di_cosimg.html) on Jun. 6, 2008.
Rose et al.; The role of orthodontics in implant dentistry; British Dental Journal; 201(12); pp. 753-764; Dec. 23, 2006.
Rubin et al.; Stress analysis of the human tooth using a three-dimensional finite element model; Journal of Dental Research; 62(2); pp. 82-86; Feb. 1983.
Sarment et al.; Accuracy of implant placement with a sterolithographic surgical guide; journal of Oral and Maxillofacial Implants; 118(4); pp. 571-577; Jul. 2003.
Smalley; Implants for tooth movement: Determining implant location and orientation: Journal of Esthetic and Restorative Dentistry; 7(2); pp. 62-72; Mar. 1995.
Smart Technology; Smile library II; 1 page; retrieved from the internet (http://smart-technology.net/) on Jun. 6, 2008.
Smile-VISION_The smile-vision cosmetic imaging system; 2 pages; retrieved from the internet (http://www.smile-vision.net/cos_imaging.php) on Jun. 6, 2008.
Szeliski; Introduction to computer vision: Structure from motion; 64 pages; retrieved from the internet (http://robots.stanford.edu/cs223b05/notes/CS%20223-B%20L10%structurefrommotion1b.ppt, on Feb. 3, 2005.
Vevin et al.; Pose estimation of teeth through crown-shape matching; In Medical Imaging: Image Processing of International Society of Optics and Photonics; vol. 4684; pp. 955-965; May 9, 2002.
Video of DICOM to Surgical Guides; Can be viewed at <URL:https://youtu.be/47KtOmCEFQk; Published Apr. 4, 2016.
Virtual Orthodontics; Our innovative software; 2 pages; (http://www.virtualorthodontics.com/innovativesoftware.html); retrieved from the internet (https://web.archive.org/web/20070518085145/http://www.virtualorthodontics.com/innovativesoftware.html); (year of pub. sufficiently earlier than effective US filing date and any foreign priority date) 2005.
Wiedmann; According to the laws of harmony to find the right tooth shape with assistance of the computer; Digital Dental News; 2nd Vol.; pp. 0005-0008; (English Version Included); Apr. 2008.
Wong et al.; Computer-aided design/computer-aided manufacturing surgical guidance for placement of dental implants: Case report; Implant Dentistry; 16(2); pp. 123-130; Sep. 2007.
Wong et al.; The uses of orthodontic study models in diagnosis and treatment planning; Hong Knog Dental Journal; 3(2); pp. 107-115; Dec. 2006.
Yaltara Software; Visual planner; 1 page; retrieved from the internet (http://yaltara.com/vp/) on Jun. 6, 2008.
Zhang et al.; Visual speech features extraction for improved speech recognition; 2002 IEEE International conference on Acoustics, Speech and Signal Processing; vol. 2; 4 pages; May 13-17, 2002.
Culp; U.S. Appl. No. 16/236,220 entitled "Laser cutting," filed Dec. 28, 2018.
Culp; U.S. Appl. No. 16/265,287 entitled "Laser cutting," filed Feb. 1, 2019.
Arnone et al.; U.S. Appl. No. 16/235,449 entitled "Method and system for providing indexing and cataloguing of orthodontic related treatment profiles and options," filed Dec. 28, 2018.
Mason et al.; U.S. Appl. No. 16/374,648 entitled "Dental condition evaluation and treatment," filed Apr. 3, 2019.
Brandt et al.; U.S. Appl. No. 16/235,490 entitled "Dental wire attachment," filed Dec. 28, 2018.
Kou; U.S. Appl. No. 16/270,891 entitled "Personal data file," filed Feb. 8, 2019.
Farooq et al.; Relationship between tooth dimensions and malocclusion; JPMA: The Journal of the Pakistan Medical Association; 64(6); pp. 670-674; Jun. 2014.
Newcombe; DTAM: Dense tracking and mapping in real-time; 8 pages; retrieved from the internet (http://www.doc.ic.ac.uk/?ajd/Publications/newcombe_etal_iccv2011.pdf; on Dec. 2011.
ormco.com; Increasing clinical performance with 3D interactive treatment planning and patient-specific appliances; 8 pages; retrieved from the internet (http://www.konsident.com/wp-content/files_mf/1295385693http___ormco.com_index_cmsfilesystemaction_fileOrmcoPDF_whitepapers.pdf) on Feb. 27, 2019.
Sabina et al., U.S. Appl. No. 16/258,523 entitled "Diagnostic intraoral tracking" filed Jan. 25, 2019.
Sabina et al., U.S. Appl. No. 16/258,527 entitled "Diagnostic intraoral methods and apparatuses" filed Jan. 25, 2019.
Li et al.; U.S. Appl. No. 16/171,159 entitled "Alternative bite adjustment structures," filed Oct. 25, 2018.

\* cited by examiner

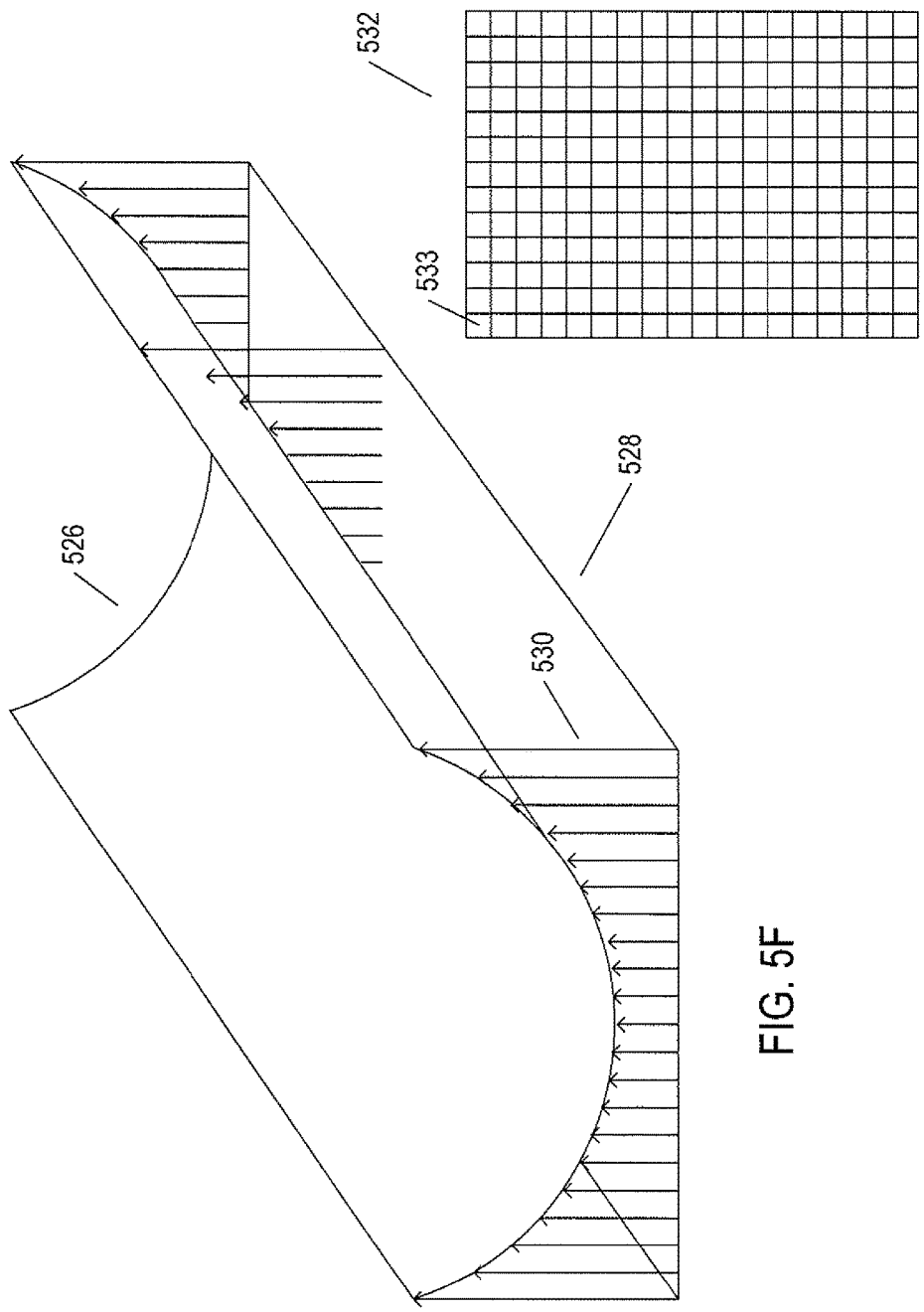

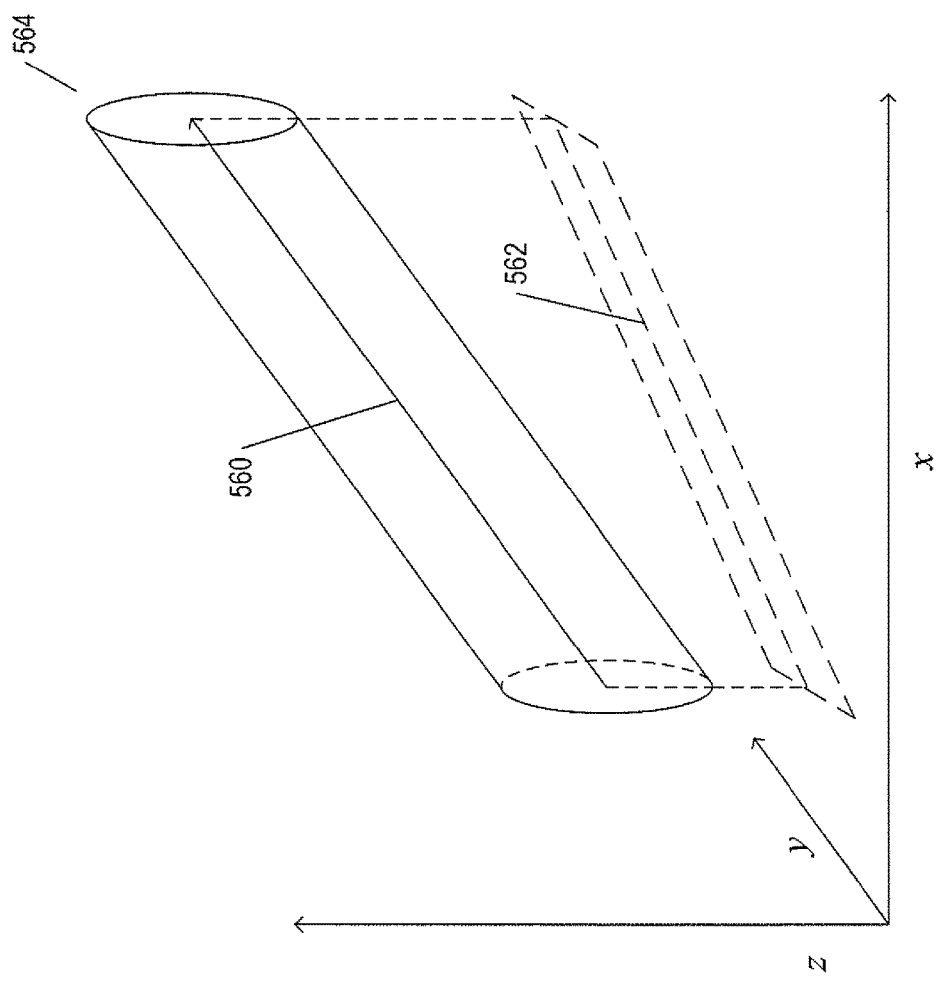

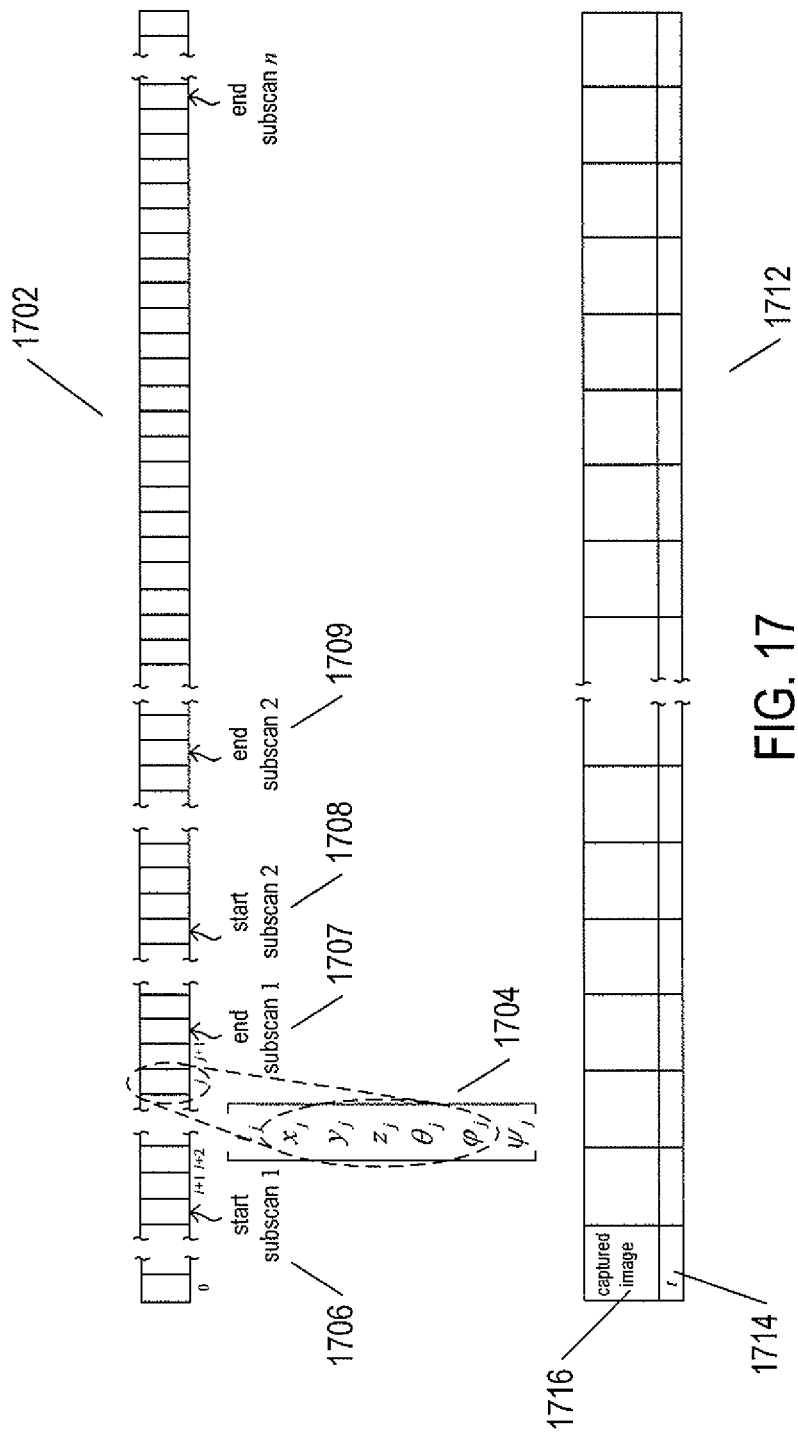

TRAINING METHOD AND SYSTEM FOR ORAL-CAVITY-IMAGING-AND-MODELING EQUIPMENT

CROSS-REFERENCE TO RELATED APPLICATION

This application claims the benefit of Provisional Application No. 62/108,263, filed Jan. 27, 2015.

TECHNICAL FIELD

The current document is directed to automated and semi-automated training methods and systems and, in particular, to methods and systems that train technicians to effectively employ oral-cavity-imaging-and-modeling systems.

BACKGROUND

Prior to the development of oral-cavity-imaging-and-modeling systems, dental practitioners employed mechanical-impression methods to create three-dimensional models of teeth and underlying tissue in order to facilitate fabrication of various types of prostheses, including crowns and bridges. The mechanical-impression technologies generally involved biting, by a patient, into a viscous, thixotropic material that retains an accurate impression of the patient's teeth and underlying tissue when the material is lifted off from the patient's teeth. The material may serve as a mold for casting a positive three-dimensional model of the patient's teeth and underlying gum tissue or as a mold for casting a prosthetic device. While mechanical-impression technologies have been used by dental practitioners for many decades, mechanical-impression technologies are associated with a variety of deficiencies, including a relatively large probability that the impression may be inadvertently altered or damaged during removal of the hardened, viscous, thixotropic material from the patient's teeth as well as during transportation of the impression to laboratories where positive three-dimensional models are cast and prostheses are fabricated. In addition, the procedure is time-consuming and unpleasant to many patients.

More recently, semi-automated oral-cavity-imaging-and-modeling systems have been developed to electronically create digital, three-dimensional models of teeth and underlying tissues from images of a patient's oral cavity captured by an electro-optical-mechanical endoscope, or wand, that is guided by a technician within a patient's oral cavity in order to collect a sufficient number of two-dimensional images from which a three-dimensional digital model of the patient's teeth and underlying tissues is computationally generated. The oral-cavity-imaging-and-modeling systems have proven to be faster, more accurate and robust, and more cost effective than mechanical-impression technologies. However, the efficiency and cost effectiveness of oral-cavity-imaging-and-modeling systems may significantly vary with respect to the experience and skill of the technicians who use the oral-cavity-imaging-and-modeling systems to generate three-dimensional models of patients' teeth and underlying tissues.

SUMMARY

The current document is directed to methods and systems that provide semi-automated and automated training to technicians who use oral-cavity-imaging-and-modeling systems to efficiently and accurately generate three-dimensional models of patients' teeth and underlying tissues. The three-dimensional models may be subsequently used for fabricating dental prostheses, treatment planning, monitoring the dental health of patients, providing simulations of proposed restorations, and for other dental-care-related uses. The training methods and systems are implemented either as subsystems within oral-cavity-imaging-and-modeling systems or as separate system in electronic communication oral-cavity-imaging-and-modeling systems. These training methods and systems use an already generated, digital, three-dimensional model of a portion of the oral cavity of a particular patient or of a physical model of a portion of an oral cavity to compute a temporal, translational, and rotational trajectory of an oral-cavity-imaging-and-modeling endoscope, or wand, during a training scan.

The temporal, translational, and rotational trajectory is used for a variety of different types of instruction and instructional feedback to facilitate training of technicians.

BRIEF DESCRIPTION OF THE DRAWINGS

FIGS. 5A-K illustrate characteristics of a wand trajectory during an imaging scan.

FIG. 17 illustrates two different data structures that are maintained by the training subsystem of an oral-cavity-imaging-and-modeling system during training sessions to facilitate the calculation and display of information by a training user interface and for other training purposes.

DETAILED DESCRIPTION

The current document is directed to automated and semi-automated methods, and systems that incorporate the methods, for training oral-cavity-imaging-and-modeling-equipment technicians to efficiently and accurately scan the oral cavities of patients in order to acquire accurate, three-dimensional digital models of patients' teeth and gum tissue. These automated and semi-automated methods employ, as subjects for training, either particular individuals for whom three-dimensional oral-cavity models have already been generated or physical models of teeth and tissue associated with already generated three-dimensional digital models. Because, during training, a technician collects images from either a patient or physical model associated with an already generated three-dimensional digital model, images captured during training can be used, along with the already generated three-dimensional model, to accurately determine the position and orientation of the image-capturing endoscope, or wand, as the wand is guided by the technician during a training scan in certain implementations. In other implementations, at least the spatial position of the wand can be estimated to a useful degree of accuracy, and, in still other implementations, both the spatial position and orientation of the wand can be estimated to a useful degree of accuracy. This information, in turn, provides the basis for many different types of automated and semi-automated instructional feedback and guidance.

Figure 1:
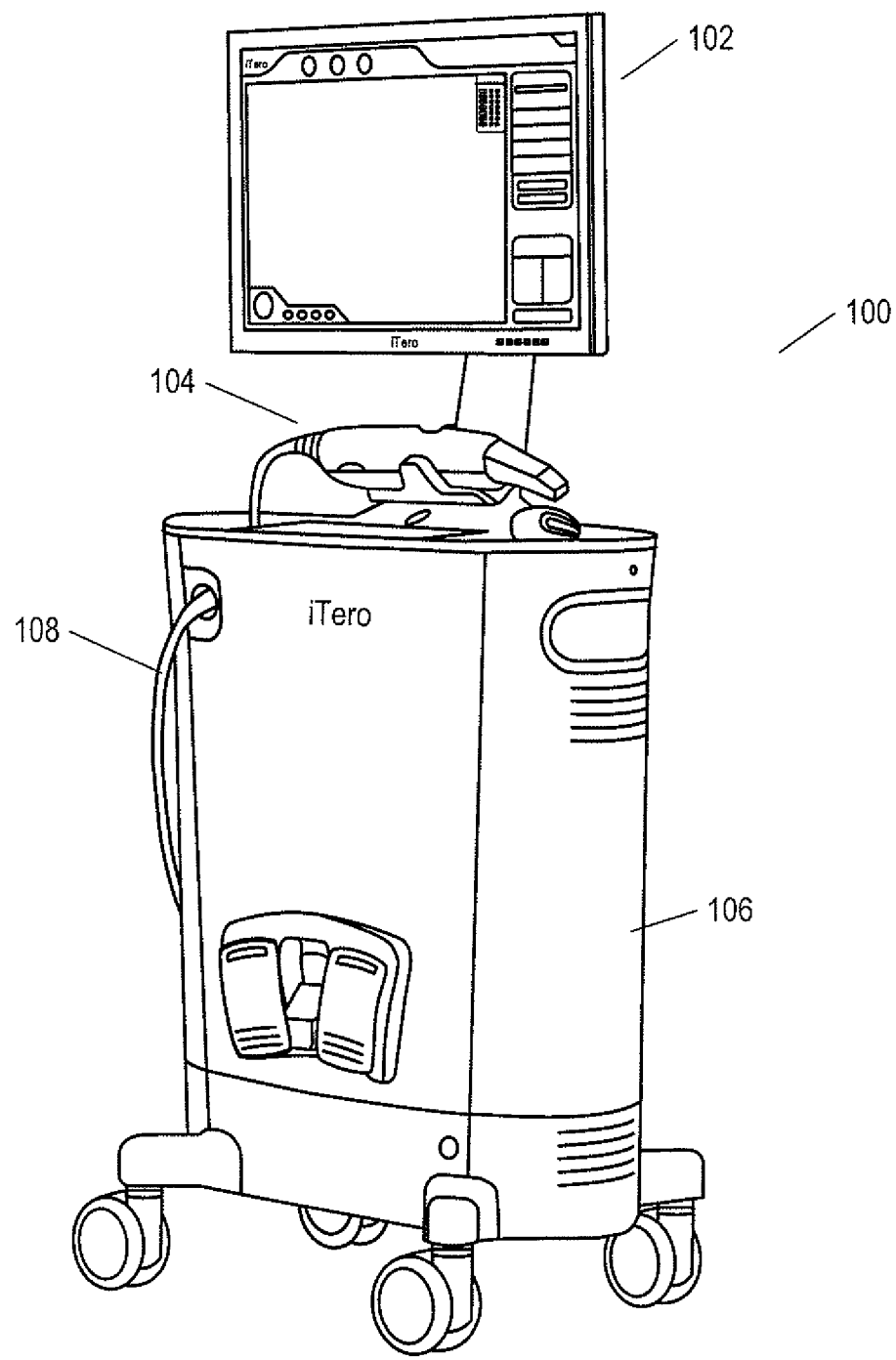
FIG. 1 shows one type of oral-cavity-imaging-and-modeling system.

FIG. 1 shows one type of oral-cavity-imaging-and-modeling system. The system 100 includes an electronic display screen 102, an endoscope 104, alternatively referred to as a "wand" or "optical wand," and a housing 106 that includes a processor-controlled computing system, a laser light source, imaging subsystems, and additional components. The wand 104 is connected to the components and subsystems within housing 106 by an electro-optical cable 108.

Figure 2:
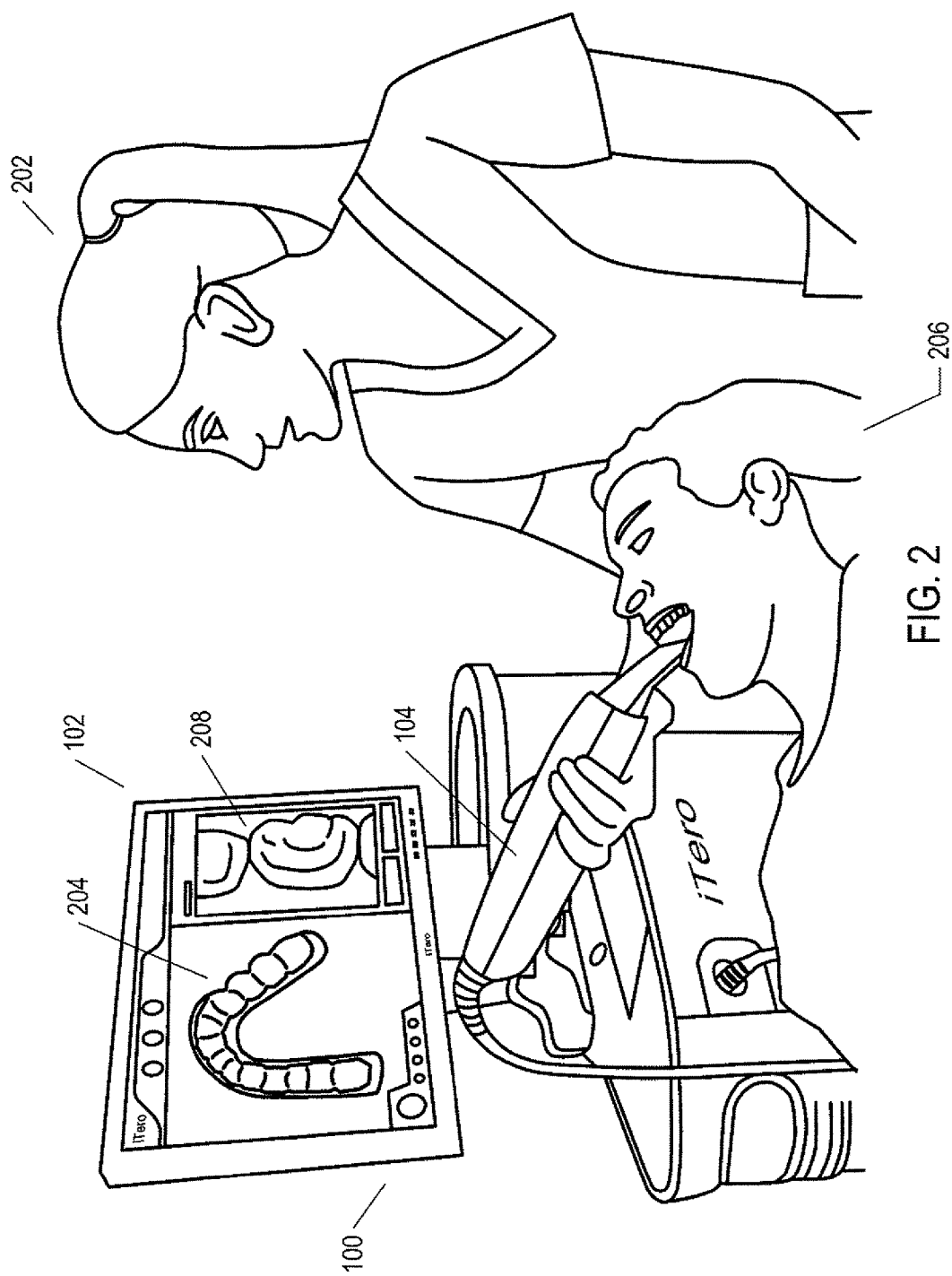
FIG. 2 shows an oral-cavity-imaging-and-modeling system being used by a technician to image the oral cavity of a patient.

FIG. 2 shows an oral-cavity-imaging-and-modeling system being used by a technician to image the oral cavity of a patient. As shown in FIG. 2, the technician 202 holds and guides the wand 104 within a patient's mouth in order to acquire images of the patient's teeth and underlying tissue which are then used, by the processor-controlled computing system within the oral-cavity-imaging-and-modeling system 100, to generate a three-dimensional, digital model of the patient's teeth and underlying gum tissue. The model 204, or a partial model, may be rendered for display on the display screen 102 for viewing both by the technician 202 and patient 206. In addition, selected images acquired by the system 208 may be concurrently displayed. Once the technician has completed a sufficient number of scans, guiding the wand along different trajectories and in different orientations, a sufficient number of different two-dimensional photographic and three-dimensional surface images have been acquired by the system to generate a complete three-dimensional digital model of a portion of the patient's oral cavity. The digital model is saved in one or more files that can be downloaded to remote systems, including systems in laboratories where prostheses are fabricated, and can be stored as part of the patient history for a variety of subsequent uses, including developing treatment plans, monitoring dental health over long periods of time, generating simulations of proposed prostheses and treatments, facilitating explanation of conditions and pathologies to patients, and for many other uses.

Figure 3:
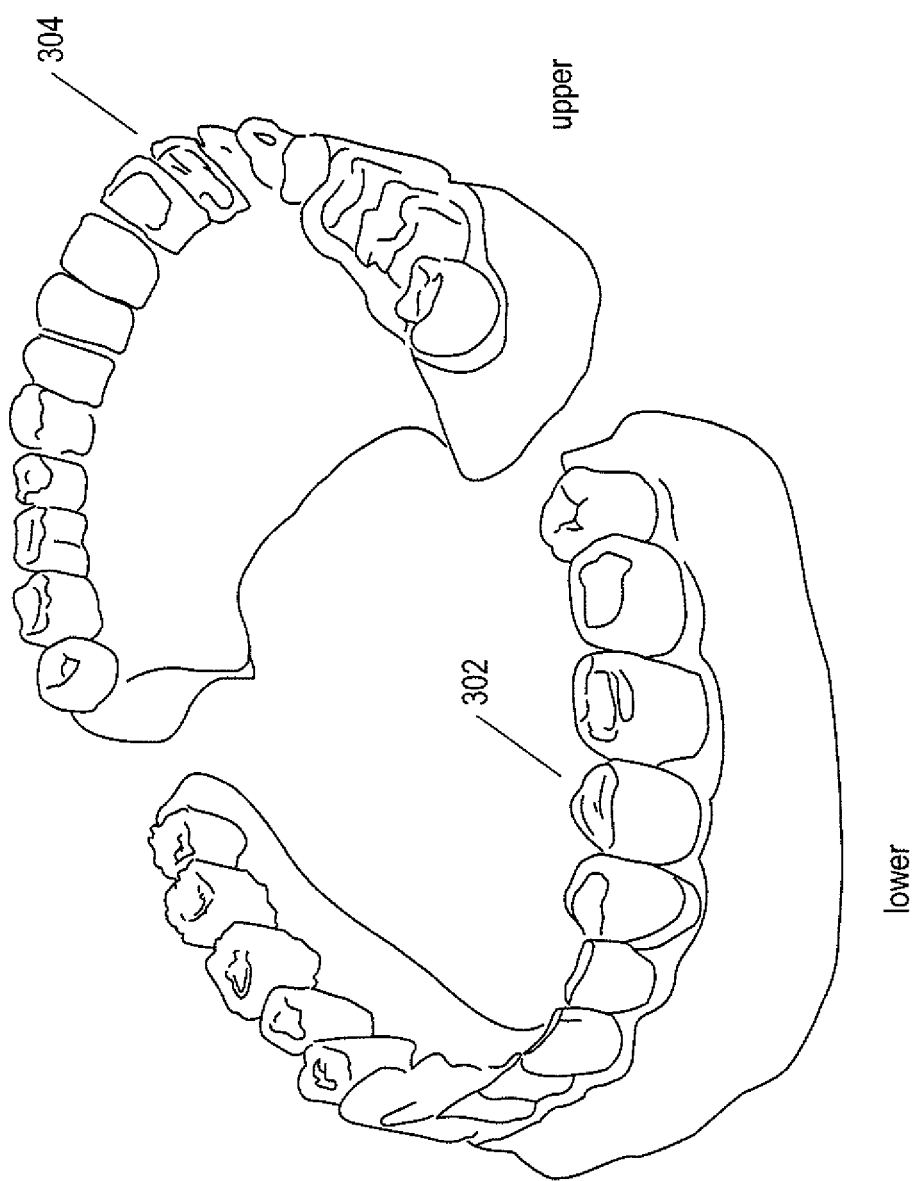
FIG. 3 illustrates lower and upper rows of teeth and underlying tissue.
Figure 4:
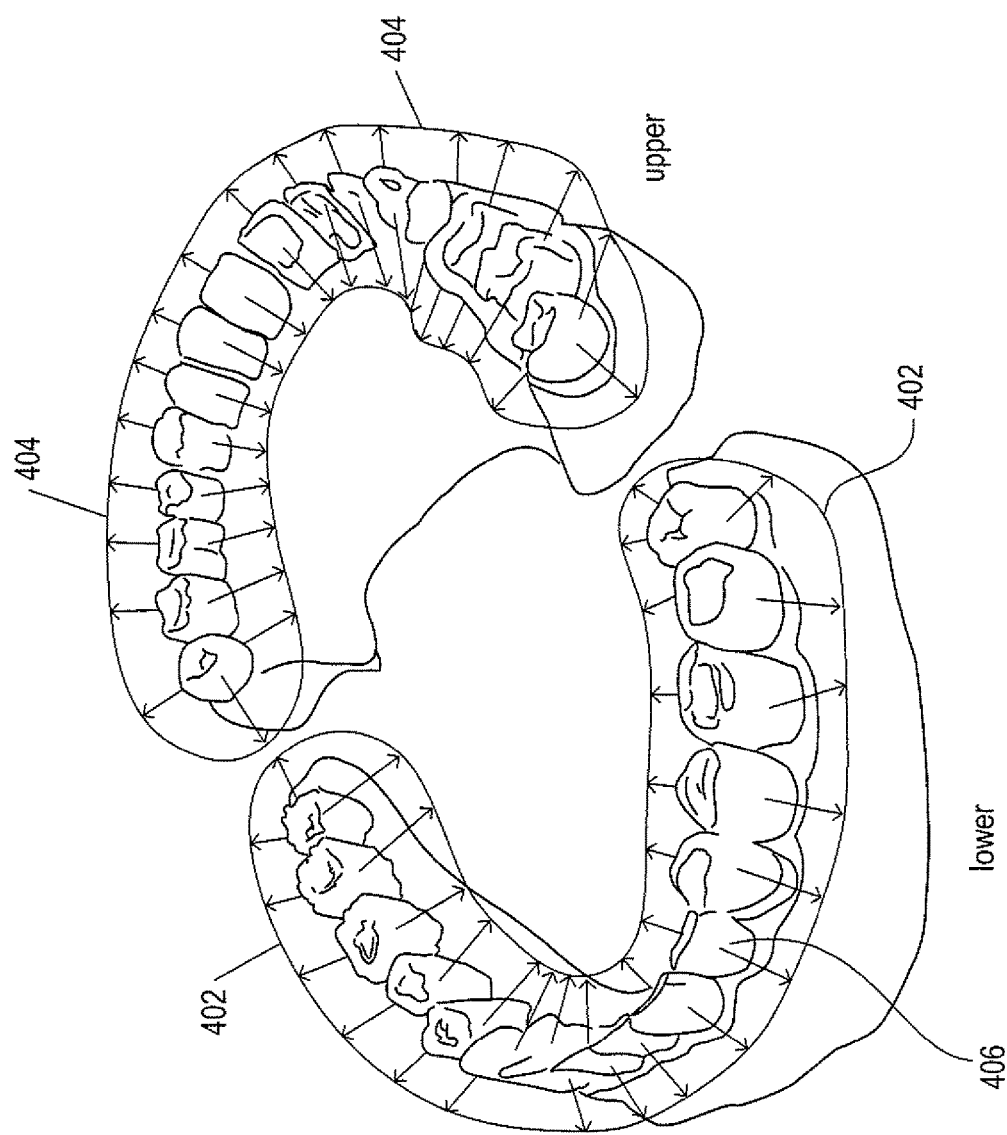
FIG. 4 illustrates one possible trajectory of a point on an image-collecting surface of an endoscope within the oral cavity of a patient during a scan of the lower and upper rows of teeth.

FIG. 3 illustrates lower and upper rows of teeth and underlying gum tissue. In FIG. 3, the lower row of teeth 302 and upper row of teeth 304 are arranged in a planar fashion, as if the jaw were able to rotate nearly 180 degrees. FIG. 4 illustrates one possible trajectory of a point on an image-collecting surface of an endoscope within the oral cavity of a patient during a scan of the lower and upper rows of teeth. A first scan of the lower row of teeth may follow the horseshoe-shaped trajectory indicated by curve 402 and a second scan of the upper row of teeth may follow a horseshoe-like trajectory 404. Small arrows, such as arrow 406, indicate the path of light from the closest point on the patient's teeth to a reference point on the endoscope, or wand. During the scanning operation, as discussed further below, images are captured by the endoscope at various positions along the trajectory to produce a sequence of images from which a three-dimensional digital model is computationally constructed. As discussed further below, the wand has a position in three-dimensional space as well as a rotational orientation, and thus each point on the trajectory may be described in terms of three spatial coordinates, three rotational angles, and an absolute time or an elapsed time relative to the starting time of the scan. There are many different possible coordinate systems that can be used for both spatial position and rotational orientation. In general, multiple scans may be needed to generate an accurate three-dimensional model, each scan having a distinct trajectory. At any given point in the trajectory, the wand can capture a two-dimensional image and can additionally determine the distance between imaged features and surfaces and the wand.

Figure 5A:
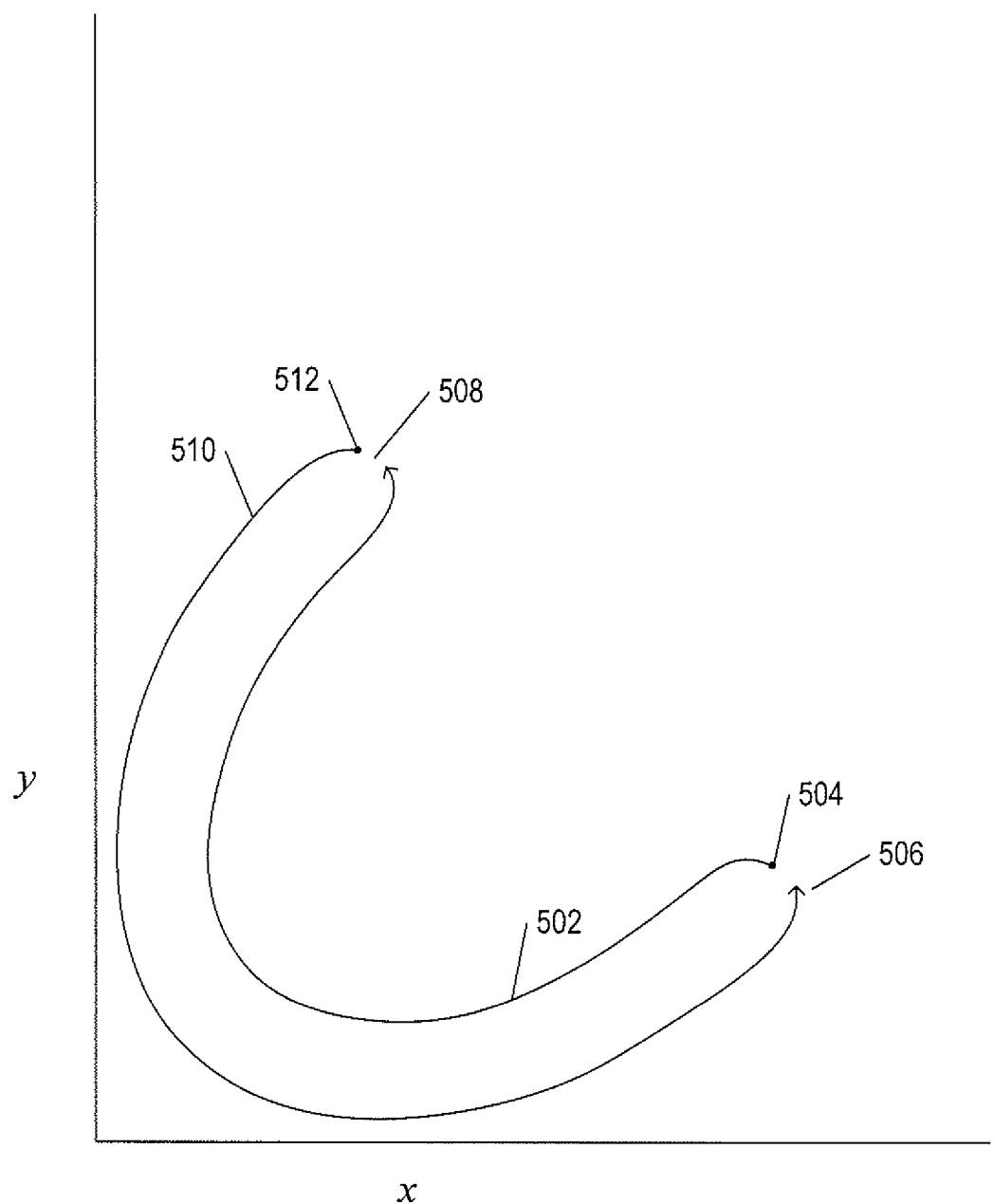

FIGS. 5A-K illustrate characteristics of a wand trajectory during an imaging scan. FIG. 5A shows a two-dimensional projection of the three-dimensional spatial component of two trajectories corresponding to two subscans of a row of teeth. The projection is carried out perpendicularly to the plane of the row of teeth discussed above with reference to FIGS. 3 and 4. A first subscan 502 starts at a point 504 at a first end 506 of the row of teeth and proceeds to the second, opposite end 508 of the row of teeth. The first subscan 502 is used to image the inner, or lingual, surfaces of the teeth in the row of teeth. A second subscan 510 begins at a point 512 at the second end of the row of teeth and proceeds back, in an opposite direction, to the first end 506 of the row of teeth. The second subscan 510 is used to image the exterior, or buccal, surfaces of the teeth.

Figure 5B:
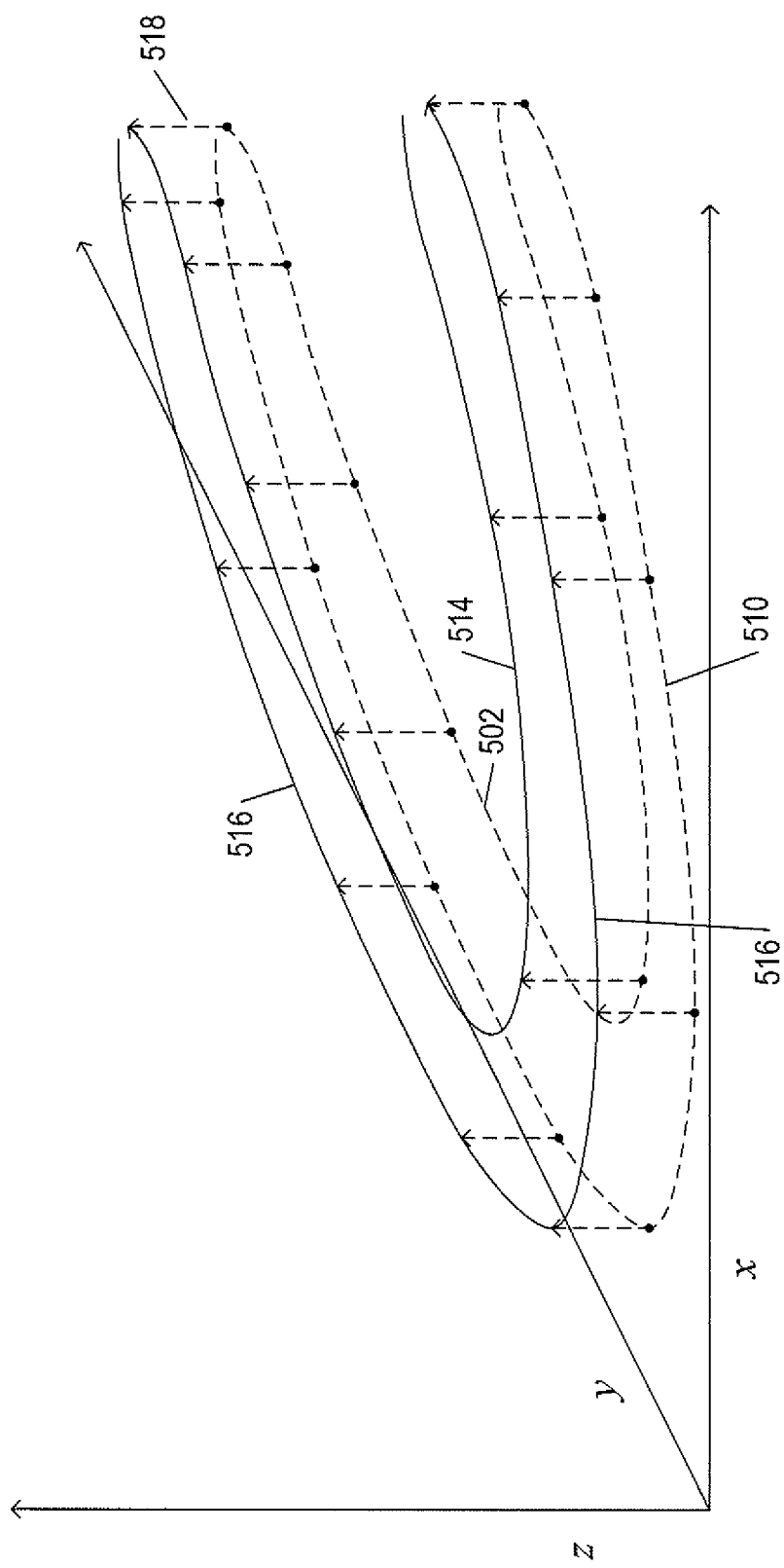

The spatial trajectory of a reference point in the optical path of the wand, such as a point centered on a transparent window through which reflected light rays from the surfaces of teeth and tissue are received by the wand, is three-dimensional. FIG. 5B shows the three-dimensional spatial trajectory corresponding to the two-dimensional projection of the spatial trajectory shown in FIG. 5A. In FIG. 5B, the three-dimensional spatial subscan trajectories 514 and 516 are shown to have z-direction displacements, represented by dashed arrows, such as dashed arrow 518, from the two-dimensional projections of the subscan trajectories 502 and 510 shown as dashed curves in FIG. 5B.

Figure 5C:
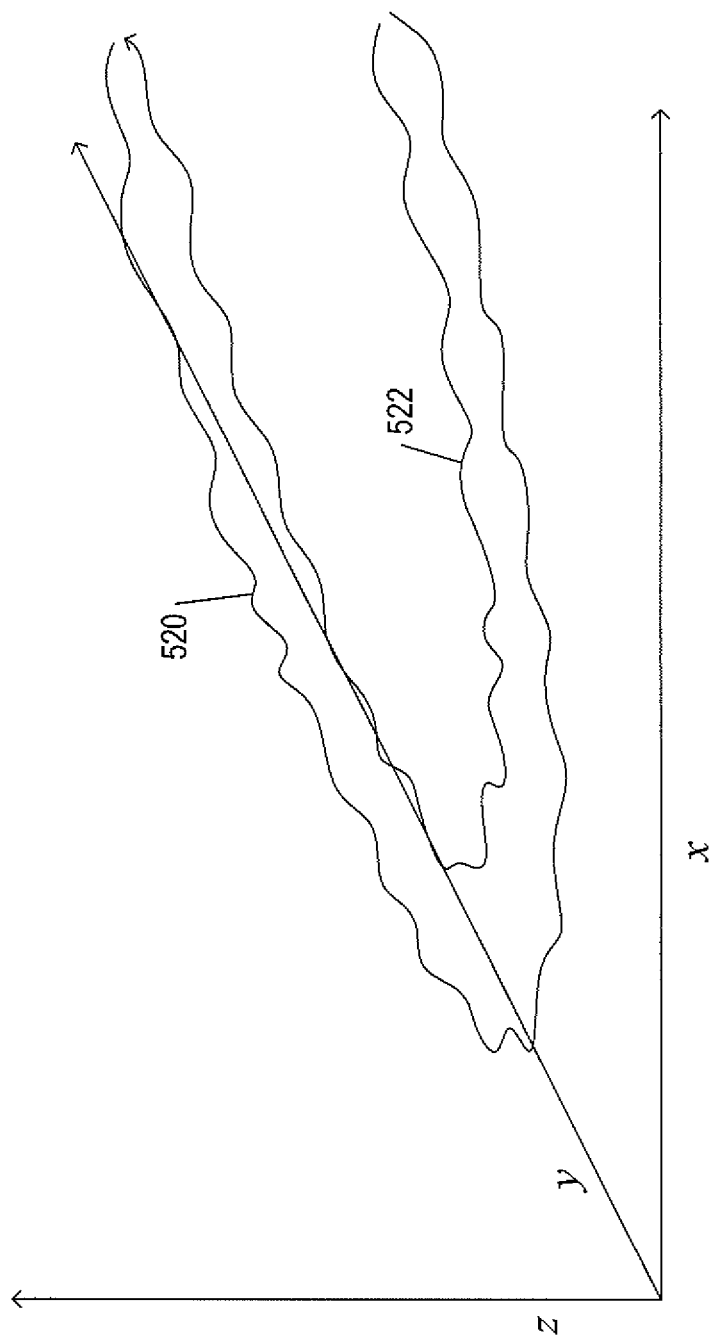

In FIGS. 5A-B, the subscan trajectories are relatively simple, planar curves. However, as shown in FIG. 5C, the actual trajectories followed by the wand may be complex curves 520 and 522 with many points of inflection and many non-linear variations in the three spatial dimensions.

Figure 5D:
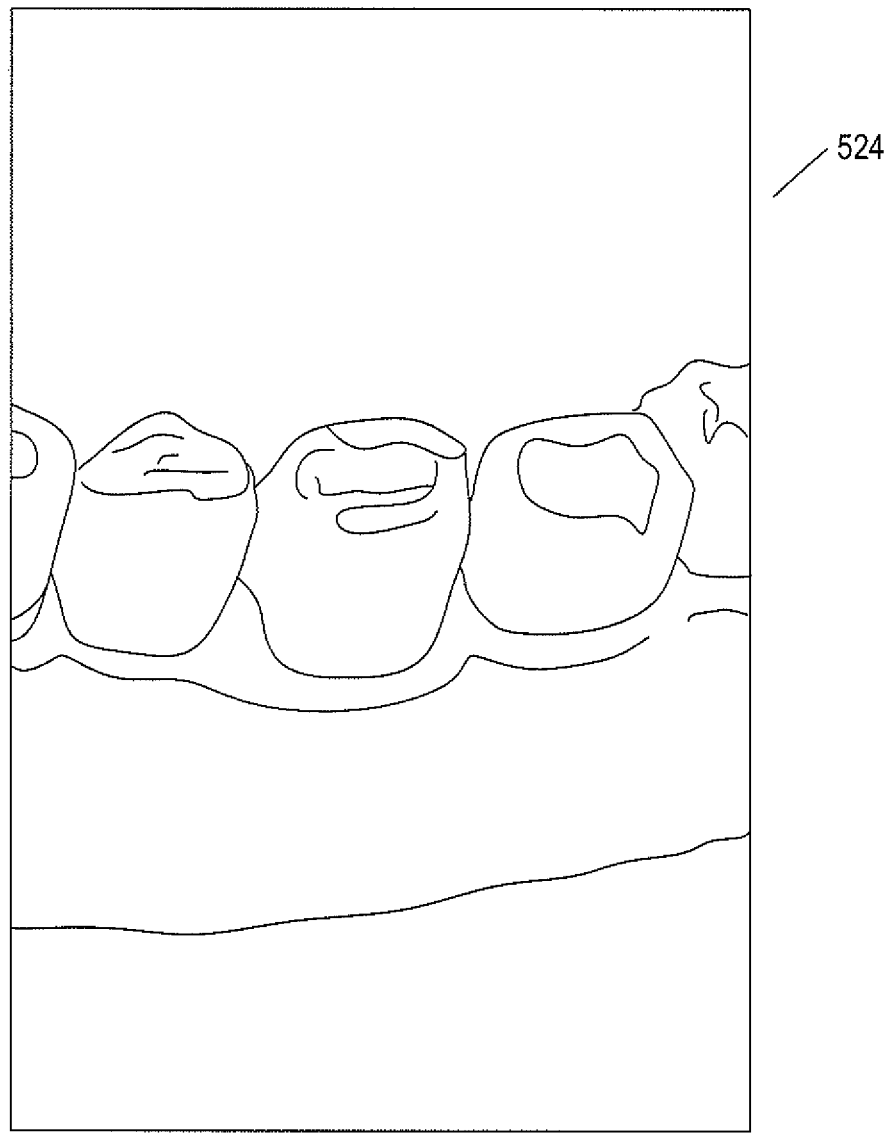

FIGS. 5D-G illustrate several of the possible types of images that may be acquired by an electro-optical-mechanical endoscope, or wand, during a scan of a patient's oral cavity. As shown in FIG. 5D, one type of image is a digital photograph. The digital photograph 524 is a pixel-based encoding of a two-dimensional photographic image. In general, each pixel may be represented by 24 bits, including three eight-bit RGB color-intensity values, or pixels may be encoded by any of many other, alternative pixel-encoding schemes.

Figure 5E:
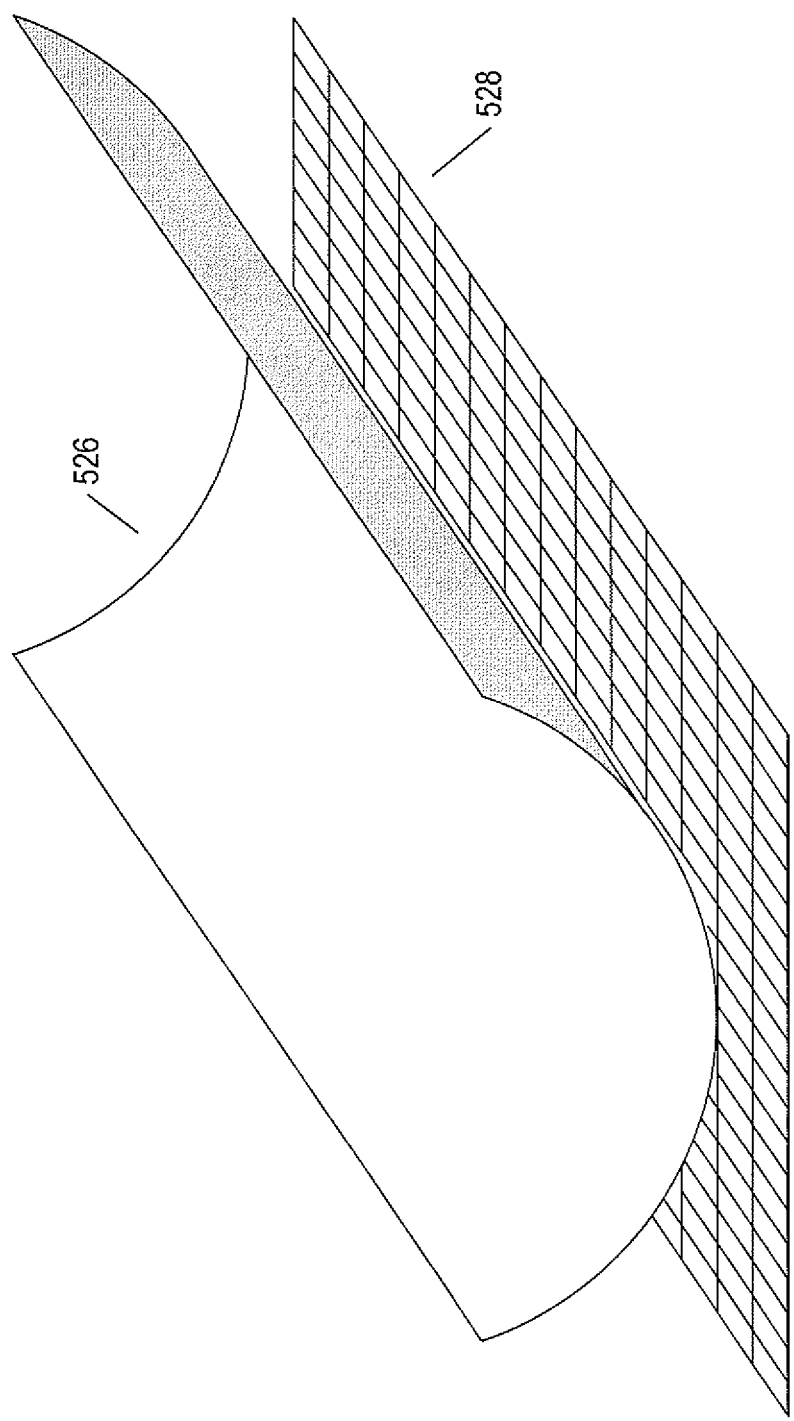

FIGS. 5E-G illustrate a depth-based encoding of a three-dimensional surface. For simplicity of illustration, the surface is shown as a portion of a cylinder, but complex surfaces, such as the surfaces of a number of adjacent teeth, can be imaged in the same fashion as the imaging of the cylindrical surface illustrated in FIGS. 5E-G. FIG. 5E shows the cylindrical surface 526 overlying a two-dimensional coordinate grid 528. In the current example, the coordinate grid is planar, but non-planar coordinate surfaces may also be employed. As shown in FIG. 5F, a distance between the coordinate-grid surface 528 and the cylindrical surface 526 in a particular direction, in this case a direction normal to the coordinate-grid plane, such as the distance 530 represented by a vertical arrow, can be computed from arbitrary points of the coordinate surface 528. FIG. 5F shows numerous computed distances from the coordinate surface 528 to the cylindrical surface 526 illustrated as arrows, such as arrow 530. As shown in FIG. 5G, a matrix of distances 532 can be stored to represented the shape of the surface, in the current example the cylindrical surface. Each value, such as the value 534, stored in the matrix represents the distance from the coordinate surface to the surface being imaged. In general, the distances are computed from the points of a grid or lattice so that the row and column coordinates of a value correspond by a simple linear transformation to locations on the coordinate surface. This matrix 532 represents a second, different type of numerically encoded image. Thus, the wand can electronically and optically acquire both two-dimensional images, such as the photographic image shown in FIG. 5D, as well as three-dimensional-surface images, such as the three-dimensional-surface image shown in FIG. 5G. In the following discussion, the unqualified term "image" may refer either to a two-dimensional photographic image or a three-dimensional-surface image.

Figure 5H:
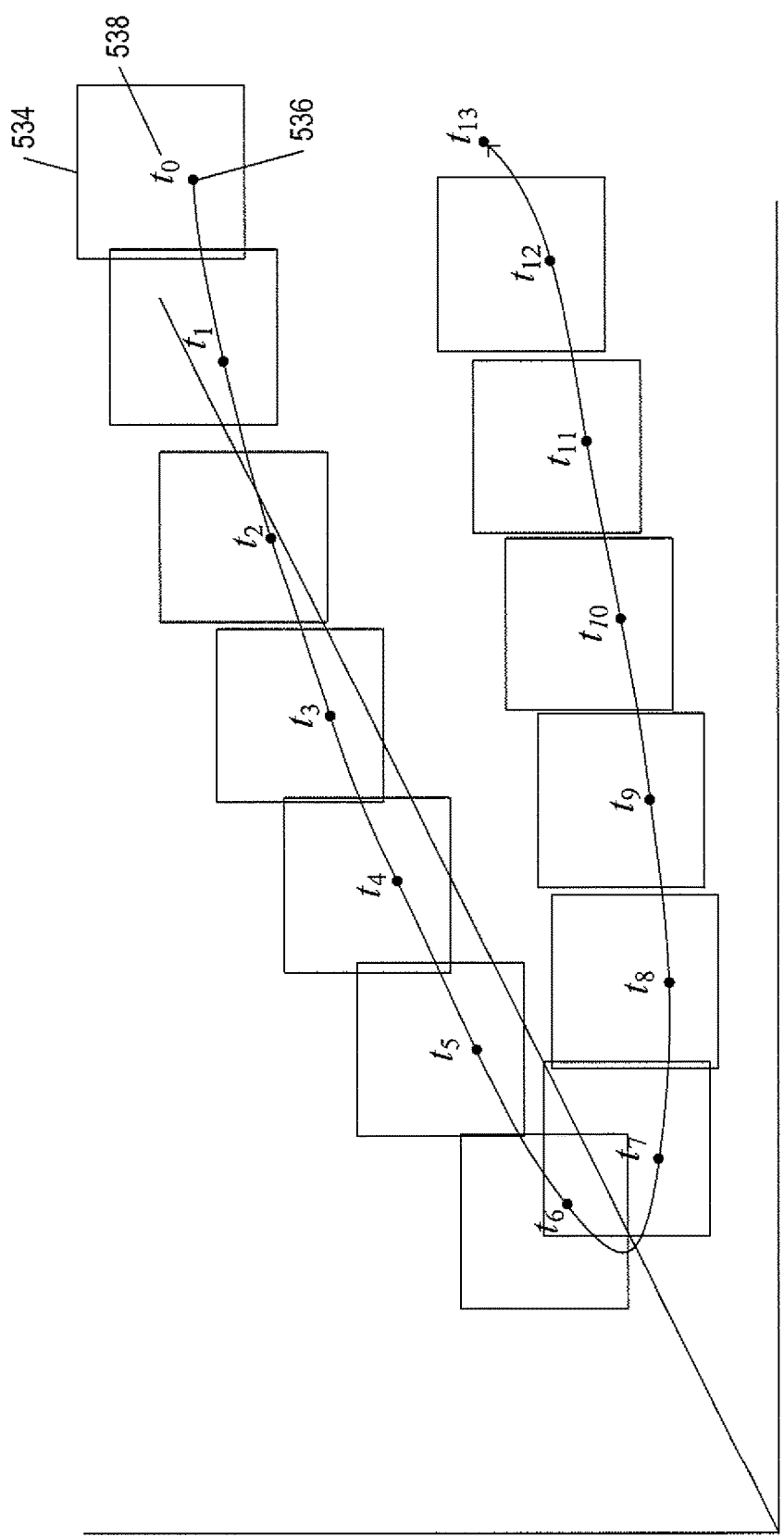
Figure 13:
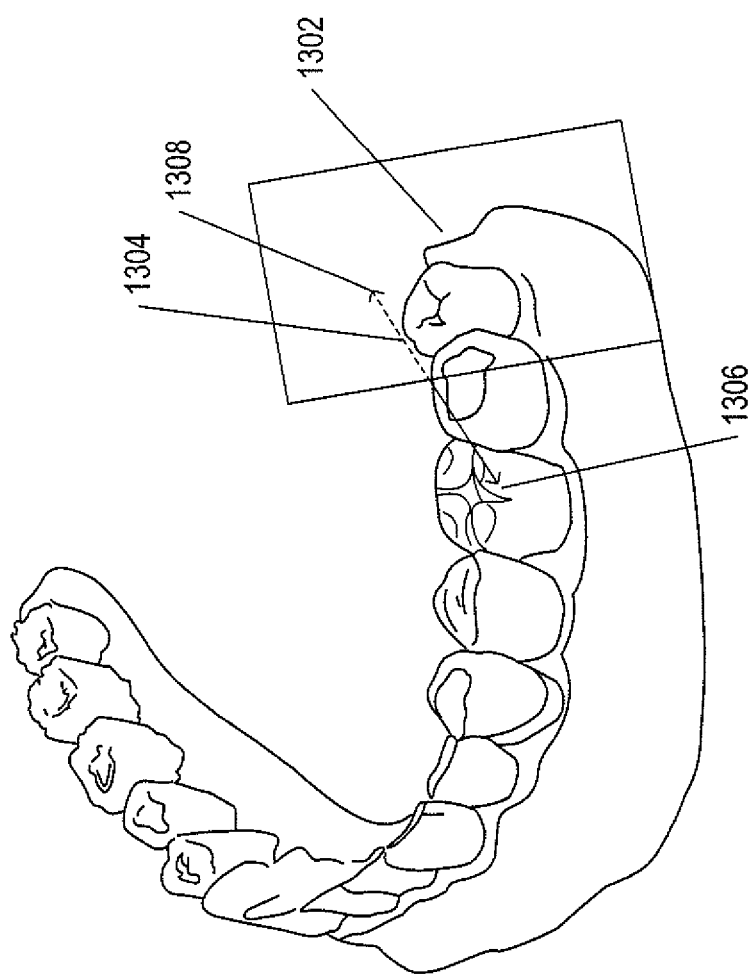
FIG. 13 shows a particular image-capture event with respect to a row of teeth and underlying tissue.

As shown in FIG. 5H, the oral-cavity-imaging-and-modeling system captures two-dimensional photographic and three-dimensional surface images at various points along a trajectory. In FIG. 5H, rectangles, such as rectangle 534, represent captured two-dimensional photographic and three-dimensional surface images when the wand has a spatial position indicated by the associated point, such as point 536 at a time indicated by a subscripted t, such as time $t_o$ 538 at which image 534 is captured by the oral-cavity-imaging-and-modeling system. In FIG. 5H, 13 images or sets images are illustrated to be captured at 13 different points on the spatial trajectory and at times $t_0$ through $t_{12}$. In an actual scan, hundreds to thousands of individual two-dimensional photographic and three-dimensional surface images may be captured. In certain systems, only two-dimensional photographic images are collected. In alternative systems, only three-dimensional surface images are collected. In the currently described system, both two-dimensional photographic and three-dimensional surface images are collected.

Figure 5I:
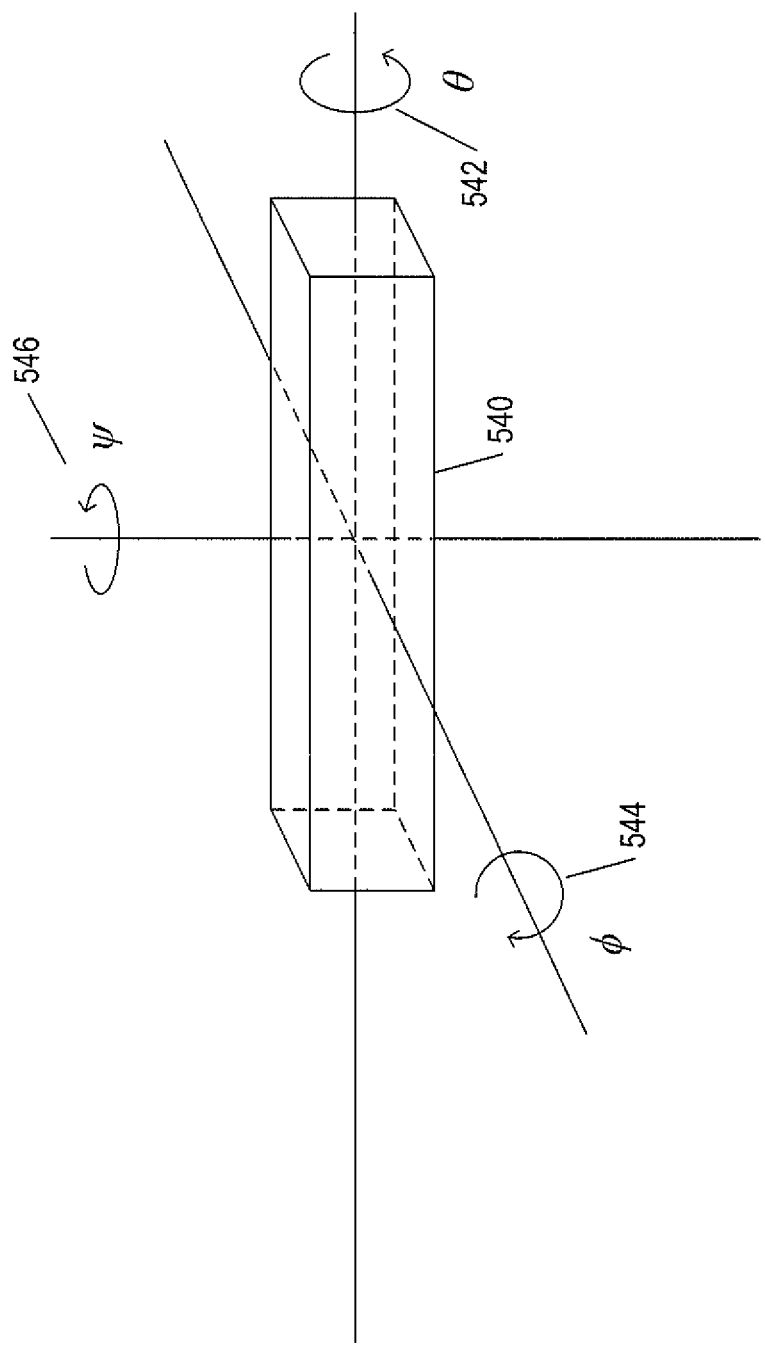

As shown in FIG. 5I, the wand may have a variety of different rotational orientations at each point along a spatial trajectory. Representing the wand as a rectangular solid 540, FIG. 5E illustrates that the rotational orientation of the wand can be expressed with three different rotational angles, or rotational coordinates, about three axes: a rotational angle θ about the x axis 542; a rotational angle φ about the y axis 544, and a rotational angle ψ 546 about the z axis. The particular image captured at any point along the spatial trajectory, as illustrated in FIG. 5H, depends not only on the spatial position of the wand when the image is captured, but also on the rotational orientation of the wand. Thus, specification of the trajectory involves, at each point of the trajectory, three spatial coordinates as well as three rotational angles, or rotational coordinates.

Figure 5J:
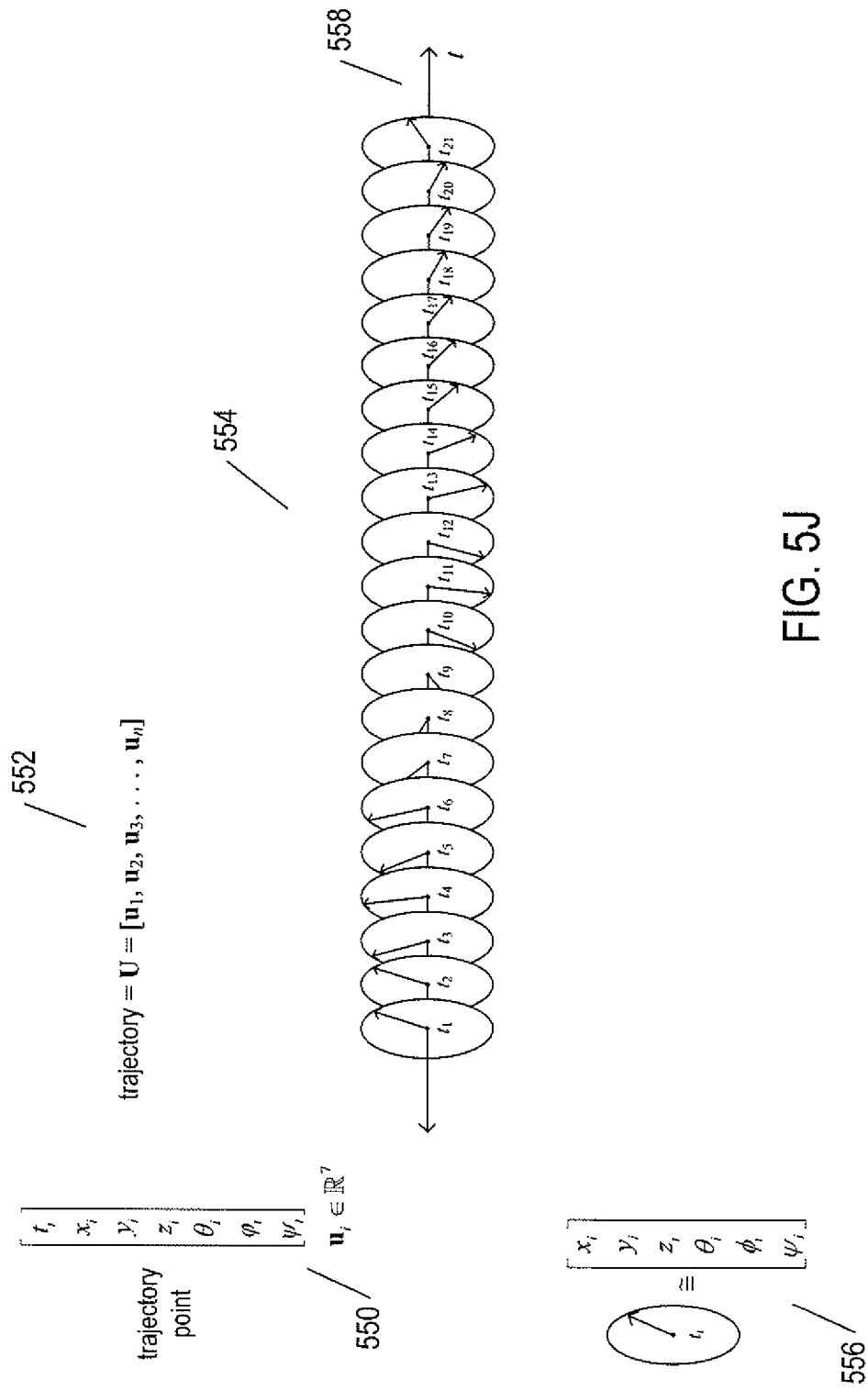

FIG. 5J illustrates the description of a wand trajectory. Each point on of the trajectory can be represented as a vector 550 in a seven-dimensional real space. The trajectory 552 is a time-ordered ordered set of trajectory points. Alternatively, a trajectory may be considered to be a sequence 554 of six-dimensional vectors 556 ordered in time along a time line 558. Depending on the ability for spatial position and orientation to be determined, lower-dimensional vectors may used those cases when less precise spatial-position and/or orientation information can be determined.

FIG. 5K illustrates a trajectory envelope. In FIG. 5K, a short, linear portion of a scan trajectory 560 is shown in a three-dimensional plot. A projection of this trajectory segment is shown as dashed line 562 in the x-y plane. Trajectory segment 560 may be a short, linear portion of an optimal trajectory that, when followed, leads to generation of an accurate three-dimensional digital model of the oral cavity under certain constraints. However, in many practical cases, there may be more than a single optimal trajectory and there may be many suboptimal but acceptable related trajectories, all of which lead to an accurate, three-dimensional digital model of the oral cavity. In general, a training system seeks to teach technicians to guide the wand within some extended envelope 564 that generally includes multiple optimal trajectories and multiple suboptimal, but acceptable trajectories 560. There may be multiple possible starting points for a scan, each starting point associated with its own trajectory envelope representing a set of related optimal and suboptimal, but acceptable, scan trajectories. The envelopes associated with two different starting points may include common trajectory points. A trainee may be allowed to select one of many possible starting positions, by a training system, after which the training system may seek to teach the trainee to guide the wand within an extended trajectory envelope representing optimal and/or suboptimal, but acceptable, trajectories associated with a starting point. The volume of the trajectory envelope may decrease, over the course of training of a particular trainee, as the trainee gains proficiency, with the trajectories contained in trajectory envelope increasing dominated by optimal trajectories.

Another perspective on the training of technicians to operate oral-cavity-imaging-and-modeling equipment is next provided. As discussed above with reference to FIG. 5J, a particular scan trajectory U is an ordered set of points in $\mathbb{R}^7$:

$$U = [u_1, u_2, u_3, \ldots, u_n]$$

where $$u_i = \begin{bmatrix} t_i \\ x_i \\ y_i \\ z_i \\ \theta_i \\ \varphi_i \\ \psi_i \end{bmatrix}.$$

The set of all possible trajectories V includes all possible scanning trajectories:

$$V = [U_1, U_2, \ldots U_n].$$

V is essentially an infinite set. There is a set of all possible scan trajectories that produce acceptably accurate three-dimensional oral-cavity models, $V_a$:

$$V_a \subset V.$$

There is an additional set of all possible optimal scan trajectories $V_o$:

$$V_o \subset V_a.$$

The set $V_o$ represents a selection of trajectories from the set $V_a$ via an optimization technique:

$$V_o = \text{optimize}(V_a, \text{constraint\_1}, \text{constraint\_2}, \ldots)$$

where a given constraint_i may be:
  minimize total scan time T;
  minimize number of captured images N;
  minimize length at trajectory L;
  minimize contact of endoscope with patient P;
  minimize total rotational movement of endoscope M.

There are many different types of constraints that may be used to guide optimization, including those mentioned in the above equation. The set of constraints employed may themselves be determined by a higher-level optimization technique. A minimal goal for automated or semi-automated training of oral-cavity-imaging-and-modeling-equipment technicians is to train the technicians to carry out scans with trajectories that fall within the set $V_a$. In other words, a minimal goal of training is to ensure that technicians carry out scans that produce acceptably precise three-dimensional digital models of the oral cavities of patients. The accuracy of a three-dimensional model may be specified in many different ways, including an average discrepancy between the positions of points on the surfaces of the three-dimensional model and corresponding points on the surfaces of teeth and gums or a model of teeth and gums. A maximum goal for automated or semi-automated training may be to train technicians to carry out scans with trajectories in $V_o$. The trajectory envelopes associated with a particular training subject and associated three-dimensional, digital model may be computed in advance of training or may be computed dynamically for current and predicted wand positions and orientations as a training scan proceeds.

Figure 6:
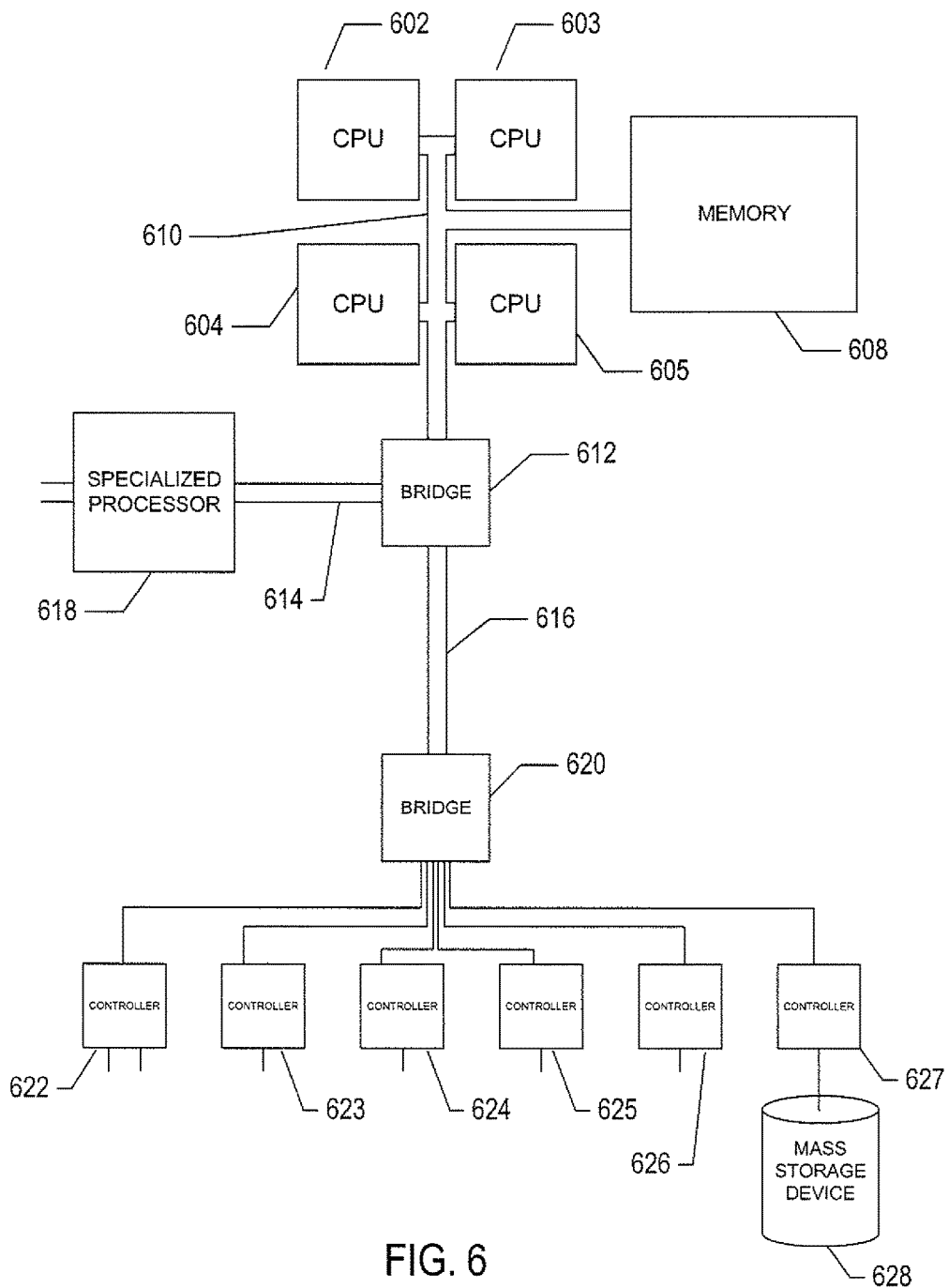
FIG. 6 provides a general architectural diagram for various types of computers.

FIG. 6 provides a general architectural diagram for various types of computers. The computer system contains one or multiple central processing units ("CPUs") 602-605, one or more electronic memories 608 interconnected with the CPUs by a CPU/memory-subsystem bus 610 or multiple busses, a first bridge 612 that interconnects the CPU/memory-subsystem bus 610 with additional busses 614 and 616, or other types of high-speed interconnection media, including multiple, high-speed serial interconnects. These busses or serial interconnections, in turn, connect the CPUs and memory with specialized processors, such as a graphics processor 618, and with one or more additional bridges 620, which are interconnected with high-speed serial links or with multiple controllers 622-627, such as controller 627, that provide access to various different types of mass-storage devices 628, electronic displays, input devices, and other such components, subcomponents, and computational resources. It should be noted that computer-readable data-storage devices include optical and electromagnetic disks, electronic memories, and other physical data-storage devices. Those familiar with modern science and technology appreciate that electromagnetic radiation and propagating signals do not store data for subsequent retrieval, and can transiently "store" only a byte or less of information per mile, far less information than needed to encode even the simplest of routines. The computing subsystem within an oral-cavity-imaging-and-modeling system generally has an architecture similar to the computer architecture illustrated in FIG. 6, although a large variety of different detailed computer systems may be used in various different implementations of an oral-cavity-imaging-and-modeling system. There are many different types of computer-system architectures that differ from one another in the number of different memories, including different types of hierarchical cache memories, the number of processors and the connectivity of the processors with other system components, the number of internal communications busses and serial links, and in many other ways. However, computer systems generally execute stored programs by fetching instructions from memory and executing the instructions in one or more processors.

Figure 7A:
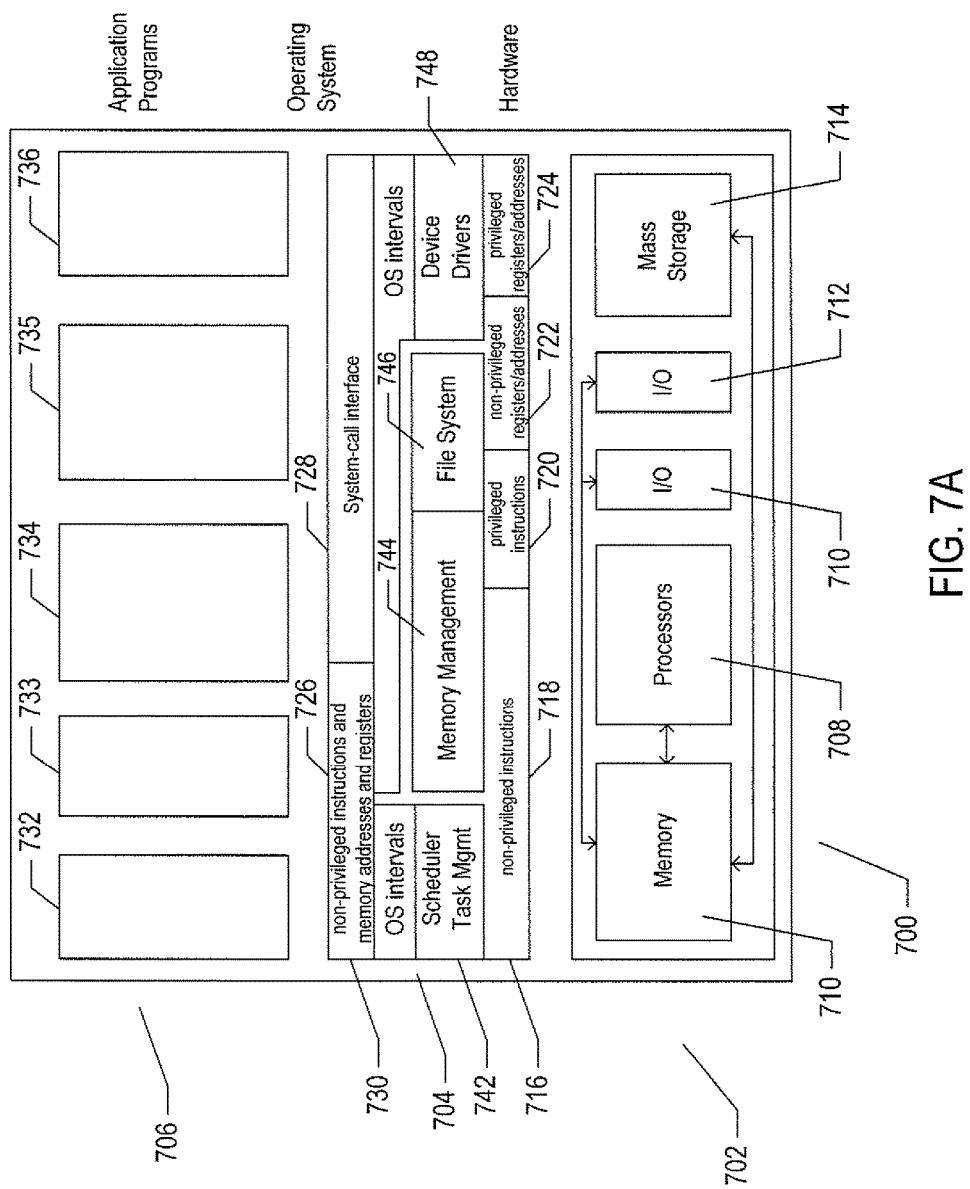
FIG. 7A illustrates generalized hardware and software components of a general-purpose computer system, such as a general-purpose computer system having an architecture similar to that shown in FIG. 6.

FIG. 7A illustrates generalized hardware and software components of a general-purpose computer system, such as a general-purpose computer system having an architecture similar to that shown in FIG. 6. The computer system 700 is often considered to include three fundamental layers: (1) a hardware layer or level 702; (2) an operating-system layer or level 704; and (3) an application-program layer or level 706. The hardware layer 702 includes one or more processors 708, system memory 710, various different types of input-output ("I/O") devices 710 and 712, and mass-storage devices 714. Of course, the hardware level also includes many other components, including power supplies, internal communications links and busses, specialized integrated circuits, many different types of processor-controlled or microprocessor-controlled peripheral devices and controllers, and many other components. The operating system 704 interfaces to the hardware level 702 through a low-level operating system and hardware interface 716 generally comprising a set of non-privileged computer instructions 718, a set of privileged computer instructions 720, a set of non-privileged registers and memory addresses 722, and a set of privileged registers and memory addresses 724. In general, the operating system exposes non-privileged instructions, non-privileged registers, and non-privileged memory addresses 726 and a system-call interface 728 as an operating-system interface 730 to application programs 732-736 that execute within an execution environment provided to the application programs by the operating system. The operating system, alone, accesses the privileged instructions, privileged registers, and privileged memory addresses. By reserving access to privileged instructions, privileged registers, and privileged memory addresses, the operating system can ensure that application programs and other higher-level computational entities cannot interfere with one another's execution and cannot change the overall state of the computer system in ways that could deleteriously impact system operation. The operating system includes many internal components and modules, including a scheduler 742, memory management 744, a file system 746, device drivers 748, and many other components and modules. To a certain degree, modern operating systems provide numerous levels of abstraction above the hardware level, including virtual memory, which provides to each application program and other computational entities a separate, large, linear memory-address space that is mapped by the operating system to various electronic memories and mass-storage devices. The scheduler orchestrates interleaved execution of various different application programs and higher-level computational entities, providing to each application program a virtual, stand-alone system devoted entirely to the application program. From the application program's standpoint, the application program executes continuously without concern for the need to share processor resources and other system resources with other application programs and higher-level computational entities. The device drivers abstract details of hardware-component operation, allowing application programs to employ the system-call interface for transmitting and receiving data to and from communications networks, mass-storage devices, and other I/O devices and subsystems. The file system 736 facilitates abstraction of mass-storage-device and memory resources as a high-level, easy-to-access, file-system interface. Thus, the development and evolution of the operating system has resulted in the generation of a type of multi-faceted virtual execution environment for application programs and other higher-level computational entities.

Figure 7B:
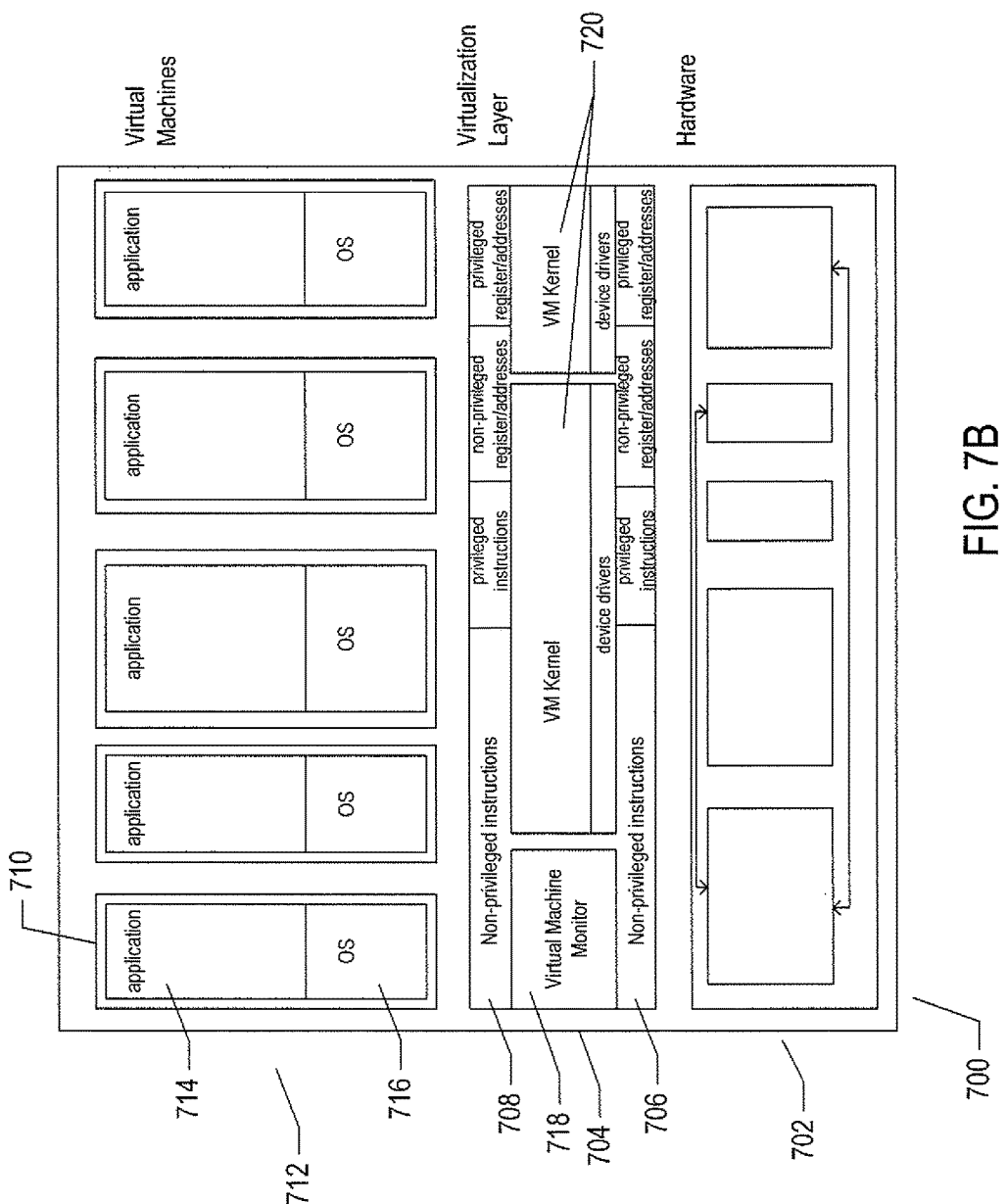
FIG. 7B illustrates generalized hardware and software components of a general-purpose computer system, such as a general-purpose computer system having an architecture similar to that shown in FIG. 6, which includes a virtualization layer.

FIG. 7B illustrates generalized hardware and software components of a general-purpose computer system, such as a general-purpose computer system having an architecture similar to that shown in FIG. 6, which includes a virtualization layer. The computer system 750 in FIG. 7B includes the same hardware layer 752 as the hardware layer 702 shown in FIG. 7A. However, rather than providing an operating system layer directly above the hardware layer, as in FIG. 7A, the virtualized computing environment illustrated in FIG. 7B features a virtualization layer 754 that interfaces through a virtualization-layer/hardware-layer interface 756, equivalent to interface 716 in FIG. 7A, to the hardware. The virtualization layer provides a hardware-like interface 758 to a number of virtual machines, such as virtual machine 760, executing above the virtualization layer in a virtual-machine layer 762. Each virtual machine includes one or more application programs or other higher-level computational entities packaged together with an operating system, referred to as a "guest operating system," such as application 764 and guest operating system 766 packaged together within virtual machine 760. Each virtual machine is thus equivalent to the operating-system layer 704 and application-program layer 706 in the general-purpose computer system shown in FIG. 7A. Each guest operating system within a virtual machine interfaces to the virtualization-layer interface 758 rather than to the actual hardware interface 756. The virtualization layer partitions hardware resources into abstract virtual-hardware layers to which each guest operating system within a virtual machine interfaces. The guest operating systems within the virtual machines, in general, are unaware of the virtualization layer and operate as if they were directly accessing a true hardware interface. The virtualization layer ensures that each of the virtual machines currently executing within the virtual environment receive a fair allocation of underlying hardware resources and that all virtual machines receive sufficient resources to progress in execution. The virtualization layer includes a virtual-machine-monitor module 768 ("VMM") that virtualizes physical processors in the hardware layer to create virtual processors on which each of the virtual machines executes. For execution efficiency, the virtualization layer attempts to allow virtual machines to directly execute non-privileged instructions and to directly access non-privileged registers and memory. However, when the guest operating system within a virtual machine accesses virtual privileged instructions, virtual privileged registers, and virtual privileged memory through the virtualization-layer interface 758, the accesses result in execution of virtualization-layer code to simulate or emulate the privileged resources. The virtualization layer additionally includes a kernel module 770 that manages memory, communications, and data-storage machine resources on behalf of executing virtual machines ("VM kernel").

Figure 8:
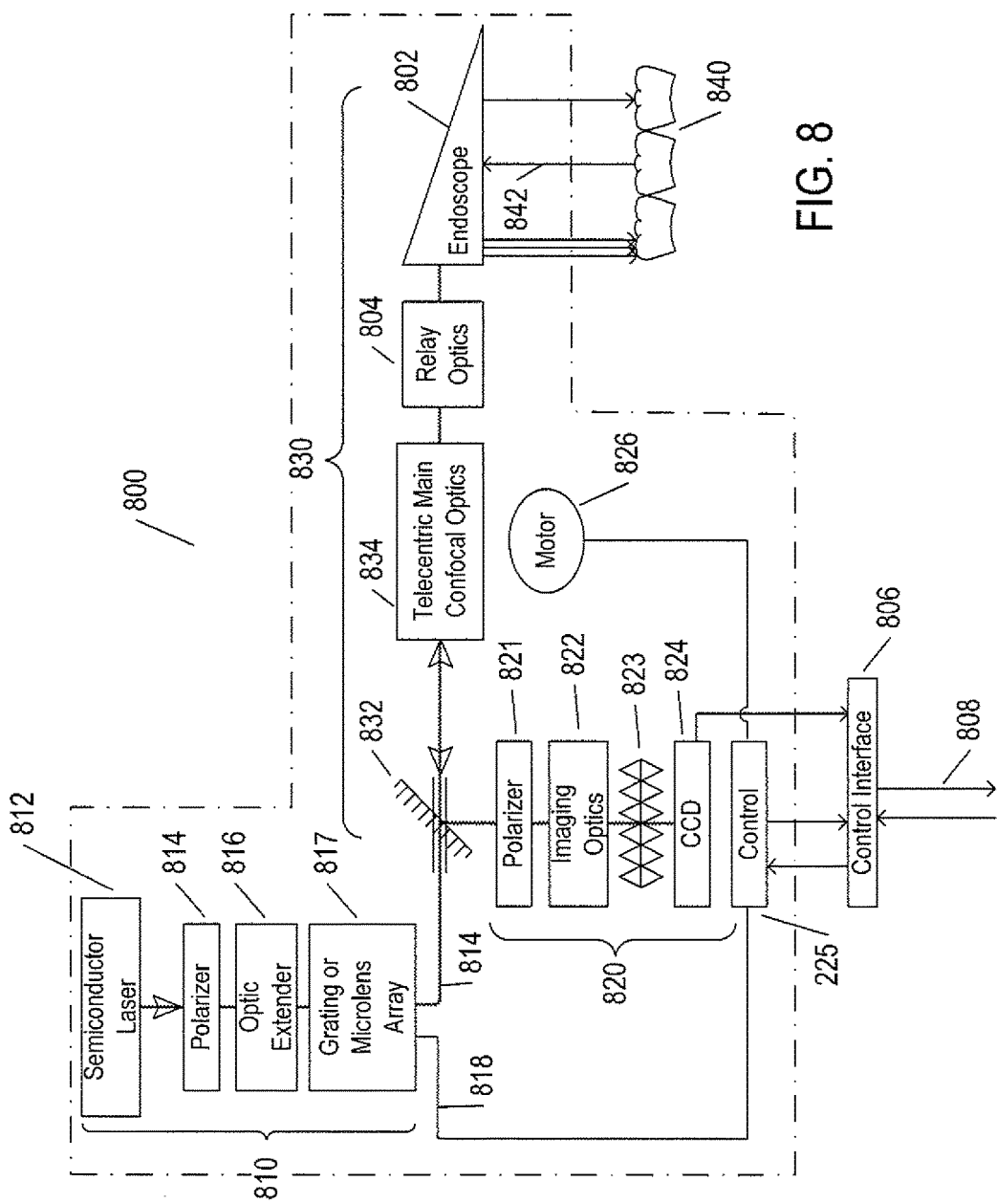
FIG. 8 illustrates the image-capture subsystem of one implementation of an oral-cavity-imaging-and-modeling system.

FIG. 8 illustrates the image-capture subsystem of one implementation of an oral-cavity-imaging-and-modeling system. The image-capture subsystem 800 includes the endoscope or wand 802, relay optics 804 that transmit polarized laser light to the endoscope and transmit reflected light from teeth and tissues captured by the endoscope to upstream imaging components. The endoscope 802, or wand, is manipulated by the technician in order to scan oral cavities of patients and is connected, via an electro-optical cable, to the remaining components of the image-capture subsystem 800. The image-capturing subsystem 800 is interconnected with the computational system, described above with reference to FIGS. 6 and 7A-B, through a control interface 806, with high-speed serial or parallel signal paths 808 that are connected via a bridge to processors and memory of the computational system within the oral-cavity-imaging-and-modeling system.

The image-capture subsystem 800 includes an illumination-source subsystem 810, an image-capture-optics subsystem 820, and a main-optics subsystem 830. The illumination-source subsystem 810 includes a semiconductor laser light source 812, a polarizer 814 that polarizes the laser light emitted from the semiconductor laser 812, an optic expander 816 which alters the numerical aperture of the polarized light emitted from the polarizer 814, and a grating or micro lens array 817 that splits light input to the grating or micro lens array into multiple output light paths 818 and 819. The main-optics subsystem 830 includes a partially transparent mirror 832 which transmits light from light path 819 towards the remaining components of the main-optic subsystem 830 but which reflects light returning from the endoscope downward to the image-detection subsystem 820. The main-optics subsystem 830 further includes confocal optics 834 operating in a telecentric mode, which ameliorates distance-introduced magnification changes.

The endoscope 802 is a generally hollow wand-shaped device with an internal light transmission path and directs polarized laser light towards teeth and tissue 840. Light reflected back from teeth and tissues forms a return light beam that is passed, by the endoscope, back through the relay optics 804 and confocal optics 834 to the partially reflective mirror 832, which reflects the returning light beam into the image-capture-optics subsystem 820. The image-capture-optics subsystem includes a second polarizer 821 with a plane of polarization oriented normal to the plane of polarization of the first polarizer 814. Return light then passes through imaging optics 822 and through a matrix of pinholes 823, following which the return light falls on a charge-coupled-detector ("CCD") camera 824 for image capture. A control module 825 controls both operation of a semiconductor laser 812 as well as a motor 826 linked to the telecentric confocal optics module 834 which is controlled to change the relative location of the focal plane of the telecentric confocal optics module with respect to the direction normal to the light-gathering aperture of the endoscope, represented by arrow 842.

The matrix, control module, and motor cooperate to monitor the intensity of individual light paths emerging from the matrix as the position of the plane of focus changes in order to determine the depth, in the direction 842, of the nearest surface of tooth or tissue to the wand. In this fashion, the wand not only captures two-dimensional images of the oral cavity, but the system, as a whole, is able to assign a distance from the wand to points in the two-dimensional image corresponding to light paths emerging from the matrix, thus producing a three-dimensional surface image, as described above with reference to Figures E-G. Both two-dimensional photograph images and three-dimensional surface images can be used alone, or together, to construct a three-dimensional digital model of the oral cavity from the two-dimensional photographic and three-dimensional surface images captured by the oral-cavity-imaging-and-modeling system.

Figure 9:
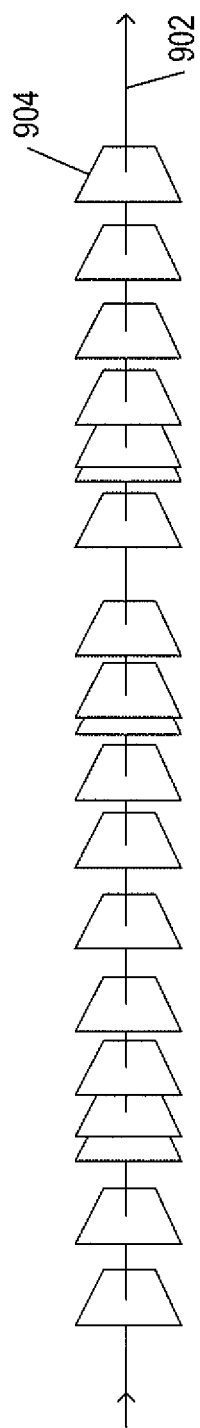
FIG. 9 illustrates image capture by the oral-cavity-imaging-and-modeling system over a small portion of a scan trajectory.

FIG. 9 illustrates image capture by the oral-cavity-imaging-and-modeling system over a small portion of a scan trajectory. In FIG. 9, line 902 represents a small portion of a scan trajectory and each rectangle, such as rectangle 904, represents a captured image. As the wand is moved along a row of teeth, the oral-cavity-imaging-and-modeling system continuously monitors the time, position, and orientation of the wand and, from the information collected by monitoring, computes a variety of different parameters that the oral-cavity-imaging-and-modeling system uses to determine when to next capture and record a two-dimensional photographic and/or three-dimensional surface image. Examples of these parameters include the elapsed time since a previous image was captured, an estimated distance that the wand has moved since the last image was captured, a computed overlap between the last-captured image and an image that would be captured at the present time, the velocity of wand movement, an angular velocity of rotational movement of the wand, and many other such parameters. Values for the parameters may be estimated from previously gathered information or from received output from various types of sensors within the wand or other components of the oral-cavity monitory system. As shown in FIG. 9, the distance, in seven-dimensional space, between trajectory points at which images are captured may vary, depending on the nature of the oral-cavity features currently being imaged as well as on additional considerations. When the trajectory of the wand does not fall within the set of trajectories $V_8$ that provide for generating acceptable three-dimensional digital models of the oral cavity, the oral-cavity-imaging-and-modeling system is generally unable to acquire sufficient imaging coverage of the oral cavity to allow for accurate computation of a three-dimensional digital model from the set of two-dimensional images captured by the wand as it moves along the trajectory. As one example, there may be a minimum latency time between image-capture events, as a result of which, when the wand is moving too quickly, the oral-cavity-imaging-and-modeling system is unable to acquire sufficient information for a portion of the oral cavity to construct an accurate three-dimensional digital model of that portion of the oral cavity. As another example, it may be necessary for the wand to be rotated as the wand is moved spatially along a row of teeth in order to obtain images of all portions of the teeth, and, when the wand trajectory does not include sufficient rotational motion, only a portion of the teeth are imaged, as a result of which there is insufficient information to construct an accurate three-dimensional digital model.

Figure 10:
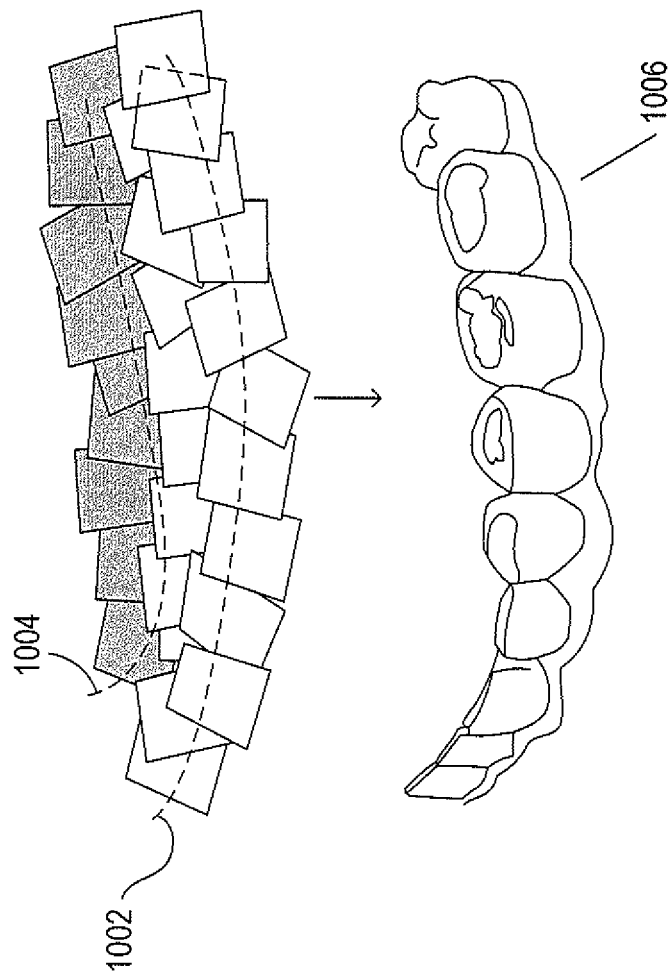
FIG. 10 illustrates generation of an accurate three-dimensional digital model from two-dimensional images.

FIG. 10 illustrates generation of an accurate three-dimensional digital model from two-dimensional images. As shown in FIG. 10, when the wand is correctly employed by a technician, the trajectory of the wand, represented, in part, by dashed lines 1002 and 1004, allows for acquisition of a sufficient number and type of two-dimensional photographic and/or three-dimensional surface images to allow for generation of an accurate three-dimensional digital model 1006. By computationally overlapping the images and rotating the images with respect to one another in order to obtain maximum correspondence between features of adjacent images, a precise, digital spatial model of teeth and underlying tissue, similar to spatial models generated by various types of computer-aided-design and solid-modeling software used for mechanical systems, is obtained.

Figure 11A:
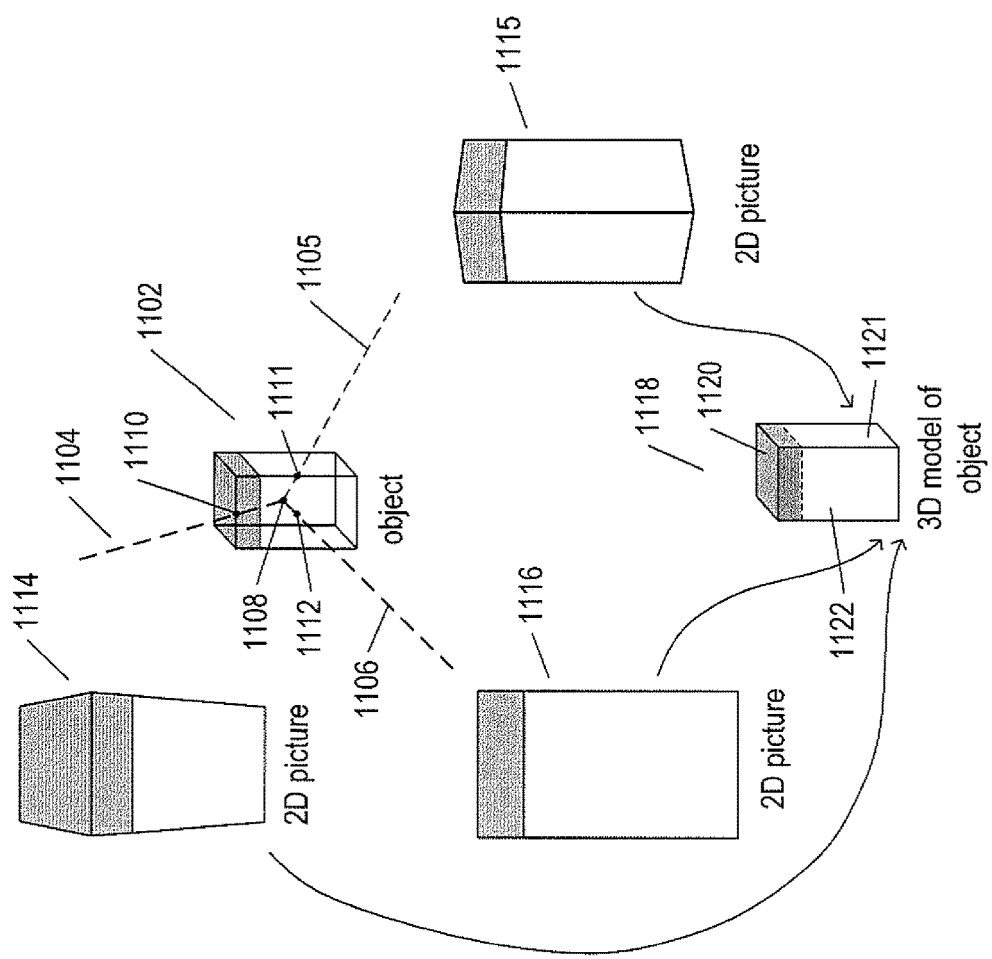
FIGS. 11A-B illustrate use of two-dimensional images to generate a three-dimensional model of an imaged object.
Figure 11B:
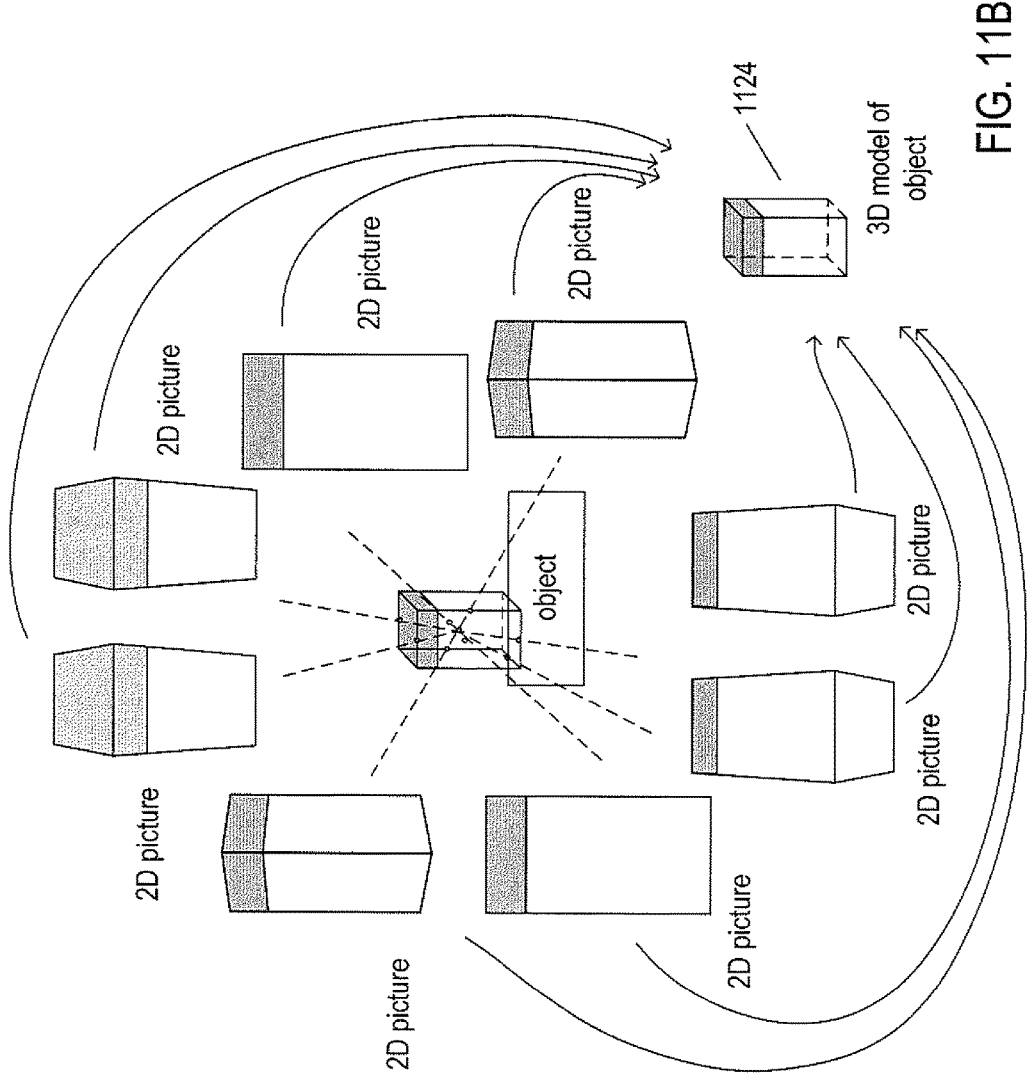

FIGS. 11A-B illustrate use of two-dimensional images to generate a three-dimensional model of an imaged object. In FIG. 11A, a rectangular solid object with a shaded top portion 1102 is shown. Dashed lines 1104-1106 that begin at a central point 1108 within the interior of the object and each pass through an additional point 1110-1112 on the surface of the object, indicate the directions normal to an image-capture apparatus that captures three two-dimensional images 1114-1116 of the object. From these images, as well as distance information associated with various points within the images, a partial three-dimensional model of the object 1118 can be computationally generated. Note, however, that the three-dimensional model 1118 is incomplete, having accurate representations of only three 1120-1122 of the six faces of the object. No image was taken that included portions of the other three faces. By contrast, as shown in FIG. 11B, when a sufficient number of two-dimensional images, with associated depth information, are captured from a sufficient number of different directions, an accurate three-dimensional model of the object 1124 can be computationally generated. Similar considerations apply when combining two-dimensional photographic images with three-dimensional surface images and when combining three-dimensional surface images.

Figure 12A:
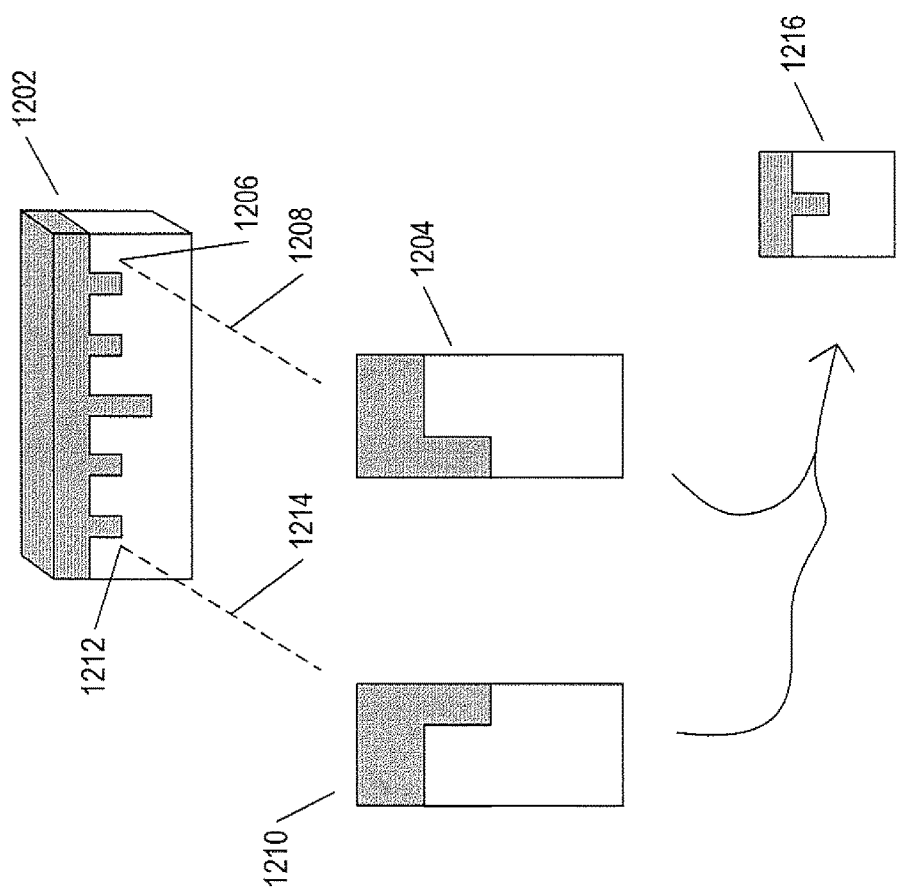
FIGS. 12A-B illustrate the need for adequate sampling frequency over spatial dimensions.
Figure 12B:
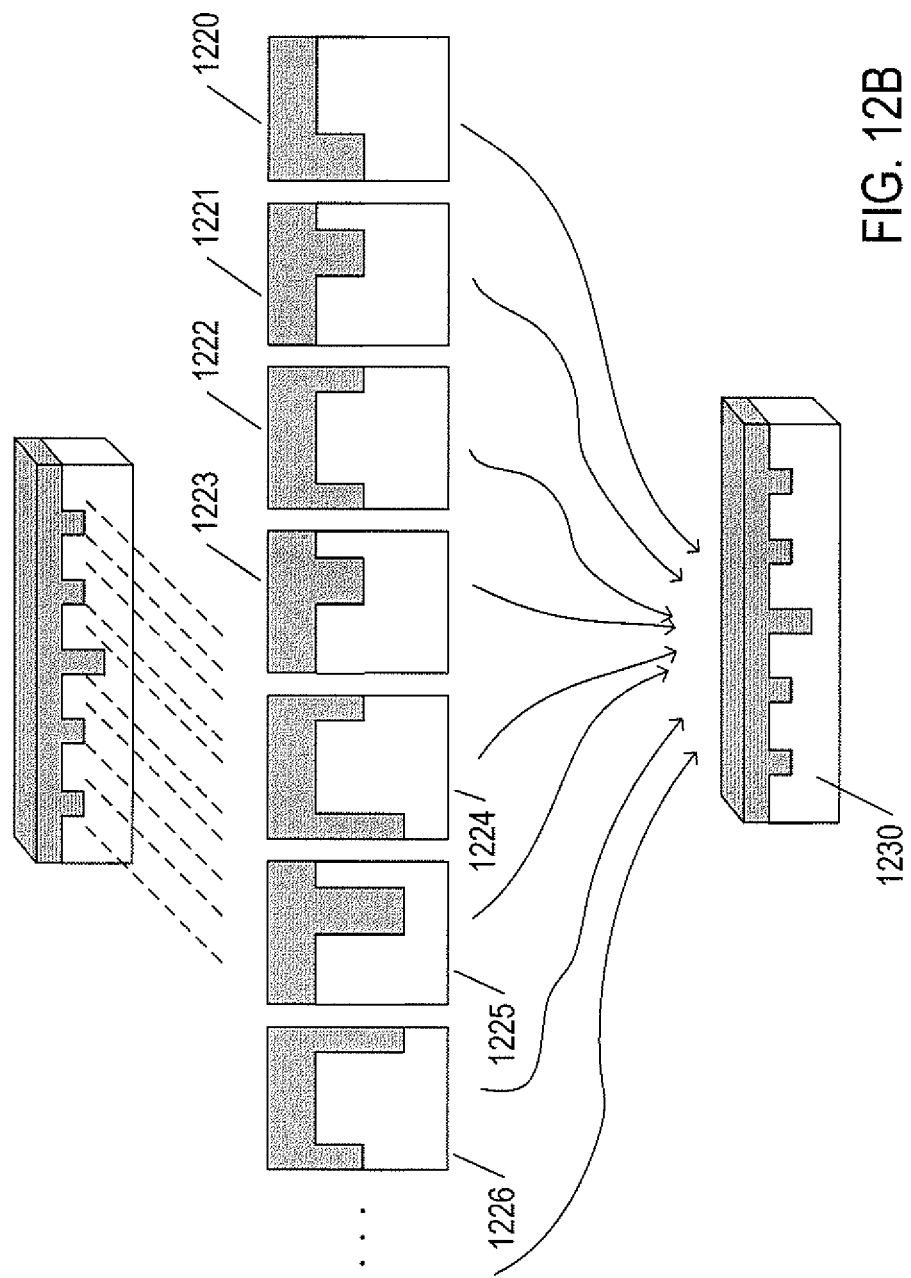

FIGS. 12A-B illustrate the need for adequate sampling frequency over spatial dimensions. In FIG. 12A, a long, rectangular, solid object 1202 is imaged by an image-capture system. The image-capture system captures a first two-dimensional image 1204 from a position represented by point 1206 and direction represented by dashed line 1208 and a second two-dimensional image 1210 from a second position 1212 and direction 1214. One possible computational combination of these two two-dimensional images 1204 and 1210 would produce a partial model 1216 that includes only a portion of the front face of the long, rectangular solid object 1202. Clearly, an insufficient amount of information is contained in the two two-dimensional images 1204 and 1210 to reconstruct even an accurate representation of one face of the long, rectangular solid object 1202. By contrast, as shown in FIG. 12B, when a sufficient number of images are acquired along a direction parallel to the long axis of the solid-rectangular object 1220-1226, then, by computationally computing translational overlaps of adjacent images, a final accurate model of the front face of the solid-rectangular object 1230 can be produced. Thus, for accurate three-dimensional digital modeling, two-dimensional images need to be captured from a sufficient number of orientations and translational positions to provide sufficient coverage of the surfaces and features of the three-dimensional object in order to computationally reconstruct the three-dimensional object from the collected two-dimensional images and depth information. Similar considerations apply when combining two-dimensional photographic images with three-dimensional surface images and when combining three-dimensional surface images.

When an accurate three-dimensional digital model of the oral cavity of a particular patient is known, or when, for training purposes, a technician employs an oral-cavity-imaging-and-modeling system to image and generate a three-dimensional model for a physical model already associated with an accurate three-dimensional digital model, information collected by a wand can be used to determine the spatial position and rotational orientation of the wand.

FIG. 13 shows a particular image-capture event with respect to a row of teeth and underlying tissue. The captured image, represented by rectangle 1302, has a particular distance in a normal direction, represented by dashed arrow 1304, from each point on the imaged surfaces of the row of teeth. In FIG. 13, a particular point 1306 on the surface of a tooth is nearest to a central point 1308 of the two-dimensional image 1302 in the normal direction 1304. When there is an already generated, accurate three-dimensional digital model for the row of teeth being imaged, as shown in FIG. 13, a two-dimensional photographic or three-dimensional surface image captured from a wand at a particular spatial and rotational position can be used to determine the spatial and rotational position of the wand. The two-dimensional photographic or three-dimensional surface image can be matched to a plane projection of a portion of the three-dimensional digital model by translations and rotations of the two-dimensional image with respect to the three-dimensional digital model. The translations and rotations that place the two-dimensional photographic or three-dimensional surface image in a position corresponding to the best-matching plane projection can be used to compute the spatial position and rotational orientation of the wand.

Figures 14A, 14B:
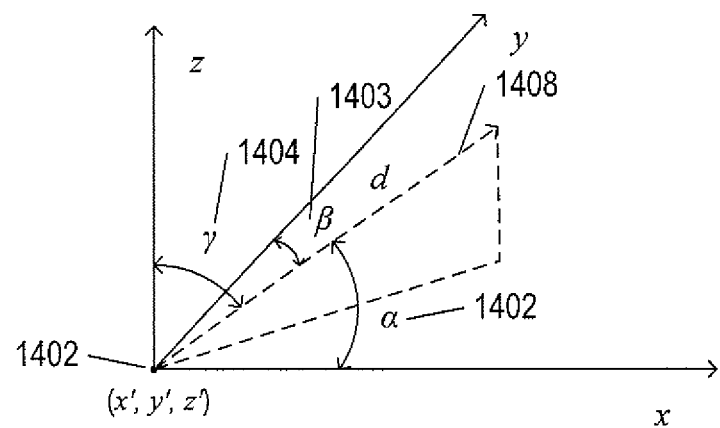
FIGS. 14A-B illustrate determination of a trajectory point corresponding to a two-dimensional photographic or three-dimensional surface image captured during a training session.

FIGS. 14A-B illustrate determination of a trajectory point corresponding to a two-dimensional photographic or three-dimensional surface image captured during a training session. By a search of possible spatial and rotational orientations of the two-dimensional image with respect to the three-dimensional model, a best-matching position and orientation is found. As shown in FIG. 14A, the position and orientation can be expressed as a set of three angles 1402-1404 with respect to a model coordinate system and a local or relative position of an origin 1406 of a local Cartesian coordinate system in terms of an absolute Cartesian coordinate system used for the model. In FIG. 14A, dashed arrow 1408 has the same length and direction as the dashed arrow 1304 in FIG. 13. As shown in FIG. 14B, this information, along with an indication of the time that the two-dimensional image was captured, t, allows for the computation of a seven-dimensional vector representing a trajectory point 1408 for the wand or endoscope, as discussed above with reference to FIG. 5F. Thus, when a trainee scans a particular patient or physical model with which an accurate three-dimensional digital model is already associated, the images captured during this scan can be used to determine the trajectory of the wand during a training scam. The ability to determine the trajectory of the wand during a training session provides the foundation for automated and semi-automated training subsystems that can be incorporated into an oral-cavity-imaging-and-modeling system.

FIGS. 15A-G illustrate one example user interface for an automated or semi-automated training system that trains technicians to efficiently and accurately scan oral cavities using oral-cavity-imaging-and-modeling systems. The user interface is displayed on the display screen of the oral-cavity-imaging-and-modeling system as well as, in certain implementations, on display screens of remote computer systems to allow remote training supervisors to follow a training session. In alternative implementations, a local computer system connected with the oral-cavity-imaging-and-modeling system is used both to display the training user interface as well as to carry out computing tasks associated with training. The user interface 1500 includes a training-scan-indication window 1502, a real-time-position window 1504, graphical indications of needed spatial 1506 and orientation 1508-1510 changes in the spatial position and orientation of the wand, an elapsed-time indication 1512, and a model window 1514. These features are described, below, with reference to FIGS. 15B-G that show a sequence of information displays during a training session.

Figure 15A:
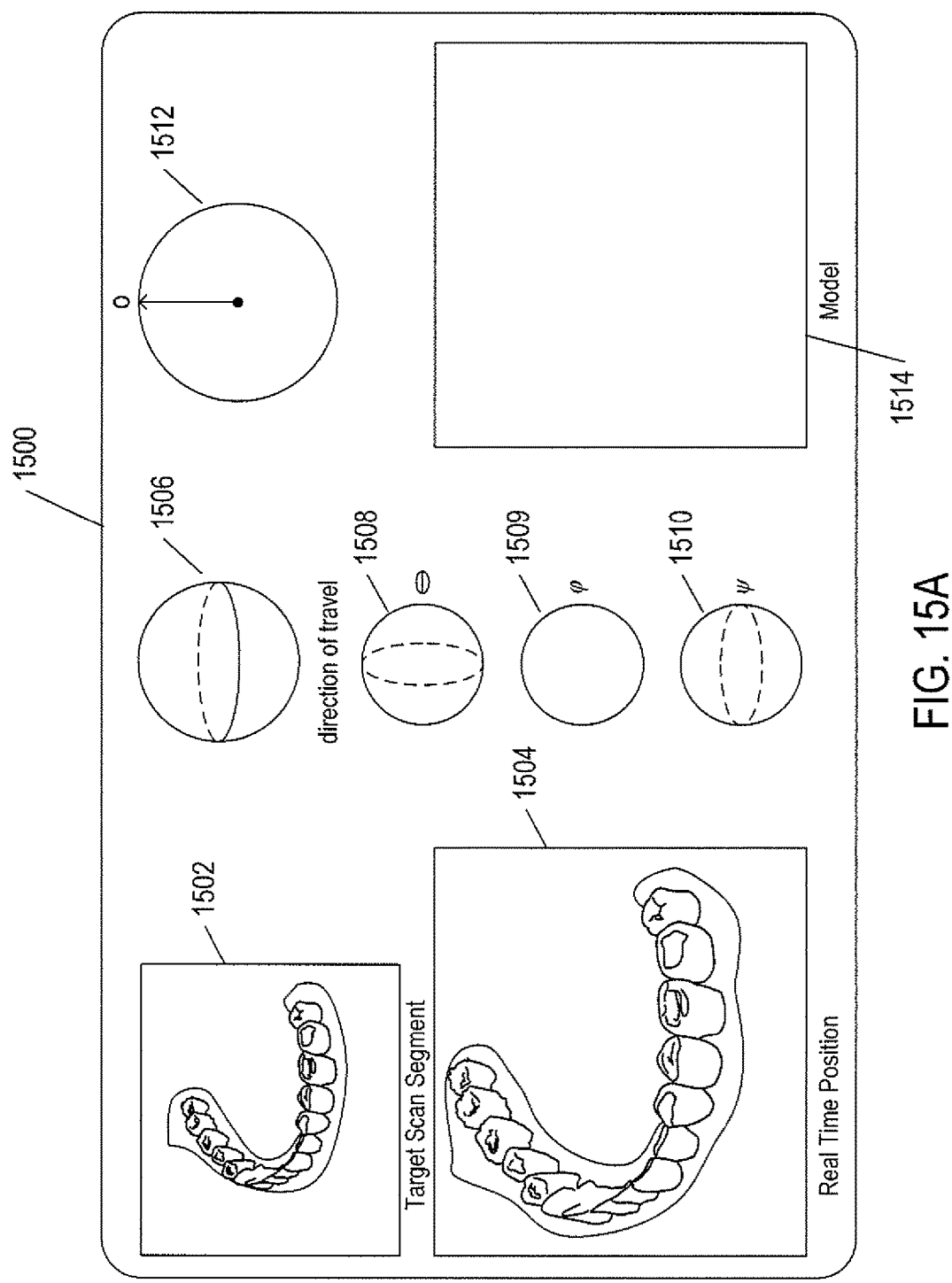
FIGS. 15A-G illustrate one example user interface for an automated or semi-automated training system that trains technicians to efficiently and accurately scan oral cavities using oral-cavity-imaging-and-modeling systems.
Figure 15B:
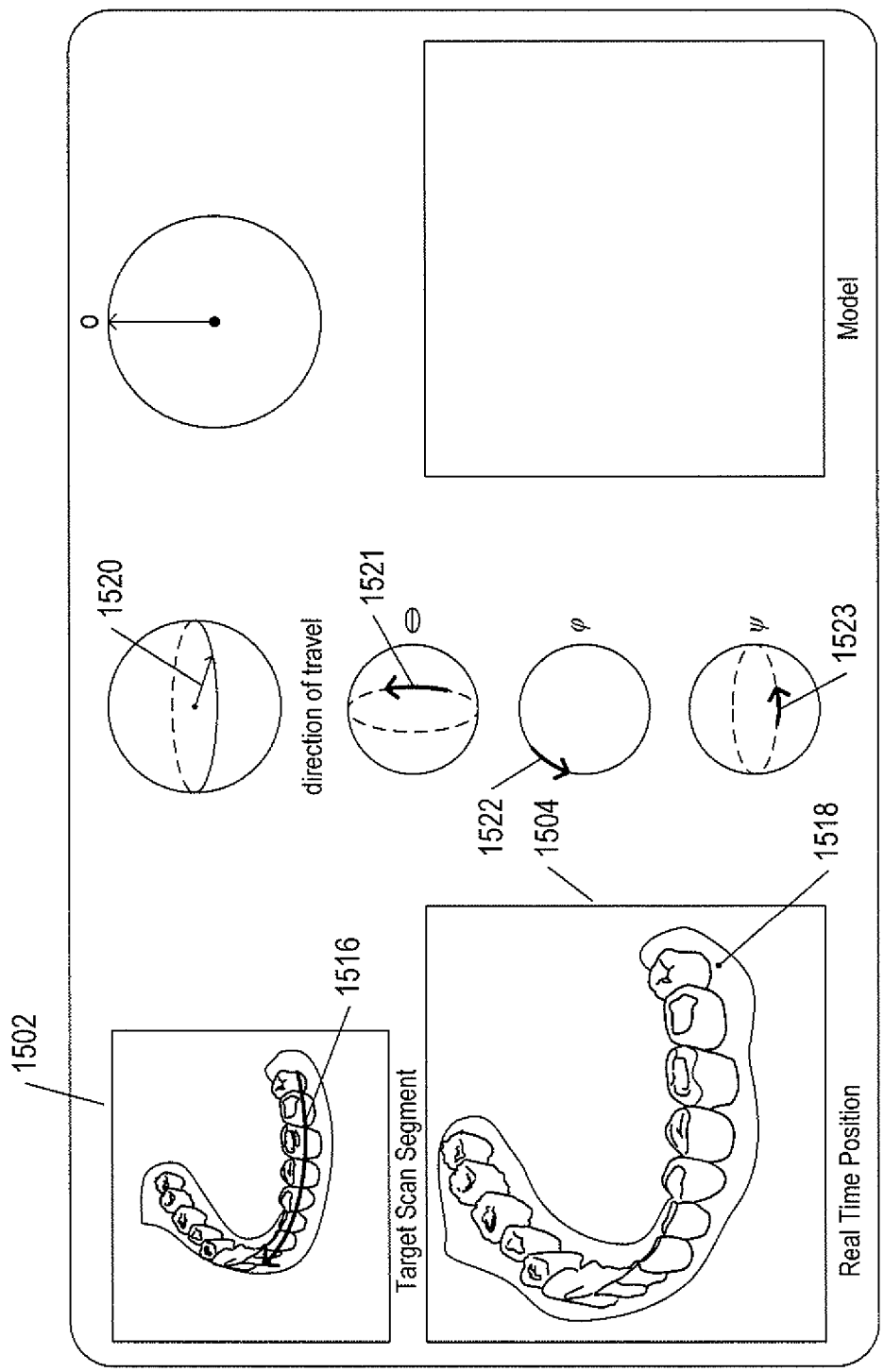
Figure 15C:
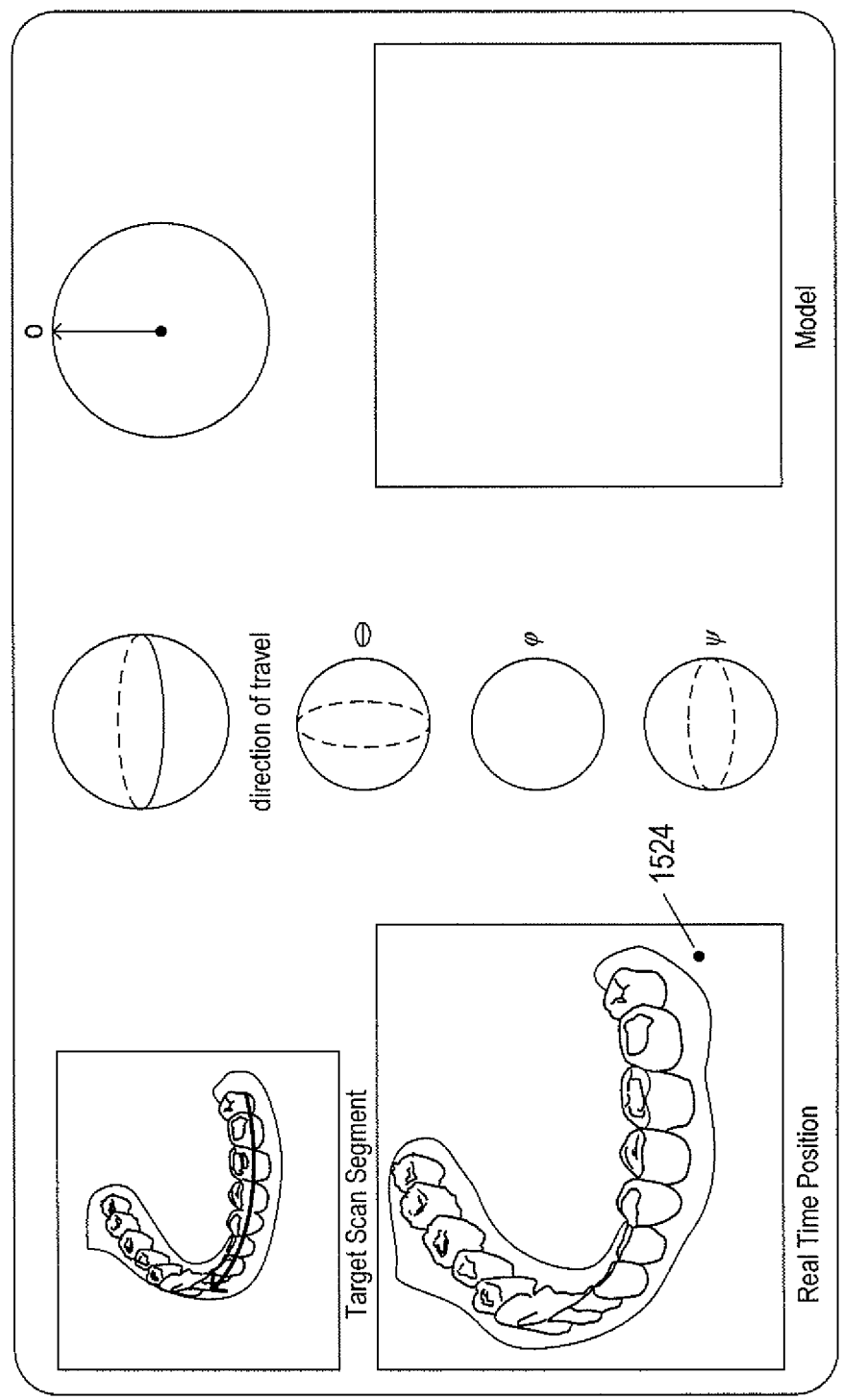
Figure 15D:
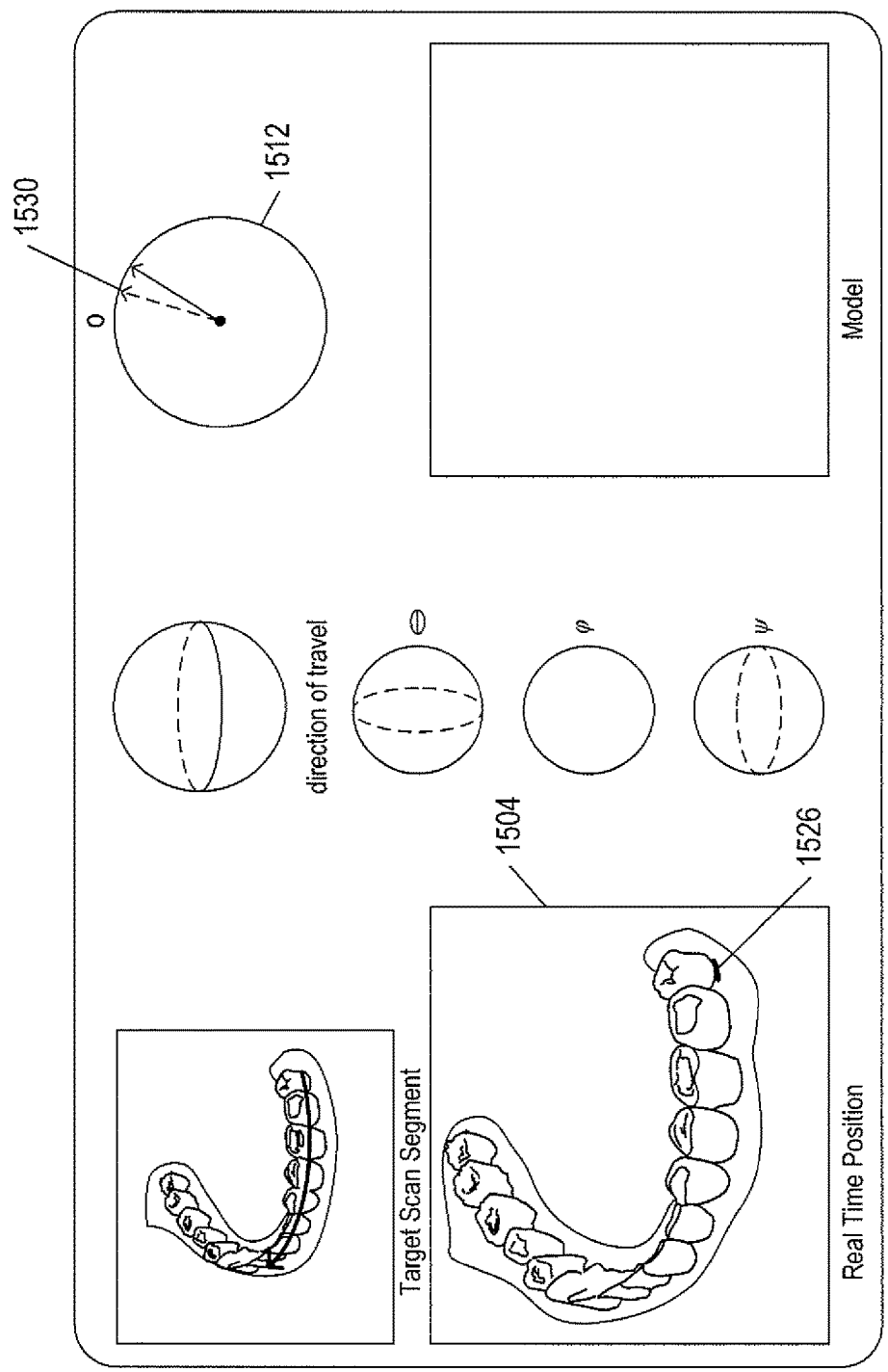

FIG. 15B shows an initial information display, when a trainee has activated the wand and is attempting to position the wand to initiate a scan. The training-scan-indication window 1502 uses a curved arrow or other graphical indication 1516 to indicate to the trainee a particular scan or scan segment to next carry out during the training session. The real-time-position window 1504 displays a current wand position 1518. Because the current spatial position and rotational orientation of the wand does not coincide with a point within any trajectory envelope that would produce an acceptable three-dimensional digital model of the scanned oral cavity or oral-cavity model, the oral-cavity-imaging-and-modeling system displays graphical indications 1520-1523 of spatial translations and rotations needed to position the wand appropriately to start the scan. As shown in FIG. 15C, once the technician has properly positioned and oriented the wand, as represented by position 1524, an audible or visual indication may be made to the trainee to commence scanning. In FIG. 15D, the trainee has begun scanning a row of teeth or a model of a row of teeth. The spatial trajectory of the scan is indicated graphically 1526 in the real-time-position window 1504. Because the trajectory falls within the trajectory envelope of an acceptable scan, no indications are displayed for moving or rotating the wand. The elapsed-time display 1512 shows an indication of the elapsed time of the training scan 1528 as well as an indication of an optimal elapsed time 1530. In this case, the trainee has moved the wand somewhat too slowly, as a result of which the trajectory may be approaching an unacceptable trajectory or non-optimal trajectory.

Figure 15E:
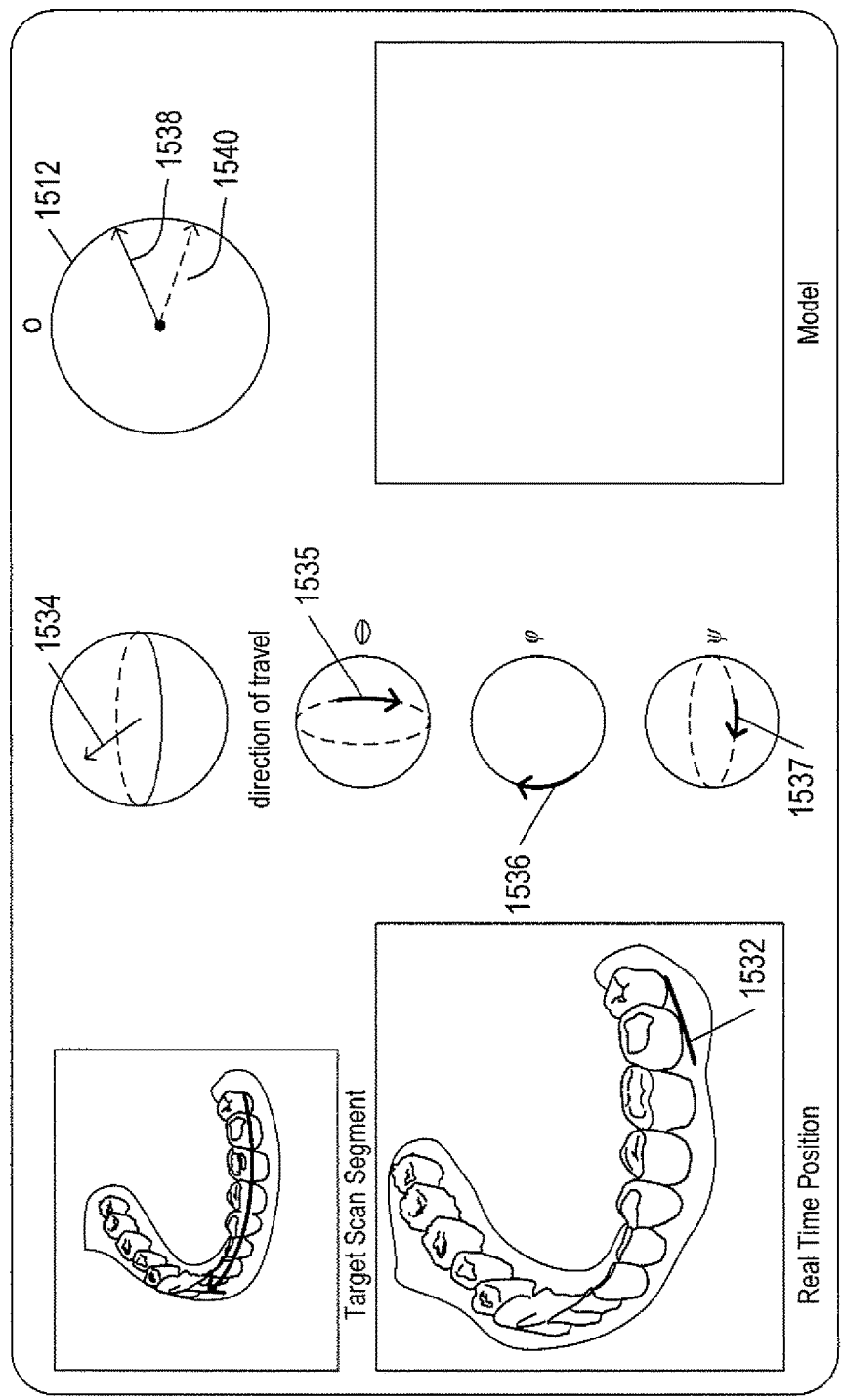

FIG. 15E shows the display after the scan has proceeded further. The spatial trajectory up to the current point in time is shown graphically 1532 in the real-time-position window 1504. In this case, the spatial trajectory and wand orientation have departed from either an acceptable or optimal trajectory, depending on the goals of the particular training session, as a result of which the training subsystem displays indications of spatial and rotational movements needed to return to an acceptable or optimal scan trajectory 1534-1537. The elapsed-time indicator 1512 now shows that the elapsed time for the training scan 1538 is lagging an acceptable or optimal elapsed time 1540, indicating that the trainee is now moving the wand too quickly.

Figure 15F:
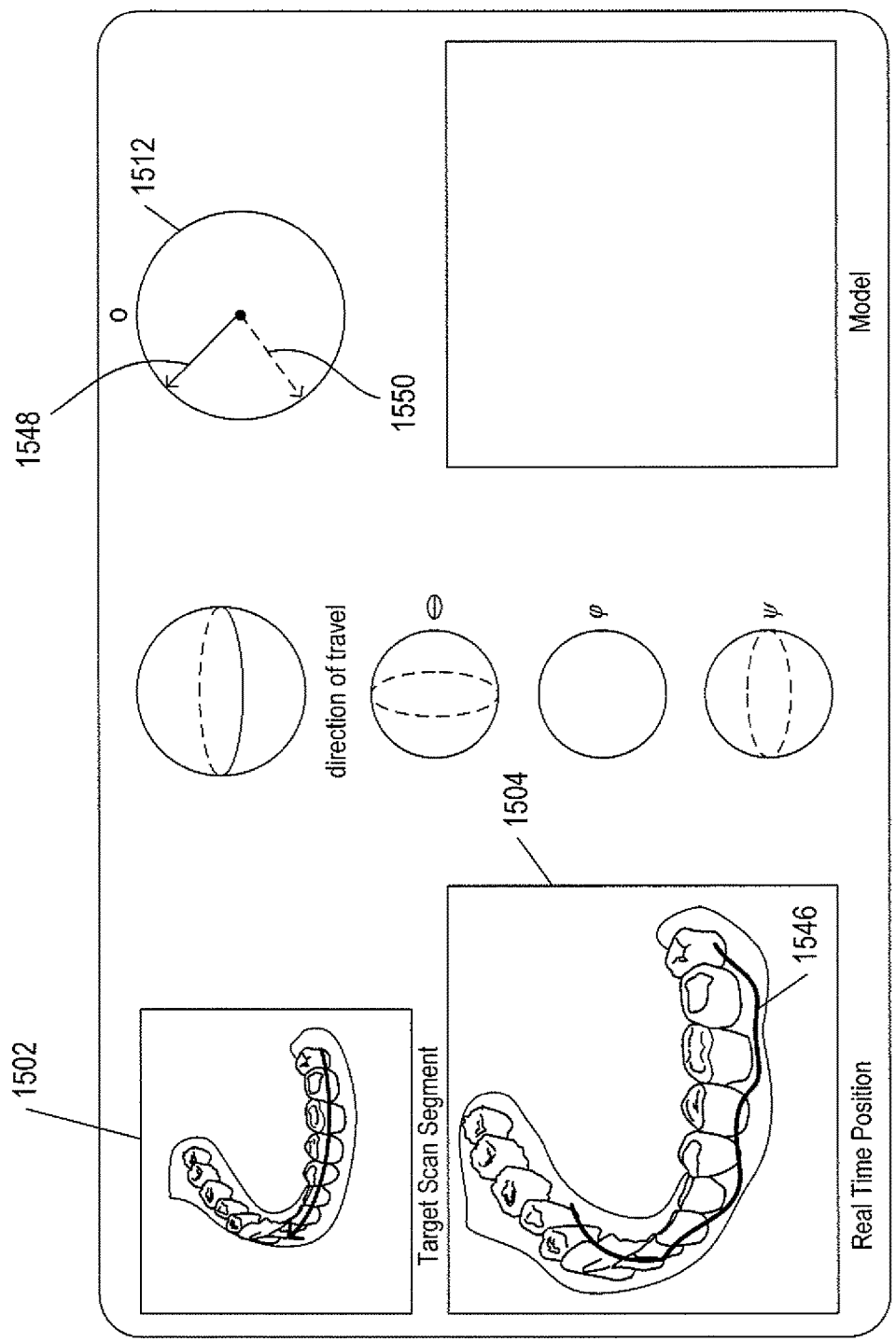

FIG. 15F shows the user-interface display for the training session after the trainee has completed the scan operation indicated in the training-scan-indication window 1502. The spatial trajectory of the trainee's scan is shown by a three-dimensional curve 1546 in the real-time-position window 1504. The elapsed-time indication 1512 indicates a final elapsed time 1548 for the trainee's scan which is significantly greater than an acceptable or optimal elapsed time 1550, depending on the goal of the training session. Thus, over the course of the entire scan, the trainee moved the wand too quickly.

Figure 15G:
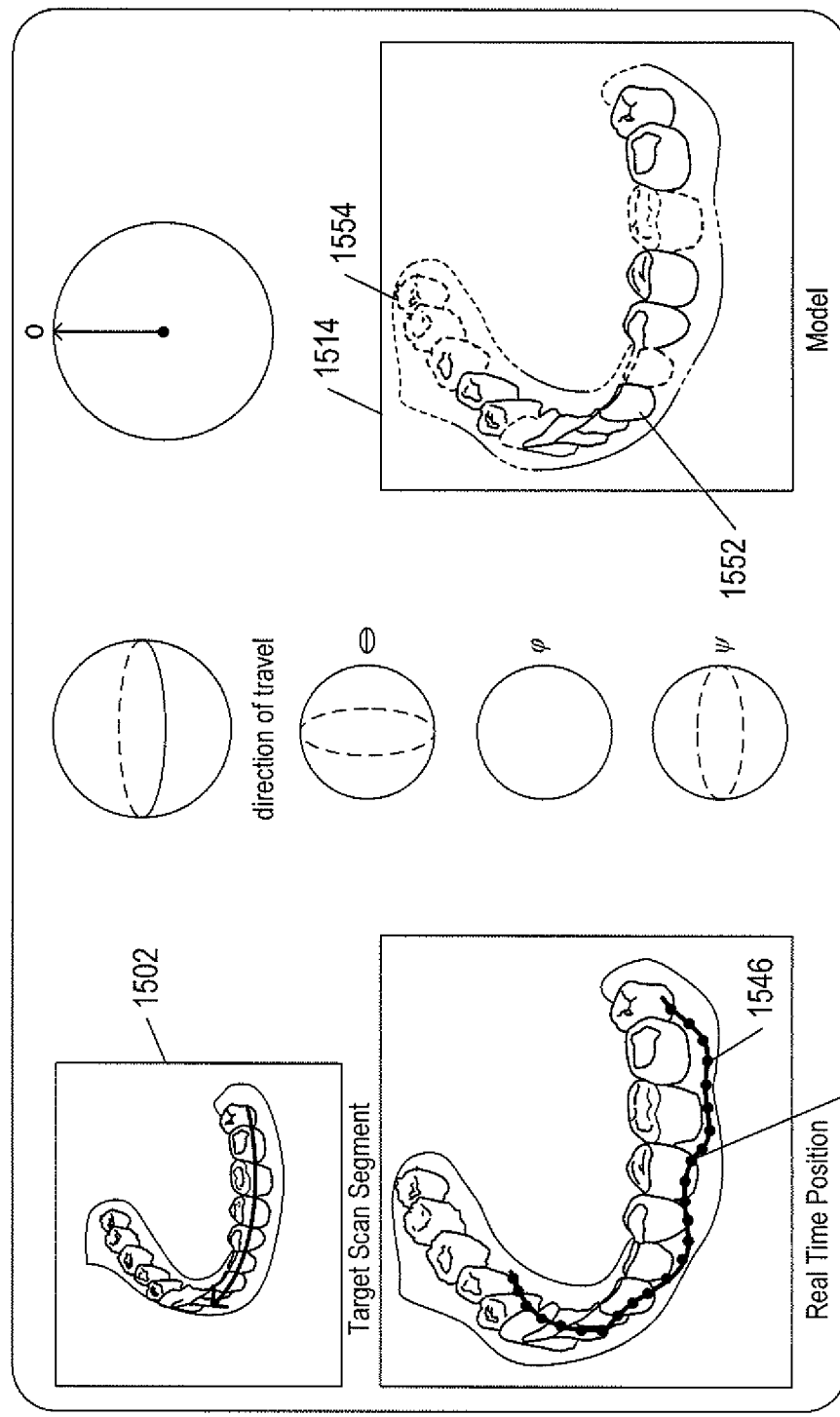

FIG. 15G shows a final display of the training user interface following completion of the scan indicated in the training-scan-indication window 1502. The model window 1514 now displays the three-dimensional digital model generated from information collected during the training scan. Those portions that have been accurately determined are shown in solid lines, such as tooth 1552, while the portions that have failed to have been generated from the scan are shown in dashed lines, such as tooth 1554. In addition, the user interface may display any number of different metrics for the training session, such as indications of the percent of coverage of the generated three-dimensional model, indications of the degree of departure of the scan trajectory from an acceptable or optimal scan, depending on the goal of the training session, and much additional information. For example, the graphical indication of the spatial trajectory of the training scan 1546 may be annotated with points, such as point 1556, where images were captured. This can be correlated with a previously generated accurate three-dimensional digital model to determine those portions of the scan trajectory which were unacceptable or non-optimal and in which insufficient images were captured for generating the three-dimensional digital model.

Figure 16:
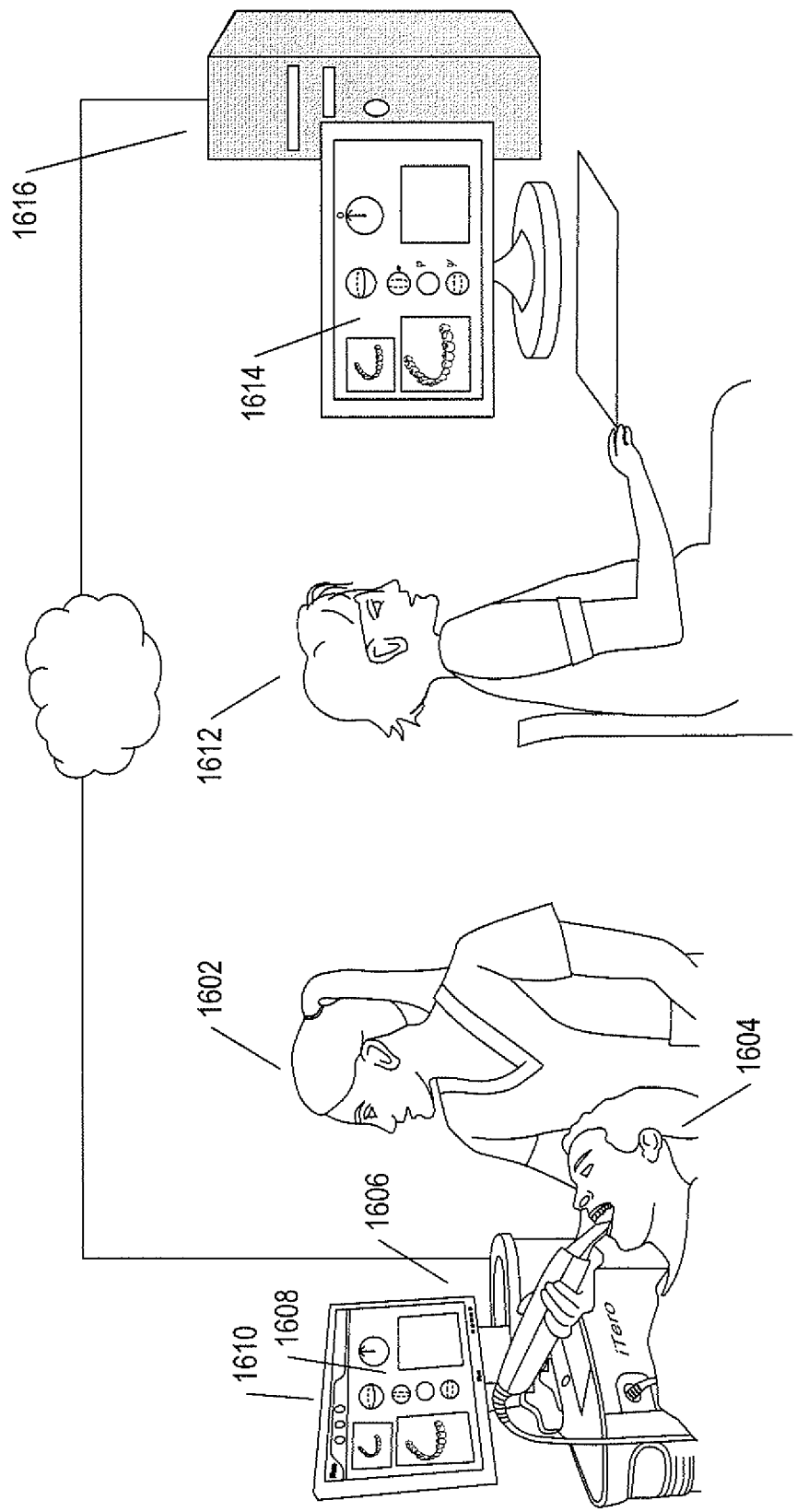
FIG. 16 illustrates use of one implementation of the automated or semi-automated training system that trains technicians to efficiently and accurately scan oral cavities using oral-cavity-imaging-and-modeling systems.

FIG. 16 illustrates use of one implementation of the automated or semi-automated training system that trains technicians to efficiently and accurately scan oral cavities using oral-cavity-imaging-and-modeling systems. As shown in FIG. 16, the trainee 1602 scans a patient 1604 for whom an accurate three-dimensional digital oral-cavity model has been previously prepared and stored in the oral-cavity-imaging-and-modeling system 1606. As the trainee carries out an indicated scan, the trainee can watch the training user interface 1608 displayed on the display device 1610 of the oral-cavity-imaging-and-modeling system. A remote training supervisor 1612 can follow the same displayed information 1614 on a remote computer system 1616 connected to the oral-cavity-imaging-and-modeling system 1606. In addition, the training supervisor may receive a video of the trainee and patient on a separate display device or in an additional display window in order to observe the trainee's actions during the training session. The trainee and training supervisor may additionally communicate over an audio connection or by audio-visual communications. All of the information collected during training sessions may be digitally stored and subsequently retrieved for review and for monitoring a trainee's progress over multiple training sessions. In certain implementations, multiple training supervisors interact with multiple, geographically distinct computer systems to observe and participate in training sessions.

FIG. 17 illustrates two different data structures that are maintained by the training subsystem of an oral-cavity-imaging-and-modeling system during training sessions to facilitate the calculation and display of information by a training user interface and for other training purposes. A first array 1702 stores trajectory points, discussed above with reference to FIG. 5F. In certain implementations, the trajectory points are encoded as vectors in a seven-dimensional vector space, with elements corresponding to time, spatial coordinates, and rotational angles. The trajectory points are computed, as discussed above with reference to FIGS. 13-14B, from images captured during training scans. The trajectory points are sorted in time-of-capture order. Various cells of the array can be marked to indicate the starting points and ending points of scans and subscans 1706-1709. A second array 1712 stores captured images obtained during a training scan by the oral-cavity-imaging-and-modeling system. These captured images are annotated with the time of capture, such as time value 1714 associated with captured image 1716. In certain cases, every image captured during a training scan may be stored in the array. In other implementations, the images are stored only long enough to compute trajectory points from the images, except in the case of images that also correspond to an image that would have been captured and stored during a regular scan by the oral-cavity-imaging-and-modeling system. These latter images are used to continuously construct a training-session three-dimensional model from the images captured during the training scan. The training-session three-dimensional model can be compared to an accurate, previously generated three-dimensional model for the particular patient or a physical model that is the subject of the training session in order to determine metrics for the accuracy and completeness of the training-session three-dimensional model. The data stored in the two arrays 1702 and 1712 forms the basis for information and feedback provided by an automated or semi-automated training system.

Figure 18A:
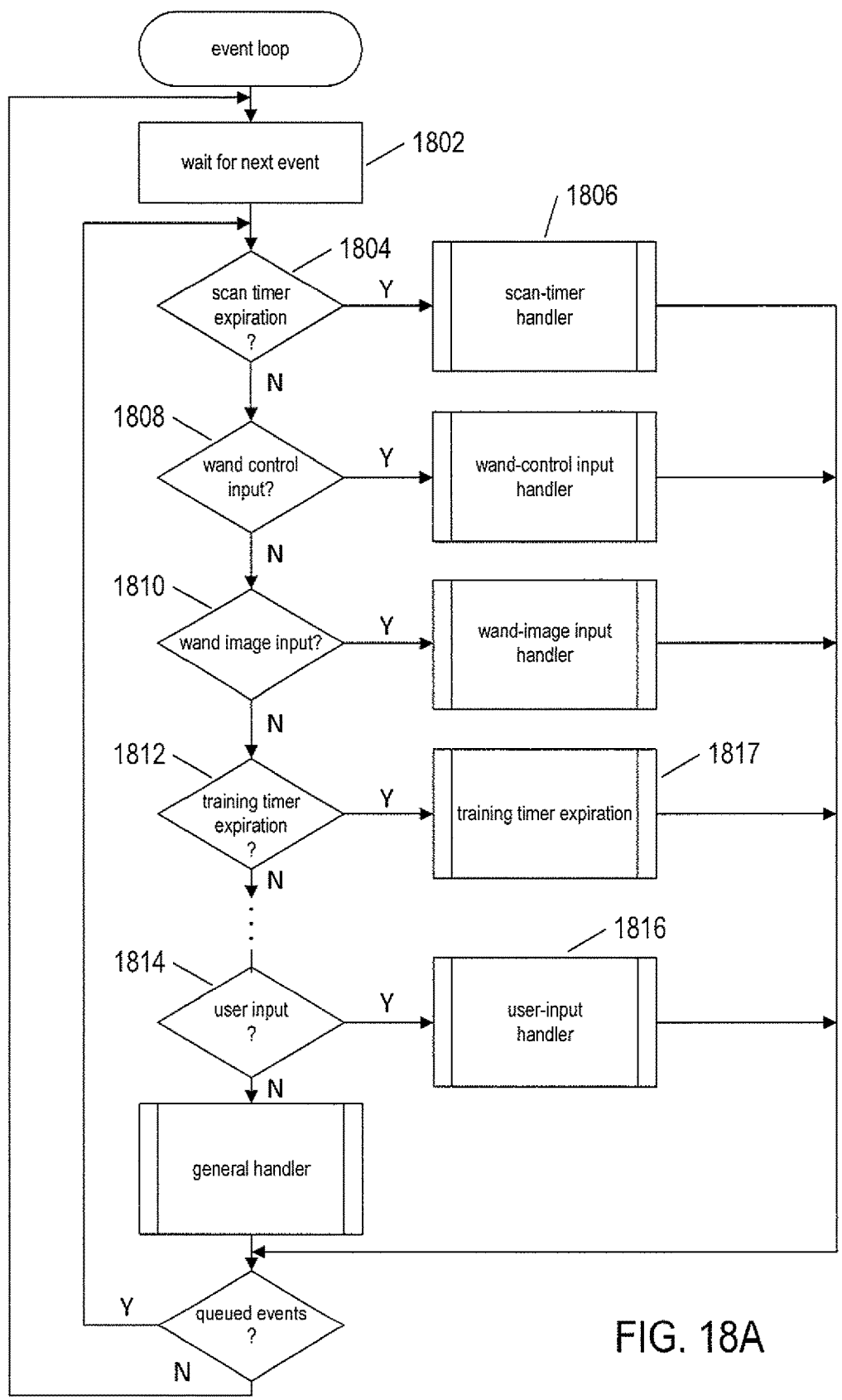
FIGS. 18A-H provide control-flow diagrams that illustrate implementation of one example automated training subsystem incorporated within an oral-cavity-imaging-and-modeling system for training oral-cavity-imaging-and-modeling-system technicians to efficiently and accurately scan patients.

FIGS. 18A-H provide control-flow diagrams that illustrate implementation of one example automated training subsystem incorporated within an oral-cavity-imaging-and-modeling system for training oral-cavity-imaging-and-modeling-system technicians to efficiently and accurately scan patients. FIG. 18A shows a training-subsystem event loop that continuously runs in order to handle all of the various types of events that occur during a training system. This event loop lies at the lowest level of a training-subsystem control program. The training-subsystem control program interfaces to an operating system or guest operating system within the oral-cavity-imaging-and-modeling system which includes a lower-level event loop for handling the various types of hardware events that occur during operation of an oral-cavity-imaging-and-modeling system. In step 1802, the event loop waits for a next event. Then, in a series of conditional steps, the type of next-occurring event is determined and an appropriate handler called for the event. For example, events may include scan-timer expirations, detected in step 1804 and handled by a call to a scan-timer-expiration handler 1806. Other events include wand control input, detected in step 1808, wand image input, detected in step 1810, expiration of a training timer, detected in step 1812, and user input to a keyboard, touch screen, voice-activated subsystem, or other input device, detected in step 1814.

Figure 18B:
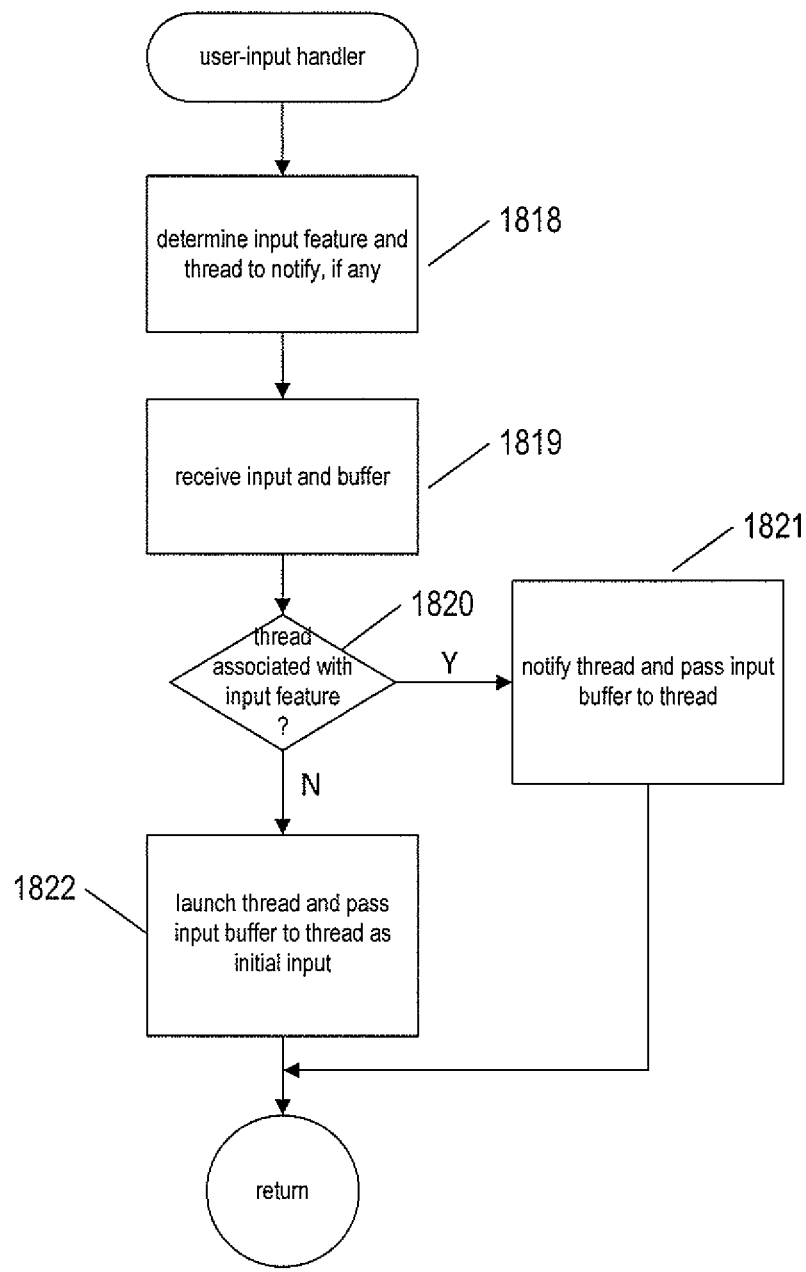

FIG. 18B illustrates one of the handlers called from conditional statements in the event loop illustrated in FIG. 18A, FIG. 18B illustrates the user-input handler called in step 1816 of FIG. 18A. In step 1818, the user-input handler determines the input feature or particular device feature from which the input was received and any thread associated with that input feature to notify that an input event has occurred. In step 1819, the user-input handler receives the input and buffers the input. When there is a thread associated with the input feature, as determined in step 1820, then, in step 1821, the user-input handler notifies the thread and passes the input stored in the input buffer to the thread. Otherwise, in step 1822, the user-input handler launches an appropriate thread for unregistered input and passes the input buffer to the thread as initial input to the thread.

Figure 18C:
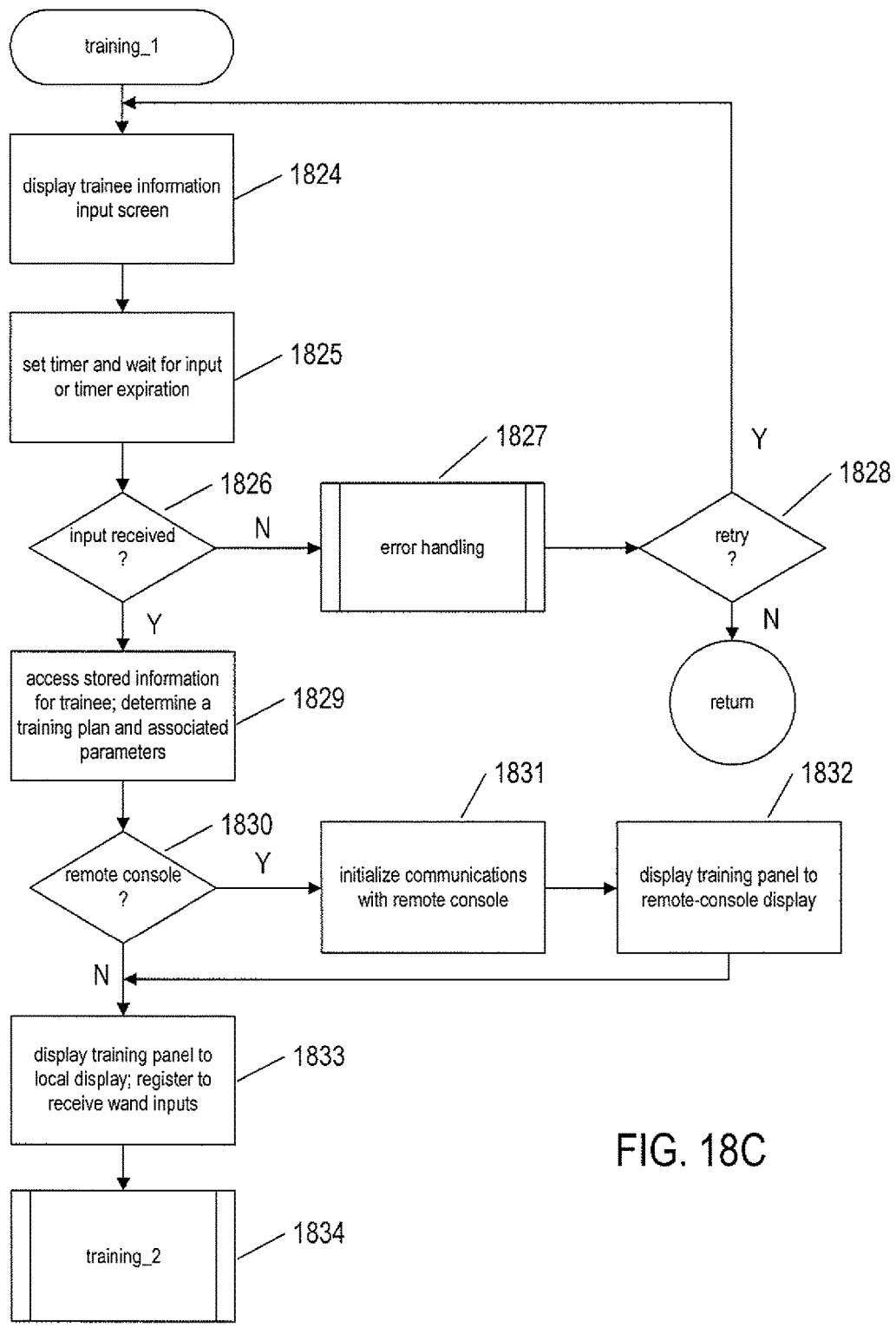
Figure 18D:
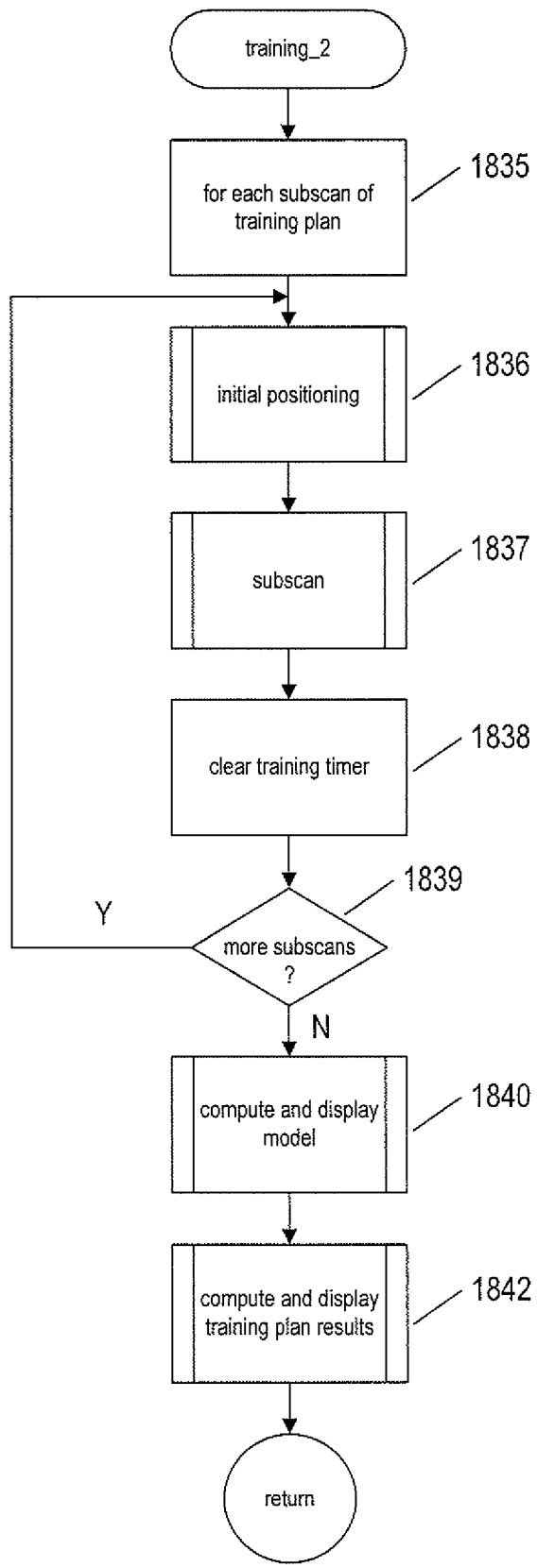

FIGS. 18C-D illustrate a training thread that is invoked by user input to an input feature that launches the training thread. In step 1824, the training thread displays a trainee-information-input screen to collect information from the trainee. In step 1825, the training thread sets a timer and waits for input to be received. When input is not received after timer expiration, as determined in step 1826, error handling is undertaken in step 1827, after which the training thread terminates or trainee-information-input screen is again displayed, as determined in step 1828. When trainee information is received, in step 1829, the trainee information is used to access stored information for the trainee, and perhaps supplement the stored information, in order to determine a training plan for the current training session along with associated training-plan parameters. When there is a remote training console for the training session, as determined in step 1830, the training thread initializes communications with remote console, in step 1831, and displays the training panel, or training user interface, to the remote console display in step 1832. In step 1833, the training thread displays the training panel to the local display on the oral-cavity-imaging-and-modeling system and registers the training thread to receive wand inputs and other types of events associated with the scanning operation. It is assumed that, when a remote training panel has been displayed, all subsequent output to the training panel is transmitted to both the locally displayed and remotely displayed training panel. In step 1834, the second part of the training thread, shown in FIG. 18D, is invoked.

A training session may include numerous subscans that together constitute a single training scan. The number and types of subscans are encoded in the training-plan parameters determined in step 1829. In the for-loop of steps 1835-1839 of FIG. 18D, the training thread carries out a training subscan for each subscan in the training plan. Each subscan involves initial positioning, carried out in step 1836, monitoring of the subscan, carried out in step 1837, and clearing of a training timer following completion of the subscan in step 1838. After the subscans are completed, a training-session three-dimensional digital model is computed from those images captured during the training scan that would have been captured during a normal scanning procedure and displayed in the model window of the user input to the trainee, in step 1840. Additional training plan results and metrics may be computed and displayed to the trainee in step 1842. As discussed above, all of the displayed information, including the generated three-dimensional digital model and results provide various types of feedback to the trainee to indicate how well the trainee accomplished the goal of the current training session. These metrics may include degree of coverage, degree of completion of the three-dimensional digital model, degree of accuracy of the three-dimensional digital model, suggestions for improving efficiency and accuracy in the trainee's scanning techniques, and many other types of information. The training model may be continuously displayed, as it is being constructed, displayed after completion of a training subscan, or displayed after the completion of a training scan.

Figure 18E:
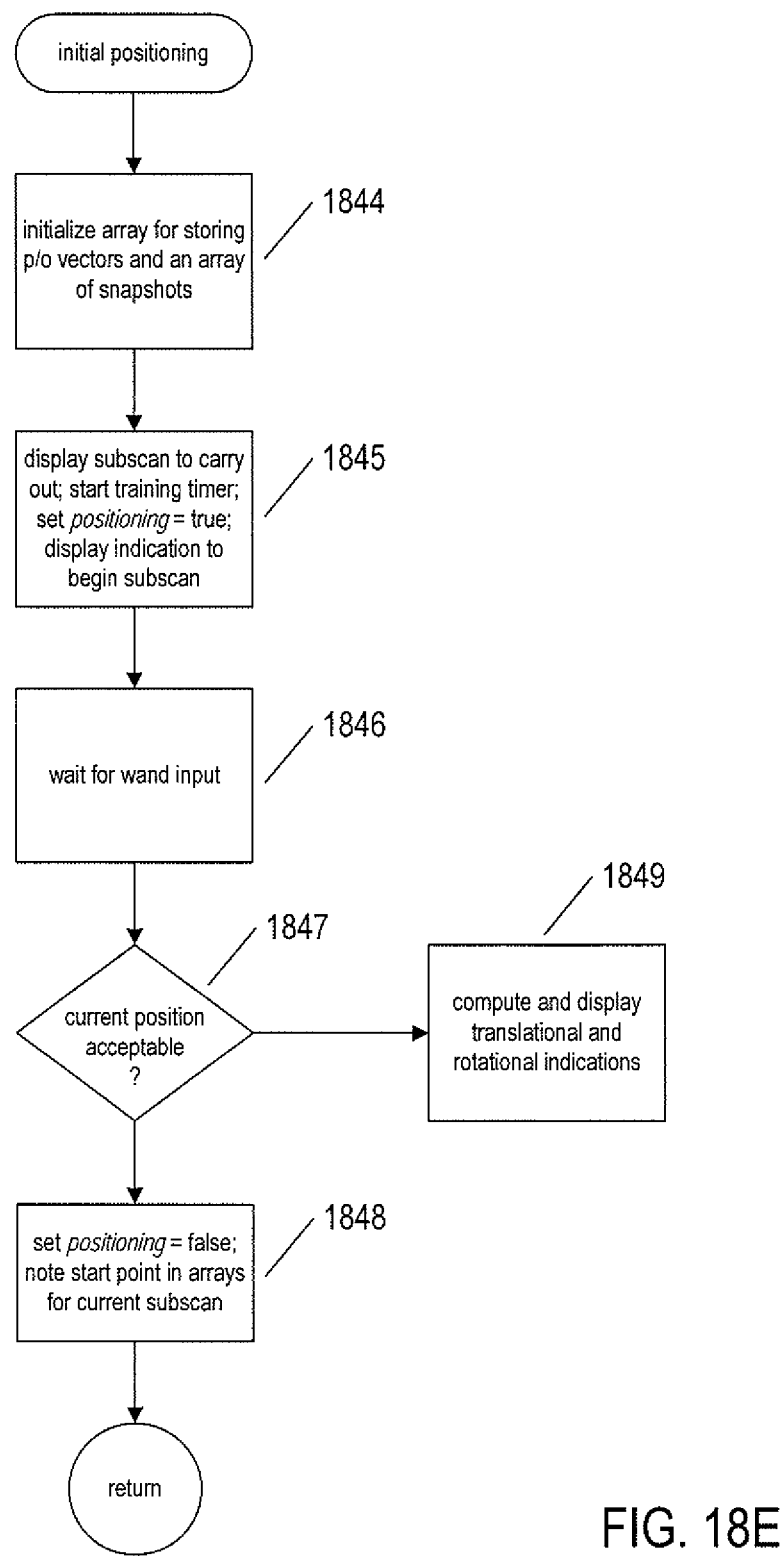

FIG. 18E provides a control-flow diagram for the initial-positioning step 1836 in FIG. 18D. In step 1844, the initial-positioning routine initializes the arrays, discussed above with reference to FIG. 17, for storing trajectory points, or time/position/orientation vectors, and the array of snapshots. Then, in step 1845, the initial-positioning routine displays an indication of the subscan to be carried out, in the training-scan-indication window of the user interface, sets a Boolean variable positioning to TRUE, starts a training timer, and displays or produces an indication to the trainee to begin a subscan. In step 1846, the initial-positioning routine waits for wand input to indicate that the trainee has begun to position the wand for initiation of the scan. During this time, images are being captured and trajectory points computed from those images, from which the spatial position and rotational orientation of the wand is computed, along with various other types of computed values, such as the spatial velocity and rotational velocity of the wand. When the current position of the wand is acceptable, as determined in step 1847, the Boolean variable positioning is set to false and the start point for the subscan is noted in the trajectory-point array, in step 1848. Otherwise, the training subsystem computes and displays translational and/or rotational indications, in step 1849, to the trainee in order to direct the trainee to properly position the wand for the indicated subscan.

Figure 18F:
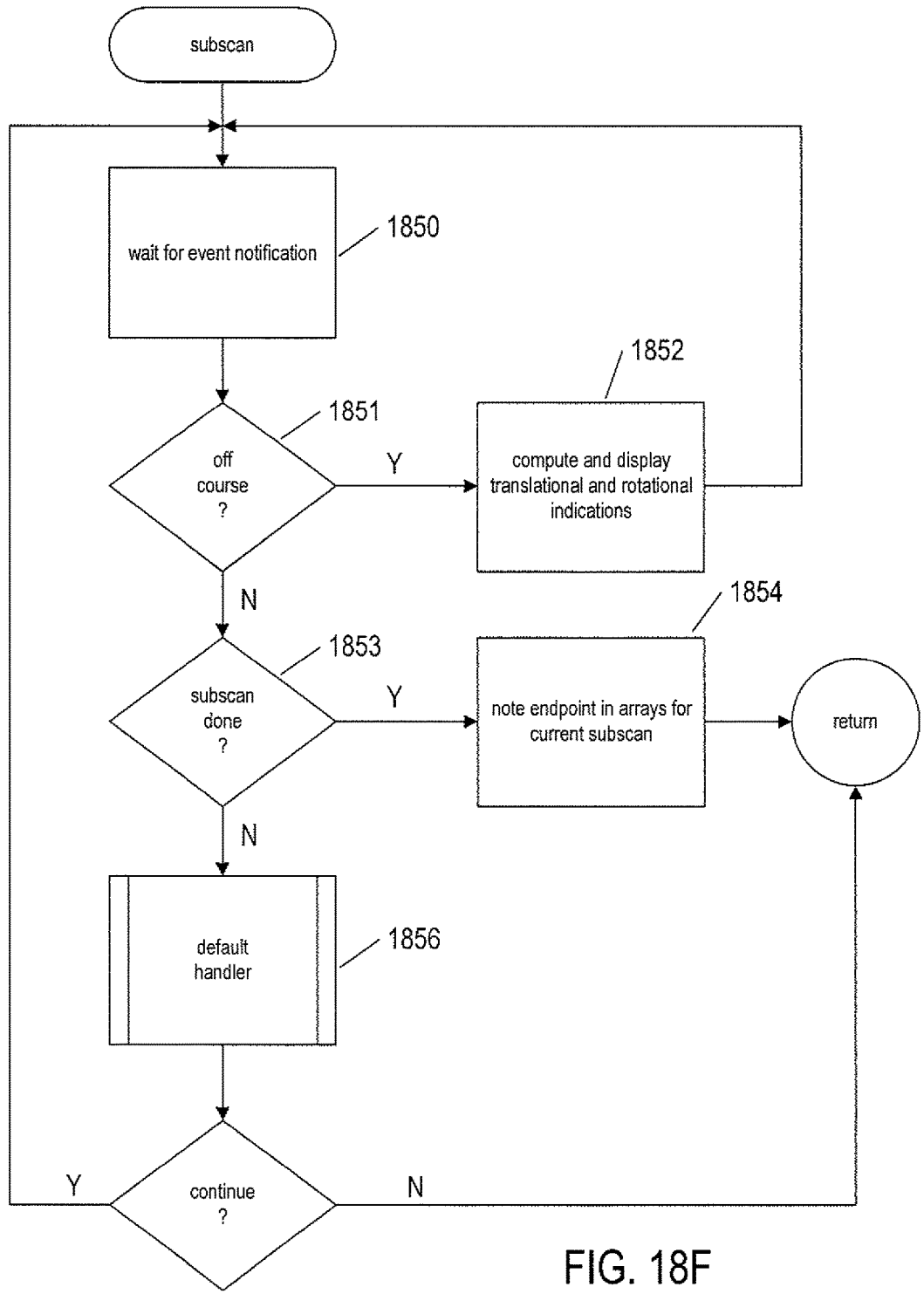

FIG. 18F provides a control-flow diagram for the routine "subscan" invoked in step 1837 of FIG. 18D. During the subscan carried out by a trainee, the routine "subscan" waits for a next event notification, in step 1850, and for each event notification, carries out an appropriate action. When the event notification is an off-course event indicating that the wand trajectory has departed from the envelope of an acceptable or optimal trajectory, as detected in step 1851, the routine "subscan" computes and displays translational and/or rotational indications to guide the trainee to return to the trajectory of an acceptable or optimal scan in step 1852. When the event is a subscan-done event, as determined in step 1853, then the routine "subscan" notes the end point in the trajectory-point array for the current subscan and returns, in step 1854. Other types of events that occur during the subscan may be handled by a default handler 1856. After handling of a particular event, the routine "subscan" either continues to wait for another event, in the case that the event is a routine non-terminating event or returns, in the case of a terminating event, such as a subscan-done event or any of various of different types of error events that may be handled by the default handler.

Figure 18G:
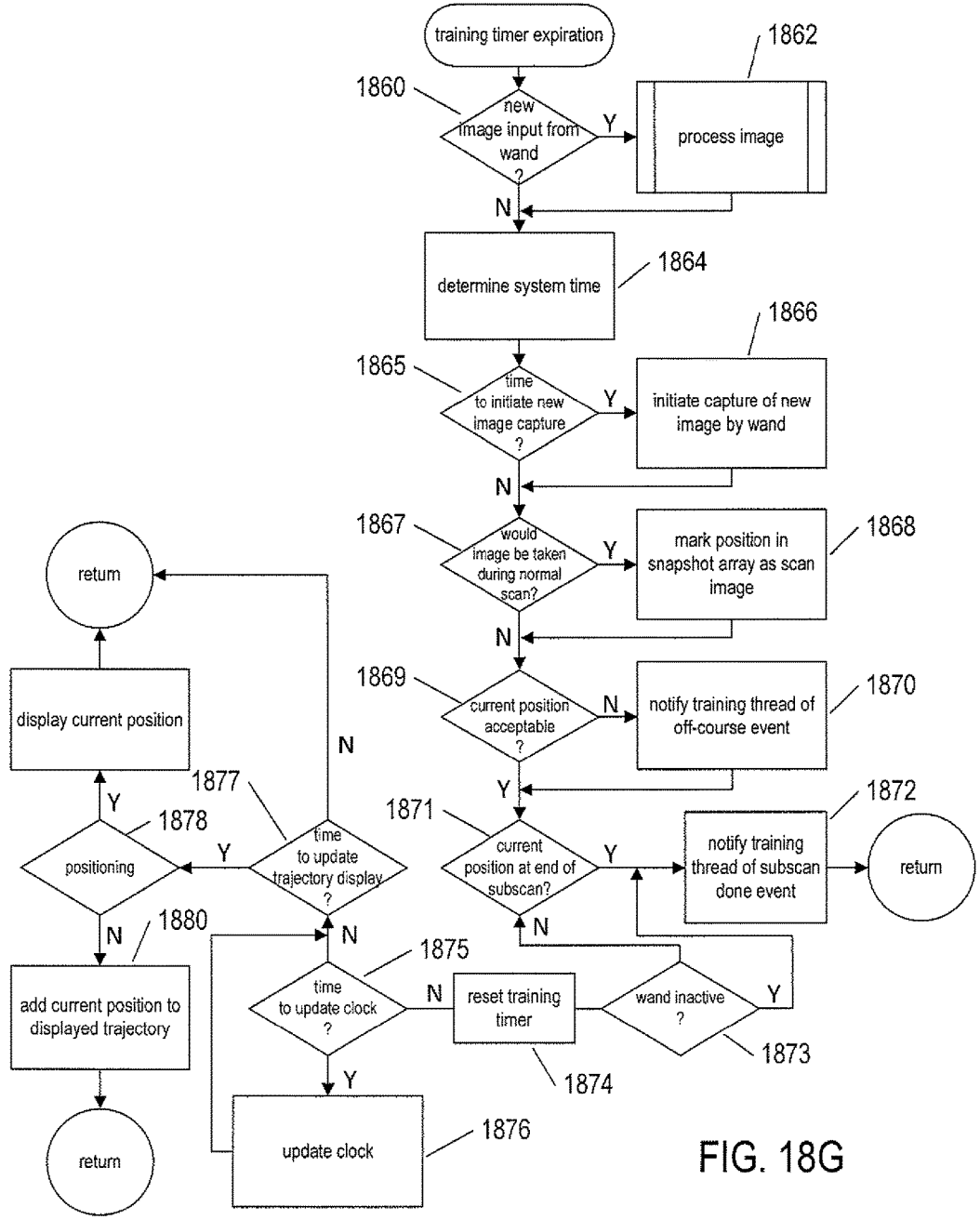

As the subscan is initialized and carded out by a trainee, the training timer expires and is reset at a relatively high frequency, in order for the oral-cavity-imaging-and-modeling system to rapidly capture images and compute wand positions and orientations as well as to compute derived values, such as the translational and rotational speeds of the wand. FIG. 18G is a control-flow diagram for the training-timer-expiration handler, called in step 1817 of FIG. 18A. When there is a new input image available from the wand, as determined in step 1860, a routine "process image" is called in step 1862 to process the image. In step 1864, the current system time is determined. When the current system time indicates that it is time to initiate a new image capture, as determined in step 1865, capture of a new image by the wand is initiated in step 1866. When an image would be captured by the oral-cavity-imaging-and-modeling system during a regular scan at the current point in time, based on the trajectory of the wand and other considerations, as determined in step 1867, a position in the snapshot array is marked as a regular-scan image, in step 1868. This may be the position of the most recently captured image or the position at which the next-captured image will be stored in the array. When the current position of the wand has strayed outside of the envelope of an acceptable or optimal wand trajectory, depending on the goal of the training session, as determined in step 1869, then, in step 1870, the training-timer-expiration handler notifies the training thread of an off-course event. When the current position represents the end of a subscan, as determined in step 1871, the training-timer-expiration handler notifies the training thread of a subscan-done event, in step 1872. When the wand has been inactive for some threshold amount of time, as determined in step 1873, the training-timer-expiration handler also notifies the training thread that a subscan-done event has occurred. Otherwise, the training-timer-expiration handler resets the training timer in step 1874. When the current time indicates that it is time to update the elapsed-time indicator, as determined in step 1875, the elapsed-time indicator is updated in step 1876. When the current system time indicates that it is time to update the real-time-position, or trajectory display, as determined in step 1877, then when initial positioning is occurring, as determined in step 1878, the current position of the wand is displayed in step 1879. Otherwise, during a training scan or subscan, the current position is added to a displayed spatial trajectory in step 1880.

Figure 18H:
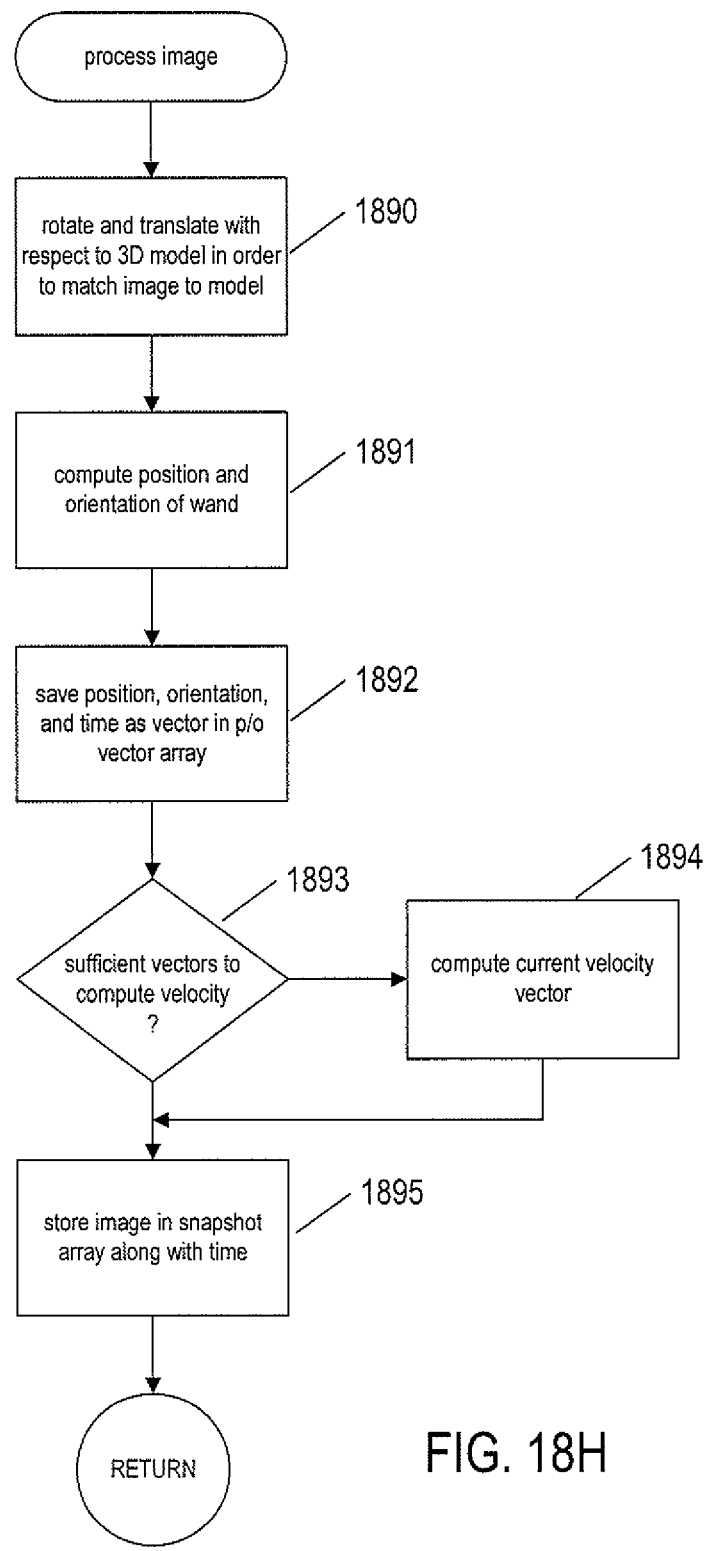

FIG. 18H provides a control-flow diagram for the routine "process image" called in step 1862 of FIG. 18G. In step 1890, the routine "process image" rotates and translates the newly captured image with respect to the three-dimensional digital model previously obtained for the patient or model that is being scanned in the training session in order to best match the image to a projection from a particular position on the surface of the model, as discussed above with reference to FIGS. 13-14B. Then, in step 1891, the routine "process image" computes the position and orientation of the wand based on the rotations and translations needed to match the image with a projection from the three-dimensional digital model. The position, orientation, and time are saved as a vector in the trajectory-point array in step 1892. When there are sufficient vectors stored in the array to determine the velocities of the wand, as determined in step 1893, the velocities of the wand are computed in step 1894 from stored trajectory points over some preceding time window. Velocities may include a spatial velocity as well as three different rotational velocities. Finally, in step 1895, the image is stored in the image array along with the time. In certain embodiments, only those images that correspond to images that would have been captured by the oral-cavity-imaging-and-modeling system during an actual scan may be stored while in other implementations, those images are marked as normal-scan images but all of the captured images are maintained in the array.

Although the present invention has been described in terms of particular embodiments, it is not intended that the invention be limited to these embodiments. Modifications within the spirit of the invention will be apparent to those skilled in the art. For example, any of many different types of absolute or relative coordinate systems can be used for expressing spatial and rotational coordinates for the wand with respect to an imaged object during normal scans and training scans. Such coordinate systems may be based on Cartesian coordinate systems, various types of curve or linear coordinate systems, or groups of mathematically related coordinate systems. Many different types of user-interface displays may be provided to trainees during training sessions and may present many additional and different types of visual queues, visual information, and results and suggestions. In various implementations, the user interface may be displayed on a personal computer connected to the oral-cavity-imaging-and-modeling system rather than on the display of the oral-cavity-imaging-and-modeling system. The three-dimensional digital model computed based on a training scan may be continuously prepared and displayed on the user interface as the scan is carried out or, as in the described implementation, may be created following all of the subscans in a training scan. Many different implementations of an automated or semi-automated training system can be obtained by varying any of many different design and implementation parameters, including hardware platforms, display devices, programming languages, modular organizations, data structures, control structures, and many other such design and implementation parameters. Automated training systems may computationally generate all displayed results, suggestions, and user feedback while semi-automated training systems may allow a training supervisor to locally or remotely assist in guiding a trainee through audio, touch-screen, or keyboard inputs. Automated and semi-automated training systems may be partially implemented in cloud-computing-facility computers or other remote systems, including distributed systems, which receive wand position and orientation data from an oral-cavity-imaging-and-modeling system through any of various electronic communications media.

It is appreciated that the previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

The invention claimed is:

1. An automated training system that monitors a training scan to display training information, the automated training system comprising:
   one or more processors;
   one or more memories that are accessed by the one or more processors;
   a display device; and
   computer instructions, stored in one or more of the one or more memories that, when executed by the automated training system, control the automated training system to:
   display a training user interface on the display device,
   continuously capture images of multiple surfaces of a three-dimensional, solid object from a wand that illuminates the one or more surfaces and receives reflected and scattered light from the one or more illuminated surfaces as the wand is moved along a trajectory to scan the one or more surfaces during the training scan,
   compute and store, in one or more of the one or more memories, an ordered set of spatial positions and orientations of the wand by matching images of the captured images to projections of a previously created three-dimensional digital model of the solid object wherein the ordered set of spatial positions and orientations of the wand comprises a plurality of vector points and vector point includes: three spatial coordinates, three orientation coordinates, and an indication of the time at which an image was captured from which the spatial coordinates and orientation coordinates were calculated, and
   wherein, for each vector point, the three spatial coordinates and three orientation coordinates are computed by:
   searching the previously created three-dimensional digital model of the solid object for a projection of a portion of the previously created three-dimensional digital model of the solid object that best matches with the captured image and determining a translation and rotation of the captured image, relative to the previously created 3D digital model of the solid object, that places the captured image in a position corresponding to the projection; and computing coordinates of the spatial positions and orientations of the wand from the determined translation and rotation, compute and display, within the training user interface on the display device, information regarding the accuracy and efficiency of the training scan from the stored ordered set of spatial positions and orientations of the wand.

2. The automated training system of claim 1 wherein the solid object is teeth and tissues within the oral cavity of a patient.

3. The automated training system of claim 1 wherein the solid object is a three-dimensional model of teeth and tissues.

4. The automated training system of claim 1 further comprising:

designating, as normal-scan images, those images captured during the training scan that would have been captured during a normal, non-training scan in which the wand follows a trajectory equivalent to the trajectory of the training scan; and computing, during or after the training scan, a training-scan-generated three-dimensional digital model of the solid object.

5. The automated training system of claim 4 wherein the information regarding the accuracy and efficiency of the training scan includes one or more of:

indications of the translational velocity of the wand;
indications of the rotational velocity of the wand;
indications of the elapsed time of the scan;
indications of the accuracy of the training-scan-generated three-dimensional digital model of the solid object;
indications of the degree of coverage of the normal-scan images with respect to the surface of the previously created three-dimensional digital model of the solid object;
indications of the spatial trajectory of the wand during the training scan;
indications of the points, in the spatial trajectory of the wand during the training scan, at which normal-scan images were captured;
indications of the similarity of the spatial trajectory of the wand during the training scan to an acceptable-trajectory envelope within which normal-scan images can be captured and used to construct an accurate three-dimensional digital model of the solid object; and
indications of the similarity of the spatial trajectory of the wand during the training scan to an optimal trajectory envelope within which normal-scan images can be captured and used to construct an accurate three-dimensional digital model of the solid object.

6. The automated training system of claim 1 wherein the user interface is additionally displayed on the display of a remote computer system.

7. The automated training system of claim 1 wherein a trainee interacting with the automated training system communicates with a user of the remote computer system by voice and inputs to one or more input devices.

8. The automated training system of claim 1 wherein a captured image is one of:

a two-dimensional photographic image; and
a three-dimensional surface image.

9. A method controlled by computer instructions executed in an automated training system having one or more processors, one or more memories that are accessed by the one or more processors, and a display device, the method comprising:

continuously capturing images of multiple surfaces of a three-dimensional, solid object from a wand that illuminates the one or more surfaces and receives reflected and scattered light from the one or more illuminated surfaces as the wand is moved along a trajectory to scan the one or more surfaces during a training scan; and computing and storing, in one or more of the one or more memories, an ordered set of spatial positions and orientations of the wand by matching the captured images to projections of a previously created three-dimensional digital model of the solid object, wherein computing the ordered set of spatial positions and orientation of the wand further includes, for each captured image:

searching the previously created three-dimensional digital model of the solid object for a projection of a portion of the previously created three-dimensional digital model of the solid object that best matches with the captured image and determining a translation and rotation of the captured image, relative to the previously created 3D digital model of the solid object, that places the captured image in a position corresponding to the projection; and computing coordinates of the spatial positions and orientations of the wand from the determined translation and rotation, further wherein the ordered set of spatial positions and orientations of the wand includes a plurality of vector points and each vector point comprises:

three spatial coordinates;
three orientation coordinates; and
an indication of the time at which the image was captured from which the spatial coordinates and orientation coordinates were calculated.

10. The method of claim 9 further comprising;

designating, as normal-scan images, those images captured during the training scan that would have been captured during a normal, non-training scan in which the wand follows a trajectory equivalent to the trajectory of the training scan; and computing, during or after the training scan, a training-scan-generated three-dimensional digital model of the solid object.

11. An method of claim 10 further comprising:

computing and displaying, on the display device, information regarding the accuracy and efficiency of the training scan from the stored ordered set of spatial positions and orientations of the wand.

12. An method of claim 11 wherein the information regarding the accuracy and efficiency of the training scan includes one or more of:

indications of the translational velocity of the wand;
indications of the rotational velocity of the wand;
indications of the elapsed time of the scan;
indications of the accuracy of the training-scan-generated three-dimensional digital model of the solid object;

indications of the degree of coverage of the normal-scan images with respect to the surface of the previously created three-dimensional digital model of the solid object;

indications of the spatial trajectory of the wand during the training scan;

indications of the points, in the spatial trajectory of the wand during the training scan, at which normal-scan images were captured;

indications of the similarity of the spatial trajectory of the wand during the training scan to an acceptable-trajectory envelope within which normal-scan images can be captured and used to construct an accurate three-dimensional digital model of the solid object; and indications of the similarity of the spatial trajectory of the wand during the training scan to an optimal trajectory envelope within which normal-scan images can be captured and used to construct an accurate three-dimensional digital model of the solid object.

13. The method of claim 9 wherein the solid object is teeth and tissues within the oral cavity of a patient.

14. The method of claim 9 wherein the solid object is a three-dimensional model of teeth and tissues.

15. The method of claim 9 wherein a captured image is one of:

a two-dimensional photographic image; and a three-dimensional surface image.

* * * * *